United States Patent
Eto et al.

(10) Patent No.: US 9,034,922 B2
(45) Date of Patent: *May 19, 2015

(54) COMPOSITION FOR MAINTAINING FUNCTION OF PLATELETS

(75) Inventors: Koji Eto, Bunkyo-ku (JP); Ryoko Ohnishi, Bunkyo-ku (JP); Hiromitsu Nakauchi, Bunkyo-ku (JP); Takahiko Murata, Bunkyo-ku (JP)

(73) Assignees: THE UNIVERSITY OF TOKYO, Tokyo (JP); KAKEN PHARMACEUTICAL CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/824,325

(22) PCT Filed: Sep. 16, 2011

(86) PCT No.: PCT/JP2011/071190
§ 371 (c)(1),
(2), (4) Date: Mar. 15, 2013

(87) PCT Pub. No.: WO2012/036257
PCT Pub. Date: Mar. 22, 2012

(65) Prior Publication Data
US 2013/0177900 A1    Jul. 11, 2013

(30) Foreign Application Priority Data
Sep. 17, 2010 (JP) .................................. 2010-210146

(51) Int. Cl.
| A61K 31/27 | (2006.01) |
| A01N 1/02 | (2006.01) |
| A61K 31/165 | (2006.01) |
| A61K 31/18 | (2006.01) |
| A61K 31/4453 | (2006.01) |
| A61K 31/5375 | (2006.01) |
| C07D 295/135 | (2006.01) |
| C07C 317/28 | (2006.01) |

(Continued)

(52) U.S. Cl.
CPC ............ *A01N 1/0226* (2013.01); *A61K 31/165* (2013.01); *A61K 31/18* (2013.01); *A61K 31/4453* (2013.01); *A61K 31/5375* (2013.01); *A61K 2039/55555* (2013.01); *C07D 295/135* (2013.01); *C07C 317/28* (2013.01); *C12N 5/0644* (2013.01); *C12N 2501/70* (2013.01)

(58) Field of Classification Search
CPC .................. A01N 1/0226; A61K 2039/55555; A61K 31/165; A61K 31/18; A61K 31/4453; A61K 31/5375; C07C 317/28; C07D 295/135
USPC ............... 435/2, 372, 355; 546/234; 544/159; 562/621

See application file for complete search history.

(56) References Cited

U.S. PATENT DOCUMENTS

| 7,511,144 B2 * | 3/2009 | Shimano et al. .............. 546/157 |
| 2004/0180901 A1 | 9/2004 | Finlay et al. |
| 2004/0186088 A1 | 9/2004 | Bandarage et al. |

(Continued)

FOREIGN PATENT DOCUMENTS

| CN | 1668302 | 9/2005 |
| CN | 101346353 | 1/2009 |

(Continued)

OTHER PUBLICATIONS

Accession No. 2007:2724 CAPLUS, 2007.*

(Continued)

*Primary Examiner* — Wu-Cheng Winston Shen
*Assistant Examiner* — Jean Cornet
(74) *Attorney, Agent, or Firm* — Sughrue Mion, PLLC

(57) ABSTRACT

A composition for maintaining a function of platelets, the composition comprising, as an active ingredient, a compound represented by the following general formula (I) or a salt thereof, or a solvate thereof:

[Chem. 1]

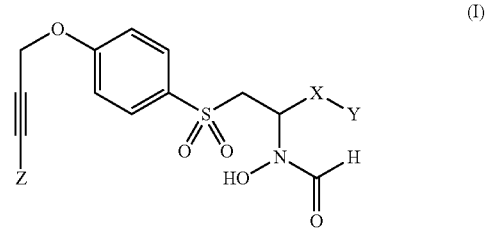

(I)

wherein
  X represents a phenylene group;
  Y represents any one of a hydrogen atom and $-(CH_2)_m R^1$;
  wherein
    m represents an integer of any one of 0 to 4; and
    $R^1$ is any one of $-NR^5 COR^2$, $-NR^5 SO_2 R^2$, and $-NR^3 R^4$;
    wherein $R^2$ represents any one of a C1 to C6 alkyl group, an aryl group, a C1 to C6 alkoxy group, and the like;
    $R^3$ and $R^4$ represent a C1 to C6 alkyl group or the like; and
    $R^5$ represents any one of a hydrogen atom, a C1 to C6 alkyl group, and the like; and
  Z represents any one of a hydrogen atom and a C1 to C6 alkyl group.

12 Claims, 23 Drawing Sheets

(51) Int. Cl.
 *C12N 5/078* (2010.01)
 *A61K 39/00* (2006.01)

(56) References Cited

U.S. PATENT DOCUMENTS

| | | |
|---|---|---|
| 2004/0242928 A1 | 12/2004 | Shimano et al. |
| 2006/0063783 A1 | 3/2006 | Burrows et al. |
| 2009/0221575 A1 | 9/2009 | Gerber et al. |
| 2010/0197016 A1 | 8/2010 | Nakauchi et al. |
| 2011/0053267 A1 | 3/2011 | Nakauchi et al. |
| 2013/0131180 A1 | 5/2013 | Kawai et al. |

FOREIGN PATENT DOCUMENTS

| | | |
|---|---|---|
| EP | 2597084 | 5/2013 |
| JP | 2002535392 | 10/2002 |
| JP | 2005501087 | 1/2005 |
| JP | 2007161686 | 6/2007 |
| JP | 2009513601 | 4/2009 |
| WO | 0044730 | 8/2000 |
| WO | 2004056766 | 7/2004 |
| WO | 2008041370 | 4/2008 |
| WO | 2009119105 | 10/2009 |
| WO | 2009122747 | 10/2009 |
| WO | WO 2009119105 A1 * | 10/2009 |

OTHER PUBLICATIONS

Bergmeier et al., "Tumor Necrosis Factor-α-Converting Enzyme (ADAM17) Mediates GPibα Shedding From Platelets In vitro and In vivo", Circulation Research, 95:677-683 (2004).

Bergmeier et al., "Metalloproteinase inhibitors improve the recovery and hemostatic function of In vitro-aged or -injured mouse platelets", Blood, 102:4229-4235 (2003).

Peterson et al., "The importance of estimating the therapeutic index in the development of matrix metalloproteinase inhibitors", Cardiovascular Research, 69:677-687 (2006).

Skipper et al., "Mutagenicity of Hydroxamic Acids and the Probable Involvement of Carbamoylation", Cancer Research, 40:4704-4708 (1980).

Eto et al., "Saisei Iryo no Saibo Source 3 ES Saibo Yurai Kesshoban", Biomedicine & Therapeutics, 43(6):21-26 (2009).

Musso et al., "N-Hydroxyformamide peptidomimetics as TACE/Matrix metalloprotease inhibitors: oral activity via P1' isobutyl substitution", Bioorganic & Medicinal Chemistry Letters, 11:2147-2151 (2001).

International Search Report for PCT/JP2011/071190 dated Nov. 15, 2011.

Nishikii et al., "Metalloproteinase regulation improves in vitro generation of efficacious platelets from mouse embryonic stem cells", J. Exp. Med., 205(8):1917-1927 (2008).

International Preliminary Report on Patentability for PCT/JP2011/071190 dated Apr. 16, 2013, with Written Opinion dated Nov. 15, 2011.

Levin et al., "Acetylenic TACE inhibitors. Part 1. SAR of the acyclic sulfonamide hydroxamates", Bioorganic & Medicinal Chemistry Letters, 13:2799-2803 (2003).

Communication for European Application No. 11825255.0 dated Sep. 22, 2014, with Supplementary European Search Report (dated Sep. 12, 2014).

Chung et al., "Human embryonic stem cell lines generated without embryo destruction", Cell Stem Cell, 2(2):113-117 (2008).

Codon et al., "Identification of potent and selective TACE Inhibitors via the S1 Pocket", Bioorganic & Medicinal Chemistry Letters, 17(1):34-39 (2007).

* cited by examiner

COMPOSITION FOR MAINTAINING FUNCTION OF PLATELETS

CROSS REFERENCE TO RELATED APPLICATIONS

This is a National Stage of International Application No. PCT/JP2011/071190 filed Sep. 16, 2011, claiming priority based on Japanese Patent Application No. 2010-210146 filed Sep. 17, 2010, the contents of all of which are incorporated herein by reference in their entirety.

STATEMENT OF JOINT RESEARCH AGREEMENT

The invention disclosed herein was made by or on the behalf of The University of Tokyo and Kaken Pharmaceutical Co., Ltd., parties to a joint research agreement within the meaning of 35 U.S.C. §103(c)(3).

TECHNICAL FIELD

The present invention relates to a composition for maintaining a function of platelets, a method for preparing platelets, a blood product comprising platelets, and a method for maintaining a function of platelets in a blood product, which utilize an N-hydroxyformamide derivative.

BACKGROUND ART

For the treatment of blood-related diseases typified by leukemia, it is extremely important to stably amplify and supply blood cells in an amount necessary for such treatment. Thus, to date, many researchers have attempted to efficiently amplify hematopoietic stem cells or hematopoietic progenitor cells.

Among blood cells, megakaryocytes are platelet progenitor cells, i.e., cells producing platelets and are known to form a proplatelet structure (cytoplasmic formation) to produce platelets and play an important role in therapeutic applications. Platelets are essential for blood coagulation (hemostasis). Accordingly, the demand for platelets is extremely high for leukemia, bone marrow transplantation, anticancer therapy, and so forth.

Platelet production has been attempted by administration of thrombopoietin (TPO) and in the way of differentiating umbilical cord blood or bone marrow cells into megakaryocytes, other than a method of collecting blood from blood donors so far. Recently, a method also has been attempted in which hematopoietic progenitor cells are amplified ex vivo to prepare platelets from such progenitor cells. For example, the present inventors have reported: a method for producing platelets in a relatively large amount efficiently from a sac-like structure enclosing hematopoietic progenitor cells, after the sac-like structure was prepared from human embryonic stem cells (ES cells) (PTL 1); a method for efficiently preparing mature megakaryocytes and platelets from induced pluripotent stem cells (iPS cells) in an in-vitro culture system (PTL 2); and so forth.

As described above, researches on the method for preparing platelets per se exogenously have been advanced. However, the function of prepared platelets is poorly stable. For this reason, it is necessary to develop a method that enables preparation of a large amount of functional platelets capable of being stored for an extended period of time.

Binding between platelets and an extracellular matrix is an important process for inducing blood coagulation (hemostasis, thrombus formation, and the like). It is believed that this process is initiated when a platelet receptor GPIb binds to von Willebrand factor (VWF) via an α-subunit (GPIbα). However, it has been reported that under a condition of around 37° C., a metalloproteinase ADAM17 (a disintegrin and metallopeptidase domain 17) sheds an extracellular region of GPIbα (release by cleavage), thereby inhibiting the association between GPIbα and VWF, and the platelets lose blood coagulating ability (NPLs 1 and 2).

Hence, it is anticipated that at least the activity of ADAM17 needs to be suppressed in order to keep the function of platelets prepared in vitro. Actually, the present inventors have reported that the function of platelets prepared in vitro can be kept by adding at an appropriate timing an inhibitor (such as GM6001) directly inhibiting a metalloproteinase activity or a p38 MAP kinase inhibitor indirectly inhibiting activation of the activity of metalloproteinase such as ADAM17 (PTL 3).

Nevertheless, inhibitors such as GM6001 inhibit the activities of not only ADAM17 but also other metalloproteinases (particularly MMP9 and MMP14 essential for hematopoietic function). Hence, when such inhibitors are utilized to prepare platelets in vitro, the inhibitors need to be added at a certain period when platelet production is observed most abundantly. Since such a complex task as getting right timing is required in cell culturing that is poor in consistency and reproducibility, the method for preparing platelets by utilizing these inhibitors has not been satisfactory yet in preparing a large amount of functional platelets and particularly in establishing a plant for platelet production system.

Furthermore, non-selective metalloproteinase inhibitors inhibit the activity of all of metalloproteinases such as membrane type metalloproteinases, secreted metalloproteinases and ADAMs. Accordingly, the in vivo use is believed to bring about a risk of various side effects (adverse influences caused by the inhibition of essential MMPs or ADAMs acting on different organs). Actually, since non-selective metalloproteinase inhibitors cause a severe side effect called musculoskeletal syndrome, the many developments of these inhibitors have been terminated (NPL 3). Moreover, it is suggested that an inhibitor with a hydroxamic acid structure, such as GM6001, should have mutagenicity (NPL 4). Thus, platelets obtained by a method using foregoing inhibitor are not satisfactory even in safety yet.

Meanwhile, at present, there is no effective method for storing platelets prepared from living donors, other than a method in which platelets are stored with agitating at 20° C. to 24° C. Accordingly, it seems effective to prepare platelets under room temperature conditions (20° C. to 24° C.) even when the method for suppressing the metalloproteinase activity of ADAM17 is utilized to keep the function of platelets. Nevertheless, no verification has been made under the room temperature condition at all so far whether or not it is possible to get umbilical cord blood or bone marrow cells differentiated into megakaryocytes, and whether or not it is possible to produce platelets from hematopoietic progenitor cells derived from ES cells or the like.

As described above, a compound practically usable as an active ingredient of a composition for maintaining a function of platelets has not been discovered yet. Hence, a method for obtaining functionally stable platelets in vitro and particularly a method suitable for mass production of highly safe platelets have not been established at present.

CITATION LIST

Patent Literatures

[PTL 1] International Publication No. WO2008/041370
[PTL 2] International Publication No. WO2009/122747
[PTL 3] International Publication No. WO2009/119105

Non Patent Literatures

[NPL 1] Bergmeier et al., Circulation Research, 2004, vol. 95, pp. 677 to 683
[NPL 2] Bergmeier et al., Blood, 2003, vol. 102, pp. 4229 to 4235
[NPL 3] Peterson et al., Cardiovasc. Res., 2006, vol. 69, pp. 677 to 687
[NPL 4] Skipper et al., Cancer Res., 1980, vol. 40, pp. 4704 to 4708

SUMMARY OF INVENTION

Technical Problem

The present invention has been made in view of the above-described problems of the conventional techniques.

An object of the present invention is to identify a compound capable of maintaining a function of platelets by specifically inhibiting a metalloproteinase activity of ADAM17 to suppress GPIbα shedding. Another object of the present invention is to provide a composition for maintaining a function of platelets, to efficiently produce platelets, and to improve the quality maintenance of a blood product, all of which are achieved by utilizing the identified compound.

Solution to Problem

The present inventors have earnestly studied in order to achieve the above objects. As a result, the inventors have revealed that culturing under room temperature condition of 25° fails to differentiate hematopoietic progenitor cells derived from ES cells, iPS cells, or the like into megakaryocytes, or to produce platelets from the megakaryocytes, but that a culture condition around 37° C. is preferable. Hence, the present inventors next searched for a compound capable of specifically inhibiting ADAM17-mediated GPIbα shedding in culturing at around 37° C. As a result, the followings were found out. N-hydroxyformamide derivatives with a particular structure have an inhibitory action specific to ADAM17. When the N-hydroxyformamide derivatives were added to a culture system for producing platelets or to human peripheral blood-derived platelets, GPIbα shedding was suppressed, and the function of the platelets was also maintained under the temperature condition of around 37° C. The present inventors have found out that from such actions of the identified N-hydroxyformamide derivatives, the derivatives are extremely useful for efficient platelet production, improvement in the quality maintenance of a blood product comprising platelets, and so on. These discoveries have led to the completion of the present invention.

The present invention more specifically provides the following inventions.

(1) A composition for maintaining a function of platelets, the composition comprising, as an active ingredient, a compound represented by the following general formula (I) or a salt thereof, or a solvate thereof:

[Chem. 1]

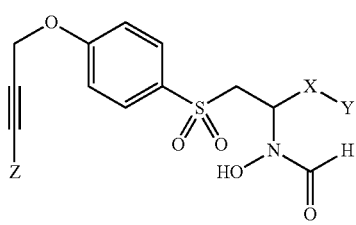

(I)

wherein
X represents a phenylene group;
Y represents any one of a hydrogen atom and —$(CH_2)_m R^1$;
wherein
m represents an integer of any one of 0 to 4; and
$R^2$ is any one of

[Chem. 2]

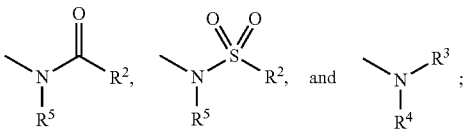

wherein $R^2$ represents any one of a C1 to C6 alkyl group, which may be substituted, an aryl group, which may be substituted, and a C1 to C6 alkoxy group;

$R^3$ and $R^4$ each independently represent any one of a hydrogen atom and a C1 to C6 alkyl group, or $R^3$ and $R^4$ together with an adjacent nitrogen atom may form a nitrogen-containing heterocycle; and $R^5$ represents any one of a hydrogen atom, a C1 to C6 alkyl group, and a C1 to C6 alkylsulfonyl group; and Z represents any one of a hydrogen atom and a C1 to C6 alkyl group.

(2) The composition according to (1), wherein the compound represented by the general formula (I) is anyone of N-[2-(4-but-2-ynyloxybenzenesulfonyl)-1-(4-diethylaminomethylphenyl)ethyl]-N-hydroxyformamide and N-{4-[2-(4-but-2-ynyloxybenzenesulfonyl)-1-(formylhydroxyamino)ethyl]benzyl}methanesulfonamide.

(3) The composition according to any one of (1) and (2) in a form of any one of a reagent for maintaining a function of platelets and an additive to a blood product comprising platelets.

(4) A method for preparing platelets, wherein the method comprises adding, to a culture system for differentiating megakaryocytes from cells capable of differentiating into megakaryocytes and producing platelets from the megakaryocytes, a compound represented by the following general formula (I) or a salt thereof, or a solvate thereof:

[Chem. 3]

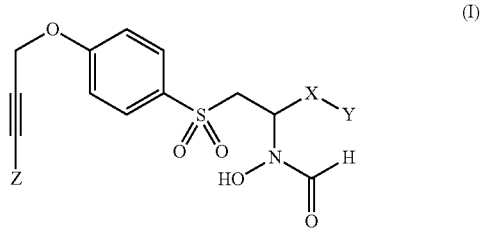

(I)

wherein
X represents a phenylene group;
Y represents any one of a hydrogen atom and —$(CH_2)_m R^1$;

wherein
m represents an integer of any one of 0 to 4; and
$R^1$ is any one of

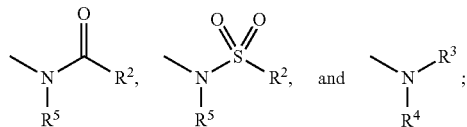

wherein $R^2$ represents any one of a C1 to C6 alkyl group, which may be substituted, an aryl group, which may be substituted, and a C1 to C6 alkoxy group;
$R^3$ and $R^4$ each independently represent any one of a hydrogen atom and a C1 to C6 alkyl group, or $R^3$ and $R^4$ together with an adjacent nitrogen atom may form a nitrogen-containing heterocycle; and
$R^5$ represents any one of a hydrogen atom, a C1 to C6 alkyl group, and a C1 to C6 alkylsulfonyl group; and
Z represents any one of a hydrogen atom and a C1 to C6 alkyl group.

(5) The method according to (4), wherein the compound represented by the general formula (I) is any one of
N-[2-(4-but-2-ynyloxybenzenesulfonyl)-1-(4-diethylaminomethylphenyl)ethyl]-N-hydroxyformamide and
N-{4-[2-(4-but-2-ynyloxybenzenesulfonyl)-1-(formylhydroxyamino)ethyl]benzyl}methanesulfonamide.

(6) The method according to anyone of (4) and (5), wherein a culture temperature in the culture system is 35 to 38° C.

(7) A culture which is a culture system for differentiating megakaryocytes from cells capable of differentiating into megakaryocytes and for producing platelets from the megakaryocytes, and is added to the system with a compound represented by the following general formula (I) or a salt thereof, or a solvate thereof:

[Chem. 5]

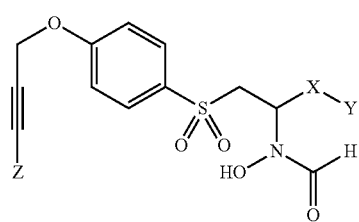

wherein
X represents a phenylene group;
Y represents any one of a hydrogen atom and —$(CH_2)_m R^1$;
wherein
m represents an integer of any one of 0 to 4; and
$R^1$ is any one of

[Chem. 6]

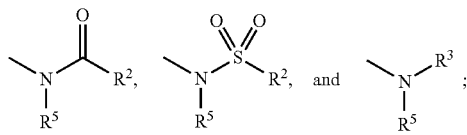

wherein $R^2$ represents any one of a C1 to C6 alkyl group, which may be substituted, an aryl group, which may be substituted, and a C1 to C6 alkoxy group;
$R^3$ and $R^4$ each independently represent any one of a hydrogen atom and a C1 to C6 alkyl group, or $R^3$ and $R^4$ together with an adjacent nitrogen atom may form a nitrogen-containing heterocycle; and
$R^5$ represents any one of a hydrogen atom, a C1 to C6 alkyl group, and a C1 to C6 alkylsulfonyl group; and
Z represents any one of a hydrogen atom and a C1 to C6 alkyl group.

(8) The culture according to (7), wherein the compound represented by the general formula (I) is any one of
N-[2-(4-but-2-ynyloxybenzenesulfonyl)-1-(4-diethylaminomethylphenyl)ethyl]-N-hydroxyformamide and
N-{4-[2-(4-but-2-ynyloxybenzenesulfonyl)-1-(formylhydroxyamino)ethyl]benzyl}methanesulfonamide.

(9) A blood product comprising platelets and a compound represented by the following general formula (I) or a salt thereof, or a solvate thereof:

[Chem. 7]

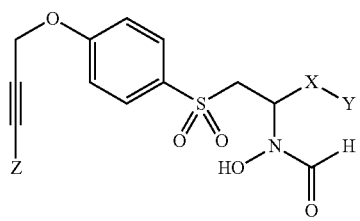

wherein
X represents a phenylene group;
Y represents any one of a hydrogen atom and —$(CH_2)_m R^1$;
wherein
m represents an integer of any one of 0 to 4; and
$R^1$ is any one of

[Chem. 8]

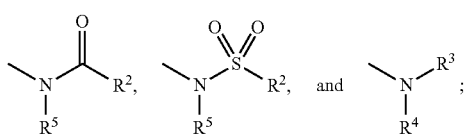

wherein $R^2$ represents any one of a C1 to C6 alkyl group, which may be substituted, an aryl group, which may be substituted, and a C1 to C6 alkoxy group;
$R^3$ and $R^4$ each independently represent any one of a hydrogen atom and a C1 to C6 alkyl group, or $R^3$ and $R^4$ together with an adjacent nitrogen atom may form a nitrogen-containing heterocycle; and
$R^5$ represents any one of a hydrogen atom, a C1 to C6 alkyl group, and a C1 to C6 alkylsulfonyl group; and
Z represents any one of a hydrogen atom and a C1 to C6 alkyl group.

(10) The blood product according to (9), wherein the compound represented by the general formula (I) is anyone of
N-[2-(4-but-2-ynyloxybenzenesulfonyl)-1-(4-diethylaminomethylphenyl)ethyl]-N-hydroxyformamide and
N-{4-[2-(4-but-2-ynyloxybenzenesulfonyl)-1-(formylhydroxyamino)ethyl]benzyl}methanesulfonamide.

(11) A method for maintaining a function of platelets in a blood product, wherein the method comprises adding, to a blood product comprising platelets, a compound represented by the following general formula (I) or a salt thereof, or a solvate thereof:

[Chem. 9]

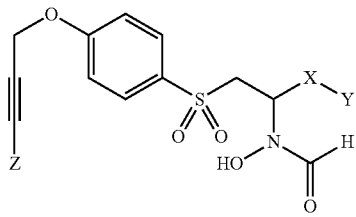

(I)

wherein
X represents a phenylene group;
Y represents any one of a hydrogen atom and —(CH$_2$)$_m$R$^1$;
wherein
m represents an integer of any one of 0 to 4; and
R$^1$ is any one of

[Chem. 10]

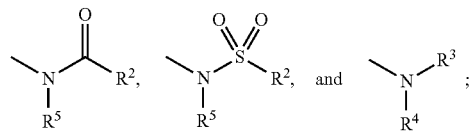

wherein R$^2$ represents any one of a C1 to C6 alkyl group, which may be substituted, an aryl group, which may be substituted, and a C1 to C6 alkoxy group;
R$^3$ and R$^4$ each independently represent any one of a hydrogen atom and a C1 to C6 alkyl group, or R$^3$ and R$^4$ together with an adjacent nitrogen atom may form a nitrogen-containing heterocycle; and
R$^5$ represents any one of a hydrogen atom, a C1 to C6 alkyl group, and a C1 to C6 alkylsulfonyl group; and
Z represents any one of a hydrogen atom and a C1 to C6 alkyl group.

(12) The method according to (11), wherein the compound represented by the general formula (I) is any one of
N-[2-(4-but-2-ynyloxybenzenesulfonyl)-1-(4-diethylaminomethylphenyl)ethyl]-N-hydroxyformamide and
N-{4-[2-(4-but-2-ynyloxybenzenesulfonyl)-1-(formylhydroxyamino)ethyl]benzyl}methanesulfonamide.

Advantageous Effects of Invention

The N-hydroxyformamide derivatives discovered in the present invention are capable of maintaining a function of platelets even under a temperature condition of around 37° C. by specifically inhibiting a metalloproteinase activity of ADAM17 to suppress GPIbα shedding. Thus, the derivatives make it possible to produce a large amount of functionally stable platelets in vitro, and to keep the quality of a blood product comprising platelets.

BRIEF DESCRIPTION OF DRAWINGS

FIG. 1 is a schematic drawing for illustrating a method for inducing megakaryocytes/platelets, under room temperature conditions, from hematopoietic progenitor cells derived from ES cells or the like.

DESCRIPTION OF EMBODIMENTS

Figure 1:
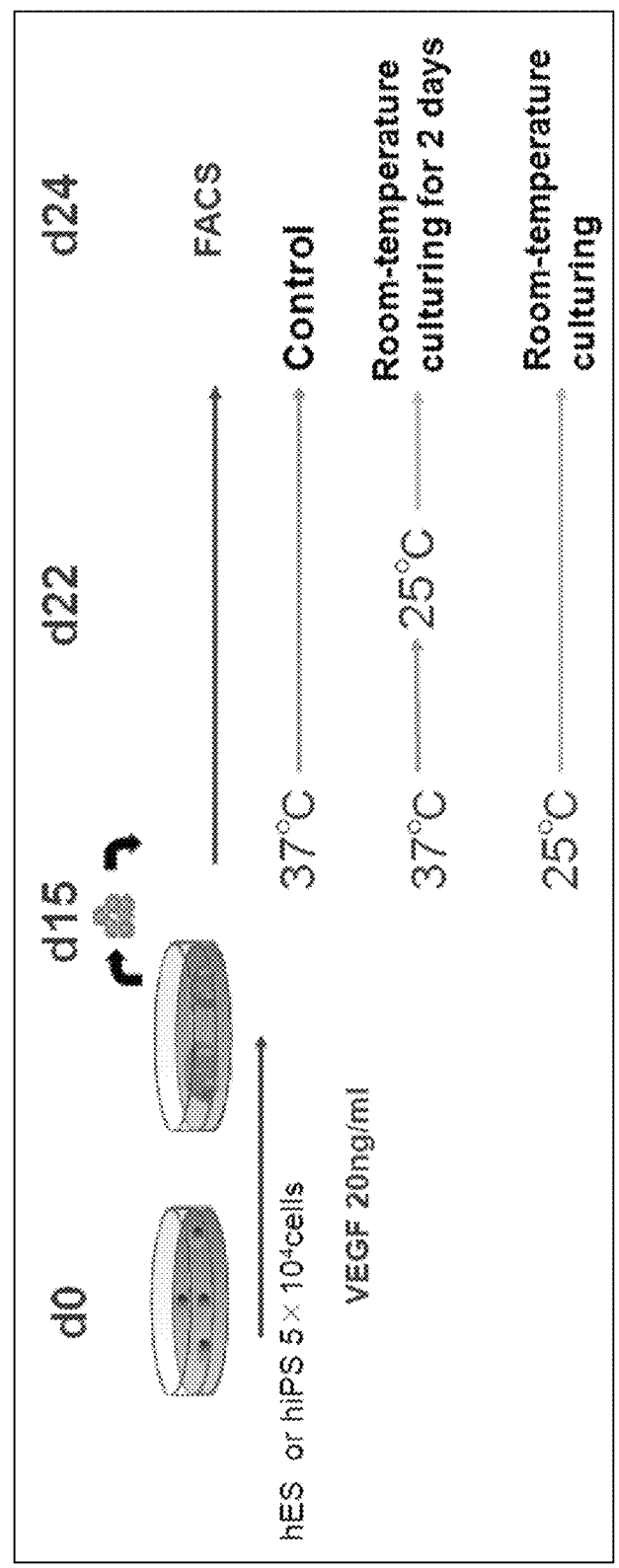

A composition of the present invention is a composition for maintaining a function of platelets, the composition comprising, as an active ingredient, a compound represented by the following general formula (I) or a salt thereof, or a solvate thereof:

[Chem. 11]

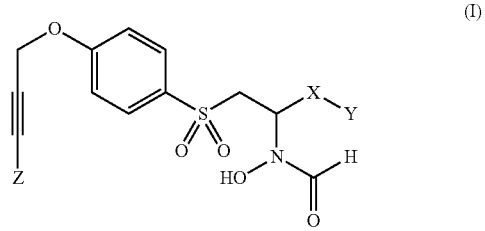

(I)

wherein
X represents a phenylene group;
Y represents any one of a hydrogen atom and —$(CH_2)_m R^1$;
wherein
m represents an integer of any one of 0 to 4; and
$R^1$ is any one of

[Chem. 12]

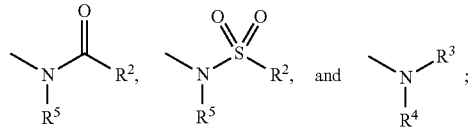

wherein $R^2$ represents any one of a C1 to C6 alkyl group, which may be substituted, an aryl group, which may be substituted, and a C1 to C6 alkoxy group;
$R^3$ and $R^4$ each independently represent any one of a hydrogen atom and a C1 to C6 alkyl group, or $R^3$ and $R^4$ together with an adjacent nitrogen atom may form a nitrogen-containing heterocycle; and
$R^5$ represents any one of a hydrogen atom, a C1 to C6 alkyl group, and a C1 to C6 alkylsulfonyl group; and
Z represents any one of a hydrogen atom and a C1 to C6 alkyl group.

In the compound represented by the above-mentioned general formula (I), "C1 to C6" and "C6 to C14" each mean that the carbon number falls within a range of from 1 to 6, and from 6 to 14, respectively.

"C1 to C6 alkyl group" of "C1 to C6 alkyl group, which may be substituted" in $R^2$, $R^3$, $R^4$, $R^5$ and Z means a linear or branched C1 to C6 alkyl group, and its specific examples include a methyl group, an ethyl group, an n-propyl group, an isopropyl group, an n-butyl group, an isobutyl group, a tert-butyl group, a sec-butyl group, an n-pentyl group, a tert-amyl group, a 3-methylbutyl group, a neopentyl group, an n-hexyl group, etc.

The substituent in the above-mentioned "C1 to C6 alkyl group, which may be substituted" includes a hydroxyl group, a halogen atom, a cyano group, a nitro group, a C1 to C6 alkoxy group, a carboxyl group, a C1 to C6 alkoxycarbonyl group, etc. At least one or more of these may be substituted in any and every substitutable position. In case where the compound has multiple substituents, the substituents may be the same or different, and may be substituted on the same carbon atom or on different carbon atoms.

"Halogen atom" means a fluorine atom, a chlorine atom, a bromine atom, an iodine atom.

"C1 to C6 alkoxy group" means an alkoxy group in which the alkyl moiety is has the same meaning as that of the above-mentioned "C1 to C6 alkyl group", for which, for example, there is mentioned a linear or branched alkoxy group such as a methoxy group, an ethoxy group, an n-propoxy group, an isopropoxy group, an n-butoxy group, an isobutoxy group, a tert-butoxy group, a sec-butoxy group, an n-pentyloxy group, a tert-amyloxy group, a 3-methylbutoxy group, a neopentyloxy group, an n-hexyloxy group, etc.

"C1 to C6 alkoxycarbonyl group" means one in which the alkyl moiety excluding the oxycarbonyl moiety therein is a linear or branched C1 to C6 alkyl group, including, for example, a methoxycarbonyl group, an ethoxycarbonyl group, an n-propoxycarbonyl group, an isopropoxycarbonyl group, an n-butoxycarbonyl group, an isobutoxycarbonyl group, a tert-butoxycarbonyl group, a sec-butoxycarbonyl group, an n-pentyloxycarbonyl group, a tert-amyloxycarbonyl group, a 3-methylbutoxycarbonyl group, a neopentyloxycarbonyl group, an n-hexyloxycarbonyl group, etc.

"Nitrogen-containing heterocycle" which $R^3$ and $R^4$ together with an adjacent nitrogen atom form includes, for example, a 5- to 7-membered nitrogen-containing heterocycle which contains at least one nitrogen atom in addition to the carbon atom as the cycle-constituting atom and may further contain one or two hetero atoms selected from an oxygen atom, a sulfur atom and a nitrogen atom. Preferred examples of the nitrogen-containing heterocycle include a piperidine ring, a piperazine ring, a morpholine ring, a thiomorpholine ring, a pyrrolidine ring, an imidazolidine ring, etc.

"Aryl group" of "aryl group, which may be substituted" in $R^2$ means an aromatic carbocycle, preferably a C6 to C14 aromatic carbocycle, and includes, for example, a phenyl group, a naphthyl group, etc.

The substituent on the aromatic ring of the above-mentioned "aryl group, which may be substituted" includes a hydroxyl group, a halogen atom, a cyano group, a nitro group, a trifluoromethyl group, a C1 to C6 alkyl group which may be substituted, a C1 to C6 alkoxy group, a carboxyl group, a C1 to C6 alkoxycarbonyl group, etc. At least one or more of these may be substituted in any and every substitutable position. In case where the compound has multiple substituents, the substituents may be the same or different, and may be substituted on the same carbon atom or on different carbon atoms. In this, "halogen atom", "C1 to C6 alkyl group, which may be substituted", "C1 to C6 alkoxy group" and "C1 to C6 alkoxycarbonyl group" have the same meanings as above.

"C1 to C6 alkylsulfonyl group" in $R^5$ means an alkylsulfonyl group in which the alkyl moiety has the same meaning as that of the above-mentioned "C1 to C6 alkyl group", including, for example, a methanesulfonyl group, an ethanesulfonyl group, etc.

In case where the compound represented by the general formula (I) has an asymmetric carbon, racemates and diastereomers thereof and also individual optical active forms of the compound are all included in the invention. In case where the compound has a geometric isomer, the (E) form and the (Z) form thereof and also the mixture thereof are all included in the invention.

Not specifically defined, the salt of the compound represented by the general formula (I) may be any pharmaceutically-acceptable salt thereof, including, for example, salts with an inorganic base, salts with an organic base, salts with an organic acid, salts with an inorganic acid, salts with an amino acid, etc. Examples of the salts with an inorganic base include alkali metal salts and alkaline earth metal salts such as lithium salts, sodium salts, potassium salts, calcium salts, magnesium salts, etc. Examples of the salts with an organic base include triethylamine salts, pyridine salts, ethanolamine salts, cyclohexylamine salts, dicyclohexylamine salts, dibenzylethanolamine salts, etc. Examples of the salts with an organic acid include formates, acetates, tartrates, maleates, succinates, lactates, malates, ascorbates, oxalates, glycolates, phenylacetates, methanesulfonates, etc. Examples of the salts with an inorganic acid include hydrochlorides, hydrobromides, phosphates, sulfamates, nitrates, etc. Examples of the salts with an amino acid include glycine salts, alanine salts, arginine salts, glutamates, aspartates, etc.

The compound represented by the general formula (I) may have a form of prodrug. Examples of prodrug include methyl ester, ethyl ester and aminoalkyl ester derivatives at the carboxyl group of the compound of the general formula (I), acetate, formate and benzoate derivatives at the hydroxyl group and the amine functional group of the compound of the general formula (I), etc., to which, however, the invention is not limited.

The compound represented by the above-mentioned general formula (I) can be produced according to various methods but may be efficiently produced according to the method mentioned below. Note that, Specific examples of the "protective group" for use in the production method mentioned below include a tert-butyl group, a benzyl group, an o-methylbenzyl group, a p-nitrobenzyl group, a p-methoxybenzyl group, an o-chlorobenzyl group, a 2,4-dichlorobenzyl group, a p-bromobenzyl group, an allyl group, a tert-butoxycarbonyl group, a benzyloxycarbonyl group, an o-methylbenzyloxycarbonyl group, a p-nitrobenzyloxycarbonyl group, a p-methoxybenyloxycarbonyl group, an o-chlorobenzyloxycarbonyl group, a 2,4-dichlorobenzyloxycarbonyl group, a p-bromobenzyloxycarbonyl group, an allyloxycarbonyl group, a tert-butyldimethylsilyl group, a tert-butyldiphenylsilyl group, a triethylsilyl group, a trimethylsilyl group, a triisopropylsilyl group, a methoxymethyl group, a tetrahydropyranyl group, carbonyl protective groups (for example, protective groups with ethanediol, propanediol, mercaptoethanol, mercaptopropanol, ethanedithiol, propanedithiol, etc.), etc.

The compound represented by the general formula (I) can be produced, for example, through the reaction of the following step 1 and step 2.

Scheme 1:

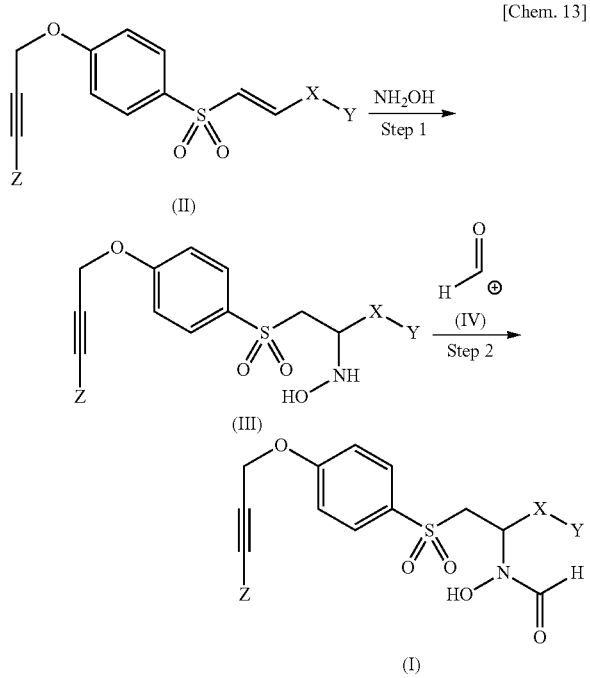

[Chem. 13]

(In the formulae, X, Y and Z have the same meanings as mentioned above.)

<Step 1>

In the step 1, hydroxylamine or its salt is added to the compound (II) to produce the compound represented by the general formula (III). In case where hydroxylamine is a salt thereof (hydrochloride, acetate, etc.), the addition reaction is attained in the presence of an inorganic base such as potassium carbonate, sodium carbonate, sodium hydrogen carbonate, sodium hydroxide, potassium hydroxide, lithium hydroxide, etc. Not specifically defined, the reaction solvent may be any solvent not significantly interfering with the reaction, but is preferably water, tetrahydrofuran, cyclopentyl methyl ether, acetonitrile, 1,4-dioxane, diethyl ether or their mixed solvent, etc.

Not specifically defined, the reaction temperature may be generally from 0 to 100° C., and the reaction time is preferably from 2 hours to 1 week.

<Step 2>

In the step 2, the compound (III) obtained in the step 1 is condensed with the intermediate represented by the general formula (IV) to produce the compound represented by the general formula (I). The intermediate (IV) is a reactive intermediate to be obtained from a mixed acid anhydride with formic acid (mixed acid anhydride of formic acid and acetic acid, etc.), pentafluorophenyl formate, or formic acid and a carbodiimide (dicyclohexylcarbodiimide, diisopropylcarbodiimide or water-soluble carbodiimide). For smoothly attaining the reaction, an organic base such as triethylamine, diisopropylethylamine, pyridine, lutidine, collidine, dimethylaminopyridine or the like may be made to coexist in the system. Adding 1-hydroxybenzotriazole and/or 4-dimethylaminopyridine to some of these cases (especially where the reactive intermediate is obtained from carbodiimide) could promote the reaction. Not specifically defined, the reaction solvent may be any solvent not significantly interfering with the reaction, but is preferably chloroform, methylene chloride, tetrahydrofuran, acetonitrile, cyclopentyl methyl ether, 1,4-dioxane, dimethylformamide, dimethyl sulfoxide, pyridine, etc. Not specifically defined, the reaction temperature may be generally from 0 to 100° C., and the reaction time is preferably from 1 to 24 hours. In this step, a CHO group may be added to also to the hydroxyl group of the hydroxylamino group, depending on the chemical properties of the starting materials; but in such a case, the product may be processed with a lower alcohol in an acidic, basic or neutral condition to be converted into the intended product, compound (I). The lower alcohol is preferably methanol, ethanol, propanol, etc. An auxiliary solvent may be used here, and when used, the auxiliary solvent is not specifically defined.

Needless to say, depending on the properties of X, Y and Z, it is necessary to previously use the corresponding protective group in the reaction of the above-mentioned step 1 and step 2 and to remove the protective group after the reaction. In case where the group is not protected, the yield in the next step and further in the next step after that next step may lower and the intermediate may be difficult to handle.

The above-mentioned compound (II) may be produced according to the process of the step 3 to step 5, as mentioned below.

Scheme 2:

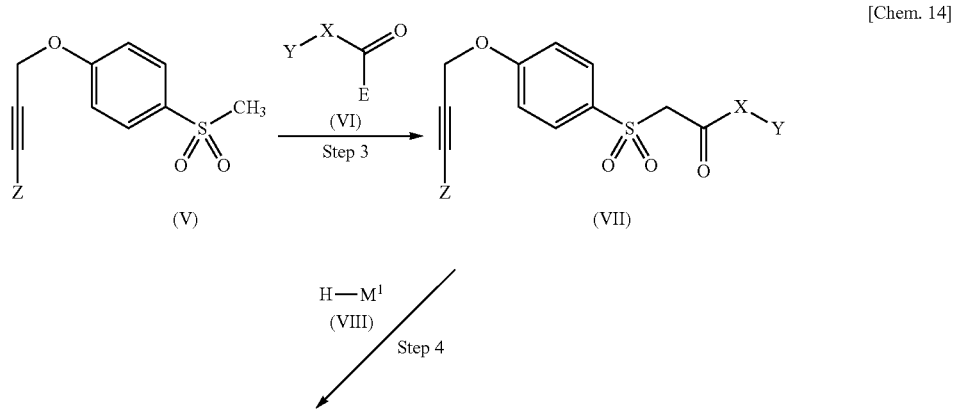

[Chem. 14]

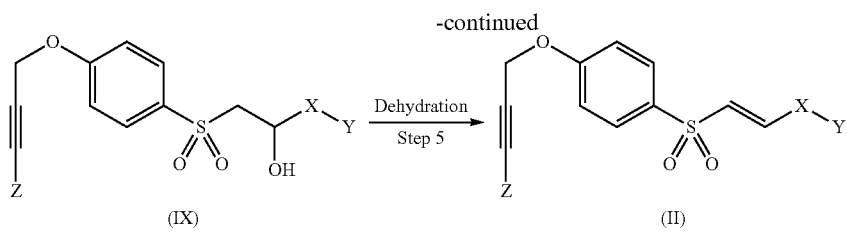

(In the formulae, X, Y and Z have the same meanings as above; E represents a releasing functional group such as a C1 to C6 alkoxy group, a halogen atom, an N,O-dimethylhydroxyamino group or the like; $M^1$ represents Li, $CeCl_2$, $NaBH_3$, $LiBH_3$, $LiBEt_3$, $KBEt_3$, $LiB[CH(CH_3)C_2H_5]_3$, $KB[CH(CH_3)C_2H_5]_3$, $Al[CH(CH_3)C_2H_5]_2$ or the like; Et represents an ethyl group.)

<Step 3>

In the step 3, the compound represented by the general formula (V) is converted into an anion with a base, and then reacted with the compound represented by the general formula (VI) to produce the compound (VII). The base to be used includes lithium diisopropylamide, lithium(bistrimethylsilyl)amide, lithium tetramethylpiperazide, sodium(bistrimethylsilyl)amide, potassium(bistrimethylsilyl)amide, n-butyllithium, sec-butyllithium, tert-butyllithium, etc. One alone or, as the case may be, two or more of these may be used either singly or as combined. Not specifically defined, the reaction solvent may be any one not significantly interfering with the reaction, but is preferably tetrahydrofuran, cyclopentyl methyl ether, tetrahydrofuran, diethyl ether, tert-butyl methyl ether, or their mixed solvent, etc.

The reaction temperature may be generally from −100 to 40° C. and the reaction time is preferably from 1 to 12 hours. In this step, the compound (II) may be produced depending on the chemical properties of the compound (VI), which, however, causes no problem in consideration of the intended production object.

<Step 4>

In the step 4, the compound (VII) obtained in the step 3 is reacted with the compound represented by the general formula (VIII) to produce the compound represented by the general formula (IX). The reaction solvent is, when the compound (VIII) is sodium borohydride or lithium borohydride, preferably methanol, ethanol, isopropanol, tetrahydrofuran, cyclopentyl methyl ether, dichloromethane, chloroform or their mixture, etc.; but when the compound (VIII) is any other than those two, the reaction solvent is preferably tetrahydrofuran, cyclopentyl methyl ether, tetrahydropyran, diethyl ether, tert-butyl methyl ether or their mixed solvent, etc. The reaction temperature may be generally from −100 to 30° C. and the reaction time is preferably from 1 to 12 hours.

During or after the reaction of the step 4, the hydroxyl group may be spontaneously eliminated from the formed compound (IX) whereby the compound may be partly or wholly converted into the compound (II). In the case of partial conversion, the step 5 may be carried out without separating the converted compound; and in the case of complete conversion, the step 5 may be omitted.

<Step 5>

In the step 5, the compound (IX) obtained in the step 4 may be dehydrated to produce the compound (II). The dehydration reaction is attained by a combination of a hydroxyl group activator and an organic base. The hydroxyl group activator includes methanesulfonyl chloride, p-toluenesulfonyl chloride, benzenesulfonyl chloride, methanesulfonyl chloride, thionyl chloride, surfuryl chloride, phosphorus pentachloride, etc. The organic base includes triethylamine, diisopropylethylamine, diazabicycloundecene, diazabicyclononene, pyridine, dimethylaminopyridine, lutidine, collidine, etc. Preferred is a combination of methanesulfonyl chloride and triethylamine. As other dehydration reagents, there may be mentioned triphenylphosphine-diethyl azodicarboxylate, triphenylphosphine-diisopropyl azocarboxylate, tri-n-butylphosphine-diethyl azodicarboxylate, tri-n-butylphosphine-diisopropyl azocarboxylate, etc. The reaction solvent may be any one not significantly interfering with the reaction, but is preferably chloroform, methylene chloride, tetrahydrofuran, cyclopentyl methyl ether, acetonitrile, 1,4-dioxane, dimethyl formamide, etc. Not specifically defined, the reaction temperature may be generally from 0 to 100° C., and the reaction time is preferably from 1 to 24 hours.

Needless to say, depending on the properties of X, Y and Z, it is necessary to previously use the corresponding protective group in the reaction of the above-mentioned step 3 to step 5 and to remove the protective group after the reaction.

The compound (V) may be produced according to the step 6 mentioned below.

Scheme 3:

[Chem. 15]

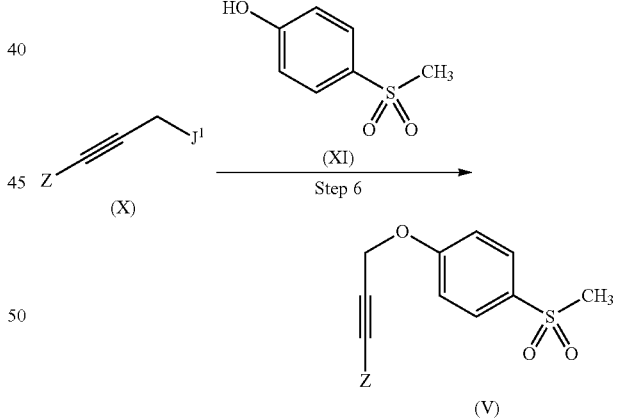

(In the formulae, Z had the same meaning as above; represents a halogen atom, a methanesulfonyloxy group, a p-toluenesulfonyloxy group, a benzenesulfonyloxy group, a trifluoromethanesulfonyloxy group or a hydroxyl group.)

<Step 6>

In the step 6, the compound represented by the general formula (X) or its salt is condensed with the compound represented by the general formula (XI) in the presence of an inorganic base to produce the compound (V). Preferred inorganic bases include sodium hydroxide, potassium hydroxide, lithium hydroxide, sodium carbonate, potassium carbonate, cesium carbonate, calcium carbonate, etc. However, when $J^1$ is a hydroxyl group, the hydroxyl group of the compound represented by the general formula (X) or its salt is activated with a reagent and then the resulting compound is condensed with the compound represented by the general formula (XI) to produce the compound (V). As the reagent suitable for activating the hydroxyl group, there may be mentioned diethyl azodicarboxylate (DEAD)-triphenylphosphine, diisopropyl azodicarboxylate-triphenylphosphine, cyanomethylene tributylphosphorane, cyanomethylene trimethylphosphorane, butyllithium-chlorodiphenylphosphine, etc. In case of activating the group with butyllithium-chlorodiphenylphosphine, a quinone compound such as 2,6-dimethyl-1,4-benzoquinone, tetrafluoro-1,4-benzoquinone or the like is added to the system.

Not specifically defined, the reaction solvent may be any one not significantly interfering with the reaction, but is preferably water, methanol, ethanol, tert-butanol, tetrahydrofuran, cyclopentyl methyl ether, acetonitrile, diethyl ether, dimethyl ether, dichloromethane, 1,4-dioxane, 2-methoxyethanol, N,N-dimethylformamide, or their mixed solvent, etc. Not specifically defined, the reaction temperature may be generally from −80 to 120° C., and the reaction time is preferably from 1 to 24 hours.

The above-mentioned compound (II) may also be produced through the reaction of the following step 7 to step 11, as mentioned below.

Scheme 4:

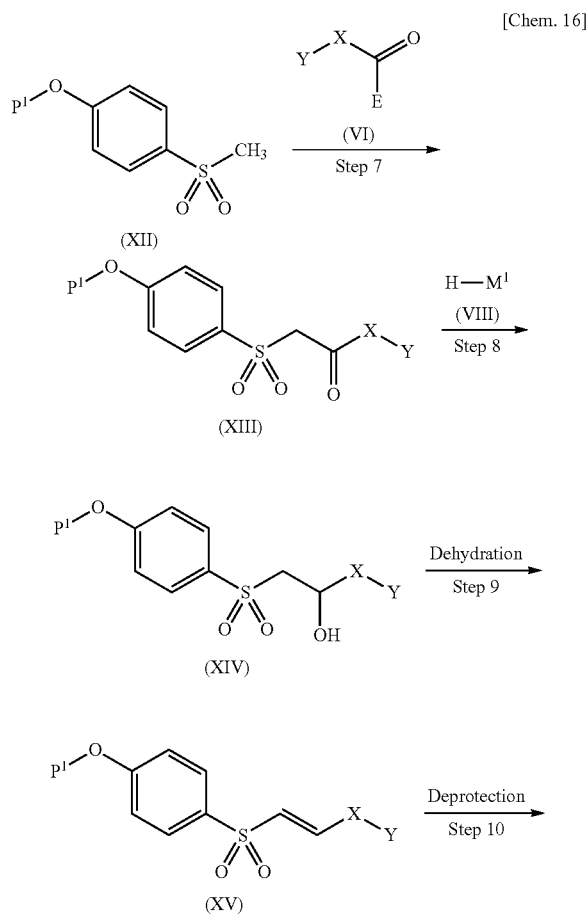

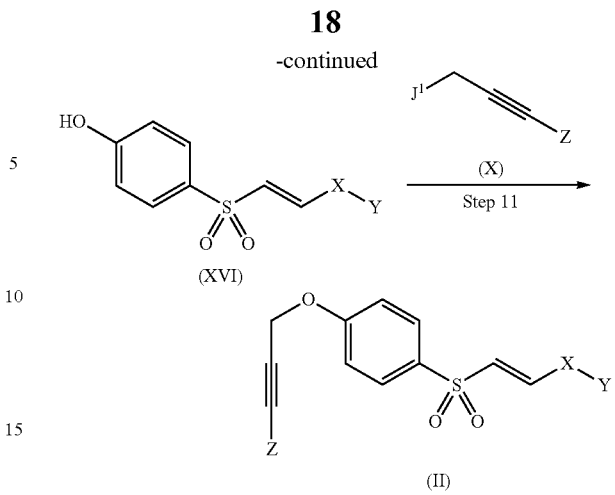

(In the formulae, X, Y, Z, E, $M^1$ and $J^1$ are the same as mentioned above; and $P^1$ represents a hydroxyl-protective group.)

<Step 7>

In the step 7, the compound represented by the general formula (XII) is converted into an anion with a base, and then reacted with the compound (VI) to produce the compound (XIII), like in the step 3.

<Step 8>

In the step 8, the compound represented by the general formula (XIII) is reacted with the compound represented by the general formula (VIII) to produce the compound (XIV), like in the step 4.

Needless to say, depending on the properties of X and Y, it is necessary to previously use the corresponding protective group in the reaction of the above-mentioned step 7 and step 8 and to remove the protective group after the reaction.

<Step 9>

In the step 9, the compound (XIV) is dehydrated to produce the compound (XV), like in the step 5.

In the step 9, the protective group $P^1$ may be spontaneously removed from the formed compound whereby the compound may be partly or wholly converted into the compound (XVI). In the case of partial conversion, the step 10 may be carried out without separating the converted compound; and in the case of complete conversion, the step 10 may be omitted.

<Step 10>

In the step 10, the compound represented by the general formula (XV) is deprotected according to any known method depending on the type of the protective group $P^1$ therein, thereby producing the compound represented by the general formula (XVI).

<Step 11>

In the step 11, the compound (XVI) is condensed with the compound represented by the general formula (X) or its salt to produce the compound (II), like in the step 6.

The N-hydroxyformamide derivative of the invention, thus produced according to the above-mentioned method, may be isolated and purified as a free compound thereof, or as its salt, its hydrate or its various types of solvates such as an ethanolate thereof, or as a polymorphic form thereof. The pharmaceutically-acceptable salt of the compound of the general formula (I) can be produced according to conventional salt-forming reaction. The isolation and purification may be attained by chemical operation of extractive fractionation, crystallization, various types of fractionation chromatography, etc. An optical isomer may be obtained as stereochemically pure isomer by selecting suitable starting materials or by optical resolution of racemic compounds.

The composition of the present invention is a composition for maintaining a function of platelets, the composition comprising, as an active ingredient, the above-described compound or a salt thereof, or a solvate thereof (hereinafter also referred to as "the compound represented by the general formula (I) or the like"). In the present invention, the phrase "maintaining a function of platelets" mainly means maintaining a function related to blood coagulation such as hemostasis and thrombus formation by platelets. The composition of the present invention is capable of achieving the function by suppressing ADAM17-mediated GPIbα shedding (release by cleavage).

"Maintaining a function of platelets" can be evaluated, for example, by employing a method in which the adhesion ability of platelets to VWF is evaluated using a flow chamber system as described in International Publication No. WO2009/119105 and Test Example 15 described later, a method in which the in vivo lifespan of platelets is evaluated using thrombocytopenic mouse, a method in which the shape of platelets is observed on a fibrinogen-coated cover glass in the presence of thrombin, a biomolecular imaging technique as described in Test Example 16 later in which a thrombus formation model animal is prepared using laser irradiation together with hematoporphyrin and so forth to observe the kinetics of platelets at an individual level in the model animal, or other approaches.

ADAM17 (a disintegrin and metallopeptidase domain 17) is a protein having a structure containing a disintegrin domain and has a metalloproteinase activity. ADAM17 is a protein also called TACE (TNF-alpha converting enzyme) because ADAM17 sheds, other than GPIbα, membrane-bound TNF-α (tumor necrosis factor-alpha) to produce free TNF-α. Typically, human-derived ADAM17 is a protein (gene) specified under ACCESSION No. NP_003174.3 (No. NM_003183.4).

GPIbα (glycoprotein Ib alpha) is a membrane protein of platelets, and functions as a receptor for von Willebrand factor (VWF). In addition, since GPIbα is expressed only on platelets in a human body, GPIbα is also called CD42b antigen and used as a surface marker for platelets. Typically, human-derived GPIbα is a protein (gene) specified under ACCESSION No. NP_000164.5 (No. NM_000173.5).

Although reference sequences registered in GenBank are exemplified as typical examples of ADAM17 and GPIbα, the amino acid sequences of the proteins may be mutated naturally (i.e., non-artificially). Thus, it should be understood that ADAM17 and GPIbα involved in the action mechanism of the composition of the present invention include such naturally-occurring mutants.

In the present invention, the phrase "suppressing ADAM17-mediated GPIbα shedding" includes both complete suppression (inhibition) and partial suppression of shedding by ADAM17. Further, as described in Examples later, it is possible to evaluate the composition of the present invention as suppressing ADAM17-mediated GPIbα shedding when a percentage of the number of CD42b (GPIbα)(+) platelets to a total number of platelets in the presence of the composition of the present invention is calculated to be a large value in comparison with a percentage obtained in the absence of the composition of the present invention. As the degree of GPIbα shedding suppressed by the composition of the present invention, the percentage of the number of CD42b (+) platelets in the presence of the composition of the present invention is preferably 80% or higher, and a higher percentage is more preferable (for example, 85% or higher, 90% or higher, 95% or higher).

Note that when an ability of the composition of the present invention to suppress GPIbα shedding is evaluated using a method described in Test Example 3 later, the 50% inhibitory concentration ($IC_{50}$) is preferably 0.01 nmol/L to 100 nmol/L.

Examples of the compound represented by the general formula (I) as an active ingredient of the composition of the present invention include N-[2-(4-but-2-ynyloxybenzenesulfonyl)-1-(4-diethylaminomethylphenyl)ethyl]-N-hydroxyformamide, N-[2-(4-but-2-ynyloxybenzenesulfonyl)-1-(4-dimethylaminomethylphenyl)ethyl]-N-hydroxyformamide, N-{4-[2-(4-but-2-ynyloxybenzenesulfonyl)-1-(formylhydroxyamino)ethyl]benzyl}-2-methoxyacetamide, N-{4-[2-(4-but-2-ynyloxybenzenesulfonyl)-1-(formylhydroxyamino)ethyl]benzyl}methanesulfonamide, N-{4-[2-(4-but-2-ynyloxybenzenesulfonyl)-1-(formylhydroxy-amino)ethyl]benzyl}benzamide, N-[2-(4-but-2-ynyloxybenzenesulfonyl)-1-(4-morpholin-4-ylmethylphenyl)ethyl]-N-hydroxyformamide, N-hydroxy-N-[1-(4-morpholin-4-ylmethylphenyl)-2-(4-pent-2-ynyloxybenzenesulfonyl)ethyl]formamide, N-[2-(4-but-2-ynyloxybenzenesulfonyl)-1-(4-dimethylaminophenyl)ethyl]-N-hydroxyformamide, N-[2-(4-but-2-ynyloxybenzenesulfonyl)-1-(3-dimethylaminophenyl)ethyl]-N-hydroxyformamide, N-[2-(4-but-2-ynyloxybenzenesulfonyl)-1-(2-dimethylaminophenyl)ethyl]-N-hydroxyformamide, N-[2-(4-but-2-ynyloxybenzenesulfonyl)-1-(4-piperidin-1-ylmethylphenyl)ethyl]-N-hydroxyformamide, N-[2-(4-but-2-ynyloxybenzenesulfonyl)-1-(3-piperidin-1-ylmethylphenyl)ethyl]hydroxyformamide, N-[2-(4-but-2-ynyloxybenzenesulfonyl)-1-(3-morpholin-4-ylmethylphenyl)ethyl]-N-hydroxyformamide, N-[2-(4-but-2-ynyloxybenzenesulfonyl)-1-{4-[(ethylmethylamino)methyl]phenyl]ethyl}-N-hydroxyformamide, N-(2-(4-but-2-ynyloxybenzenesulfonyl)-1-{3-[(ethylmethylamino)methyl]phenyl}ethyl)-N-hydroxyformamide, N-{4-[2-(4-but-2-ynyloxybenzenesulfonyl)-1-(formylhydroxyamino)ethyl]benzyl}-N-methylmethanesulfonamide, N-{4-[2-(4-but-2-ynyloxybenzenesulfonyl)-1-(formylhydroxyamino)ethyl]benzyl}-4-methylbenzenesulfonamide, N-{4-[2-(4-but-2-ynyloxybenzenesulfonyl)-1-(formylhydroxyamino)ethyl]benzyl}-4,N-dimethylbenzenesulfonamide, N-{4-[2-(4-but-2-ynyloxybenzenesulfonyl)-1-(formylhydroxyamino)ethyl]benzyl}-N-methylsulfonylmethanesulfonamide, N-{2-(4-but-2-ynyloxybenzenesulfonyl)-1-[4-(2-dimethylaminoethyl)phenyl]ethyl}-N-hydroxyformamide, N-{2-(4-but-2-ynyloxybenzenesulfonyl)-1-[4-(2-morpholin-4-ylethyl)phenyl]ethyl}-N-hydroxyformamide, N-(2-{4-[2-(4-but-2-ynyloxybenzenesulfonyl)-1-(formylhydroxyamino)ethyl]phenyl}ethyl)methanesulfonamide, N-{2-(4-but-2-ynyloxybenzenesulfonyl)-1-[4-(3-dimethylaminopropyl)phenyl]ethyl}-N-hydroxyformamide, N-{2-(4-but-2-ynyloxybenzenesulfonyl)-1-[4-(3-diethylaminopropyl)phenyl]ethyl}-N-hydroxyformamide, N-{2-(4-but-2-ynyloxybenzenesulfonyl)-1-[4-(3-morpholin-4-ylpropyl)phenyl]ethyl}-N-hydroxyformamide, N-{2-(4-but-2-ynyloxybenzenesulfonyl)-1-[4-(4-morpholin-4-ylbutyl)-phenyl]-ethyl}-N-hydroxyformamide, N-{4-[1-(formylhydroxyamino)-2-(4-pent-2-ynyloxybenzenesulfonyl)ethyl]benzyl}methanesulfonamide, and N-{4-[1-(formylhydroxyamino)-2-(4-oct-2-ynyloxybenzenesulfonyl)ethyl]benzyl}methanesulfonamide. As described in Test Example 4 later, from the viewpoint of having a high specificity to ADAM17, N-[2-(4-but-2-ynyloxybenzenesulfonyl)-1-(4-diethylaminomethylphenyl)ethyl]-N-hydroxyformamide or N-{4-[2-(4-but-2-ynyloxybenzenesulfonyl)-1-(formylhydroxyamino)ethyl]benzyl}methanesulfonamide is preferable.

Note that N-[2-(4-but-2-ynyloxybenzenesulfonyl)-1-(4-diethylaminomethylphenyl)ethyl]-N-hydroxyformamide is "I-1" or "S-45282" in Examples described later, and N-{4-[2-(4-but-2-ynyloxybenzenesulfonyl)-1-(formylhydroxyamino)ethyl]benzyl}methanesulfonamide is "I-4" or "S-45457" in Examples described later.

Examples of the form of the composition of the present invention include a drug additive and a reagent used for purposes of research and development (for example, in vitro and in vivo research and development).

The composition of the present invention has an action of maintaining a function of platelets by suppressing ADAM17-mediated GPIbα shedding. Accordingly, the composition of the present invention can be suitably used as a reagent for maintaining a function of platelets (for example, a reagent used in a culture system for differentiating megakaryocytes from cells capable of differentiating into megakaryocytes and then producing platelets from the megakaryocytes, or a reagent for maintaining a function of produced platelets by adding the regent) or as a drug additive added to a blood product comprising platelets from donation and the like. When used as the above-described additive or reagents, the composition of the present invention may comprise, for example, a stabilizer, a solvent, or the like, in addition to the compound represented by the general formula (I) or the like as the active ingredient.

A product (for example, reagent, drug additive) of the composition of the present invention or a protocol thereof may be labelled to indicate that the use is to maintain a function of platelets. Herein, the phrase "a product or a protocol is labelled" means that the body of the product, a container or a package therefore, or the like is labelled, or that a protocol, an attachment document, an advertisement, other prints, or the like disclosing information on the product is labelled. The label indicating that the use is to maintain a function of platelets may include information on a mechanism of how the compound represented by the general formula (I) or the like as the active ingredient of the composition of the present invention demonstrates an effect of maintaining a function of platelets. An example of the information on the mechanism includes information that a function of platelets is maintained by suppressing ADAM17-mediated GPIbα shedding. Moreover, the label indicating that the use is to maintain a function of platelets may include information that the use is to produce or store platelets or for other purposes.

The compound represented by the general formula (I) or the like serves as an active ingredient for manufacturing the composition of the present invention. Thus, the present invention also provides: the use of the compound represented by the general formula (I) or the like for manufacturing the composition of the present invention; and a method for manufacturing the composition of the present invention comprising the compound represented by the general formula (I) or the like.

Further, the present invention provides a culture which is a culture system for differentiating megakaryocytes from cells capable of differentiating into megakaryocytes and for producing platelets from the megakaryocytes, and is added to the system with the compound represented by the general formula (I) or the like. Furthermore, the present invention provides a method for preparing platelets, wherein the method comprises adding, to a culture system for differentiating megakaryocytes from cells capable of differentiating into megakaryocytes and producing platelets from the megakaryocytes, the compound represented by the general formula (I) or the like.

In the present invention, "megakaryocytes" are cells also called platelet progenitor cells or megakaryocytic cells, and they divide the cytoplasm to produce platelets.

In the present invention, "cells capable of differentiating into megakaryocytes" are not particularly limited, as long as the cells are capable of differentiating into megakaryocytes. Examples thereof include fertilized eggs, pluripotent stem cells such as embryonic stem cells (ES cells), induced pluripotent stem cells (iPS cells), embryonic germ cells (EG cells), hematopoietic stem cells, hematopoietic progenitor cells, megakaryoblasts, and adipocytes. The hematopoietic stem cells and the hematopoietic progenitor cells may be collected from bone marrow, umbilical cord blood, or the like. Further, among these, iPS cells are preferable from the viewpoints that there is no ethical problem because an embryo is not destroyed, and that it is easy to match the human leukocyte antigen (HLA) type of a patient transfused with platelets prepared according to the present invention. Moreover, iPS cells established using 4 factors (Oct3/4, Sox2, Klf4 and c-Myc) are more preferable from the viewpoints that megakaryocytes derived from the iPS cells can continue to increase until Days 25 to 35 after culturing of the iPS cells is started, and that the number of platelets produced from the megakaryocytes is 2 to 10 times larger than the number of platelets from iPS cells established using 3 factors (Oct3/4, Sox2 and Klf4). Note that the present inventors have confirmed that such increase in the number of megakaryocytes and platelets produced are caused by re-activation of the c-Myc gene.

Further, an animal species from which the above-described cells used in the method of the present invention are derived is not particularly limited. Examples thereof include human, mice, rats, dogs, cats, cattle, horses, sheep, and the like. Preferable are mice, rats, and human, more preferable are mice and human, and particularly preferable is human.

Examples of the "culture system for differentiating megakaryocytes from cells capable of differentiating into megakaryocytes and producing platelets from the megakaryocytes" in the present invention include a culture system for forming embryoid bodies (cell population containing differentiation-induced, undifferentiated mesodermal cells) in the middle of platelet production (Eto et al., Proc. Natl. Acad. Sci. USA, 2002, vol. 99, pp. 12819-12824, and so forth), a culture system for forming a sac-like structure (sac structure) enclosing hematopoietic progenitor cells (see PTLs 1 to 3 and so forth), a culture system for producing platelets from umbilical cord blood-derived hematopoietic progenitor cells (see Robert et al., "Glycoprotein Ibalpha receptor instability is associated with loss of quality of platelets produced in culture.", Stem Cells and Development, published online on May 26, 2010, and so forth), and the like (for others, see Fujimoto et al., Blood, 2003, vol. 102, pp. 4044-4051: Hiroyama et al., Exp. Hematol., 2006, vol. 34, pp. 760-769: Gaur et al., J Thromb Haemost., 2005, vol. 4, pp. 436-442; and so forth). Among these, a culture system for forming a sac-like structure is preferable because hematopoietic progenitor cells are condensed in the sac-like structure, enabling efficient ex vivo production of megakaryocytes, platelets, and the like.

Culture conditions of the culture system according to the present invention are not particularly limited, as long as the conditions are suitable for culturing of megakaryocytes and platelet production. The culture temperature is preferably 35 to 38° C., more preferably 37° C. If the culture temperature is below the lower limit, the numbers of megakaryocytes and platelets produced tend to be small. If the culture temperature exceeds the upper limit, cell culturing and maintenance tend to be difficult.

Furthermore, when the "cells capable of differentiating into megakaryocytes" according to the present invention are cultured (particularly, in the process of inducing differentiation to megakaryocytes), the cells are preferably co-cultured with feeder cells. The "feeder cells" used herein are not particularly limited, as long as the feeder cells contribute to the differentiation induction of the "cells capable of differentiating into megakaryocytes." For example, it is possible to use mouse embryonic fibroblasts, preferably a 10T1/2 cell line, OP9 cells, and the like. An example of the cells other than immortalized cell lines includes human bone marrow-derived mesenchymal stem cells (cultured cells directly prepared from human bone marrow). Even when the mesenchymal stem cells are used as the feeder cells, megakaryocyte maturation and platelet production from human ES cells or iPS cells are possible. Platelets can be induced by culturing on an extracellular substrate such as Matrigel also, but the efficiency is low. When the "feeder cells" are used, it is preferable to suppress the growth of cells through radiation exposure or the like.

An amount (concentration) of the compound represented by the general formula (I) or the like added to the culture system is preferably 0.01 to 100 μM. If the amount added is below the lower limit, it tends to be difficult to suppress the GPIbα cleavage on platelets. If the amount exceeds the upper limit, cell growth tends to be suppressed. Additionally, the adding period of the compound represented by the general formula (I) or the like to the culture system is preferably throughout the entire production period from hematopoietic progenitor cells to platelets, from the viewpoints of ensuring uniformity during the culture process and ensuring product uniformity, regardless of non-uniform situation for blood cell differentiation. This is greatly different from adding period of GM6001 which is limited to a production period from megakaryocytes to platelets.

Hereinafter, the method for preparing platelets of the present invention will be more specifically described by taking an example of a method for forming a sac-like structure suitably used for the culture system of the present invention.

First, description will be given of the method for forming a sac-like structure (sac structure). Culture conditions suitable for preparing a sac-like structure vary depending on ES cells or iPS cells used. However, for example, Iscove's Modified Dulbecco's Medium (IMDM) supplemented with FBS to a final concentration of 15% is used as a medium. Meanwhile, even in a case of a serum-free medium, a growth factor, a supplement, or the like may be added thereto as appropriate for use. Further, in order to form a sac-like structure efficiently, a vascular endothelial growth factor (VEGF) should be added at approximately 0 to 300 ng/ml, more preferably approximately 20 ng/ml. The culture environment varies depending on the type of ES cells or iPS cells used. However, the conditions are preferably 5% $CO_2$ at 35 to 38° C., more preferably 37° C. The culturing period until a sac-like structure is formed varies depending on the type of ES cells or iPS cells, but the presence can be observed on approximately Day 15 (14 to 16 days later) after seeding on feeder cells.

The formed sac-like structure has a follicular structure. In the structure, hematopoietic progenitor cells, particularly CD34-positive cells, are present in a concentrated state. The hematopoietic progenitor cells present inside the sac-like structure can be separated by physical means, for example, by passing the cells through a sterilized sieve-like tool (for example, cell strainer or the like).

Next, description will be given of a method for preparing platelets from the hematopoietic progenitor cells separated from the sac-like structure. The hematopoietic progenitor cells obtained by the separation are seeded on feeder cells, and cultured under conditions suitable for producing megakaryocytes and platelets. Herein, examples of the "conditions suitable for producing megakaryocytes and platelets" include culturing for approximately 7 to 15 days in the presence of thrombopoietin (TPO, approximately 10 to 200 ng/mL, preferably 100 ng/mL), or in the presence of a stem cell factor (SCF, approximately to 200 ng/mL, preferably 50 ng/mL), heparin (approximately 10 to 100 U/mL, preferably 25 U/ml), and TPO (approximately 10 to 200 ng/mL, preferably 100 ng/mL). As the culture environment, the conditions are preferably 5% $CO_2$ at 35 to 38° C., more preferably 37° C.

Moreover, in such a culture system, the timing of adding the compound represented by the general formula (I) or the like to this culture system is preferably when the hematopoietic progenitor cells are reseeded on the feeder cells. It is more preferable to add the compound represented by the general formula (I) or the like on approximately Day 22 after the culturing is started (Days 20 to 23, or Days 6 to 10 after the sac-like structure is reseeded).

Furthermore, in the method of the present invention, platelets can be prepared by: collecting a culture solution fraction (for example, in the method for forming a sac-like structure, a fraction present on approximately Days 22 to 28 after human iPS cells or ES cells are cultured) in which platelets released from megakaryocytes are abundant; and then removing components other than platelets (i.e., megakaryocytes and other blood cells) using a leukocyte reduction filter (available from, for example, Terumo Corporation, Asahi Kasei Medical Co., Ltd., and so forth) or the like.

As described above, the compound represented by the general formula (I) or the like suppresses ADAM17-mediated GPIbα shedding and has an action of maintaining a function of platelets. Thus, the present invention also provides a blood product comprising platelets and the compound represented by the general formula (I) or the like; it also provides a method for maintaining a function of platelets in a blood product, wherein the method comprises adding, to a blood product comprising platelets, the compound represented by the general formula (I) or the like.

Further, the compound represented by the general formula (I) or the like serves as an active ingredient for producing a blood product comprising platelets. Thus, the present invention also provides the compound represented by the general formula (I) or the like as a drug additive used to produce the blood product of the present invention.

The platelets comprised in the blood product of the present invention is not particularly limited, and may be platelets obtained by the above-described method for preparing platelets of the present invention or may be platelets derived from peripheral blood or the like obtained by collecting blood. When such a blood product is prepared, the blood product may also comprise other ingredients used to stabilize platelets by taking the storage instability of platelets and the like into consideration. Conditions for stabilizing platelets can be selected from among methods well known to those skilled in the art. For example, the product can be prepared by suspending platelets in a solution necessary to keep a function of platelets (for example, an ACD-A solution (a solution prepared from sodium citrate/citric acid/glucose) and the like; in some cases, frozen plasma or the like may be added as appropriate) at an appropriate concentration (for example, approximately $1\times10^8$ to $1\times10^{10}$ platelets/mL, preferably approximately $1\times10^9$ platelets/mL). Note that, as a container for storing the product comprising platelets, it is preferable to avoid using a material that activates platelets, such as glass. An amount (concentration) added of the compound represented by the general formula (I) or the like is preferably 0.01 to 100 μmol/L. If the amount added is below the lower limit, platelets tend not to keep the adhesion function. Even if the amount exceeds the upper limit, the effects are at a plateau.

EXAMPLES

Hereinafter, the present invention will be described more specifically based on Examples and Test Examples. However, the present invention is not limited to the following Examples. Note that megakaryocytes and platelets used in Test Examples described later were produced and analyzed by employing methods described below.
<Preparation of Human ES Cells, Human iPS Cells, and Feeder Cells>

As human ES cells (hES cells), a KhES cell line (KhES-3) established by and provided from Institute for Frontier Medical Sciences, Kyoto University was used.

As human iPS cells (hiPS cells), an iPS cell line (TkDA3-4) established at the University of Tokyo by introducing Oct4, Klf4, Sox2, and c-Myc into human-derived skin cells was also used). Further, the TkDA3-4 cells were cultured on radiation-exposed mouse fibroblasts in a medium mixture of Dulbecco's modified Eagle's medium and Ham's F-12 medium (manufactured by Sigma-Aldrich Co.) (mixing ratio 1:1) supplemented with 0.1 mM non-essential amino acid (manufactured by Invitrogen Corp.), 2 mM L-glutamine (manufactured by Invitrogen Corp.), 20% knockout serum replacement additive (KSR, manufactured by Invitrogen Corp.), 0.1 mM 2-mercaptoethanol, and 5 ng/ml basic fibroblast growth factor (bFGF, manufactured by Upstate). The cells were subcultured for every 3 days, and those keeping an undifferentiated state were used.

In addition, mouse embryo-derived fibroblasts, a C3H10T1/2 cell line (hereinafter also referred to as "10T1/2 cells"), purchased from RIKEN BioResource Center were cultured in basal medium. Eagle (BME, manufactured by Invitrogen Corp.) supplemented with 10% fetal bovine serum (FBS) and 2 mM L-glutamine. Then, the 10T1/2 cells were adjusted to a cell count of $8\times10^6$/10-cm dish, and exposed to 50-Gy radiation for use as feeder cells.
<Production and Analysis of Megakaryocytes and Platelets>

The human ES cells or the human iPS cells were seeded on the feeder cells such that the cell count was $5\times10^4$ to $1\times10^5$/10-cm dish. The cells were cultured in Iscove's Modified Dulbecco's Medium (IMDM, manufactured by Invitrogen Corp/GIBCO) supplemented with 15% FBS (product name: CELLect™ GOLD, manufactured by ICN Biomedicals Inc.), 2 mM L-glut amine (manufactured by Invitrogen Corp.), ITS supplement (10 μg/ml insulin, 5.5 mg/ml human transferrin, 5 ng/ml sodium selenite) (manufactured by Sigma-Aldrich Co.), 50 μg/ml ascorbic acid (Sigma-Aldrich Co.), 0.45 mM α-monothioglycerol (MTG, manufactured by Sigma-Aldrich Co.), and 20 ng/ml vascular endothelial growth factor (VEGF, manufactured by R&D Systems, Inc.). Further, this culturing was carried out at 37° C. in 5% $CO_2$ and 21% $O_2$ (atmospheric oxygen) using a $CO_2$ incubator (product name: HERA CELL 150i, manufactured by Thermo Fisher Scientific K. K.). Then, the medium was replaced every 3 days, and the culturing was continued under the conditions until Day 15 when a large number of sac structures (sac-like structures) containing hematopoietic progenitor cells therein were observed.

Next, after detached from the dish, the sac structures were disrupted and suspended in a 3% FBS-containing phosphate buffer solution (PBS). Then, the suspension was passed through a 40-μm cell strainer (manufactured by BD). The solution thus passed through was centrifuged at 440×g for 10 minutes to collect hematopoietic progenitor cells, and the cells was counted. The hematopoietic progenitor cells were seeded on 10T1/2 cells newly prepared in a 6-well plate ($6\times10^5$ cells/plate) exposed to 50-Gy radiation such that the number of the hematopoietic progenitor cells was 2 to $3\times10^4$/well. The hematopoietic progenitor cells were further cultured for 8 days in IMDM (manufactured by Invitrogen Corp/GIBCO) supplemented with 15% FBS (product name: CELLect™ GOLD, manufactured by ICN Biomedicals Inc.), 2 mM L-glutamine (manufactured by Invitrogen Corp.), ITS supplement (10 μg/ml insulin, 5.5 mg/ml transferrin, 5 ng/ml sodium selenite) (manufactured by Sigma-Aldrich Co.), 50 μg/ml ascorbic acid (manufactured by Sigma-Aldrich Co.), 0.45 mM MTG (manufactured by Sigma-Aldrich Co.), 100 ng/ml human thrombopoietin (human TPO, manufactured by PeproTech, Inc.), 50 ng/ml human stem cell factor (SCF, manufactured by PeproTech, Inc.), and 25 U/ml heparin. Thereby, megakaryocytes/platelets were induced.

Subsequently, the induced megakaryocytes/platelets were collected with an anticoagulant solution (Acid Citrate Dextrose, ACD), followed by centrifugation at 900 rpm for 10 minutes without a break. The supernatant obtained by the centrifugation was further centrifuged at 1500 rpm for 10 minutes without a break to remove the supernatant. Thereafter, the numbers of megakaryocytes and platelets in the precipitate thus obtained were analyzed by flow cytometry using antibodies for staining.

Note that, in the flow cytometry, FACS Aria manufactured by Becton, Dickinson and Company was used. As the antibodies used to stain the megakaryocytes and the platelets, used were a Phycoerythrin (PE)-modified anti-human CD42a (GPIX) antibody, a PE-modified anti-human CD42b (GPIbα) antibody, and an allophycocyanin (APC)-labelled anti-CD41a (integrin αIIbbeta3 complex, HIP8 clone) antibody (manufactured by BD Bioscience). Additionally, in order to accurately measure the absolute numbers of the megakaryocytes and the platelets, the cells were stained with these antibodies, and the analysis was conducted by flow cytometry using TruCount beads (manufactured by BD Bioscience), also.

Test Example 1

Figure 2:
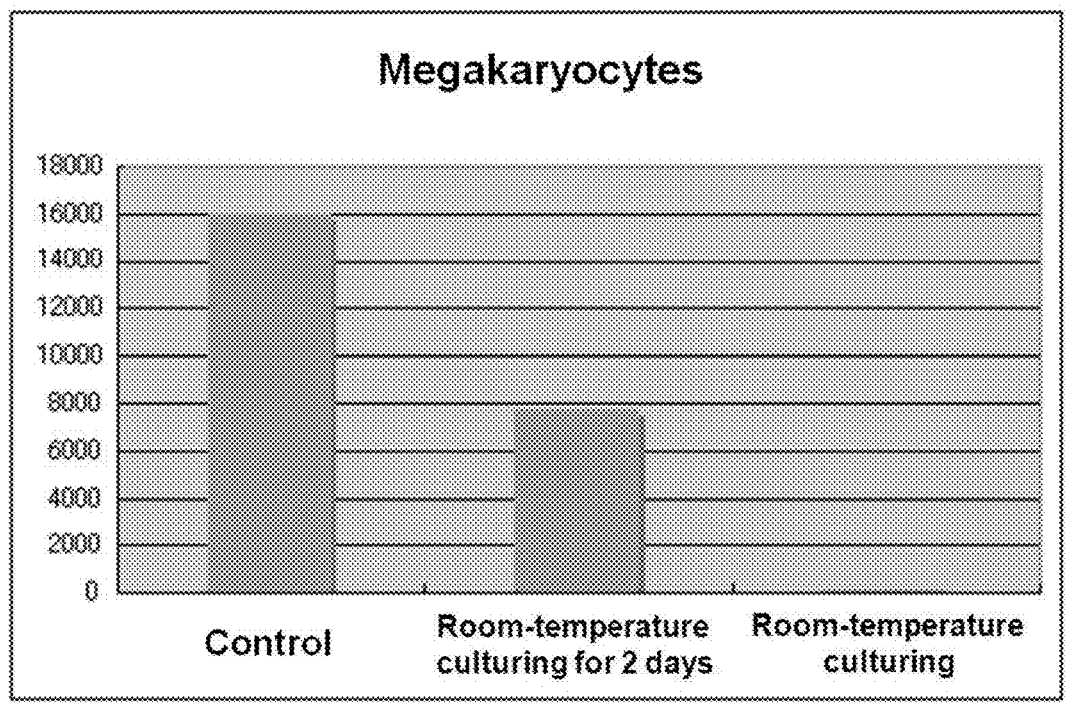
FIG. 2 is a graph showing the number of megakaryocytes produced from ES cell-derived hematopoietic progenitor cells by culturing under room temperature conditions. The unit of the vertical axis is cell count/well.
Figure 3:
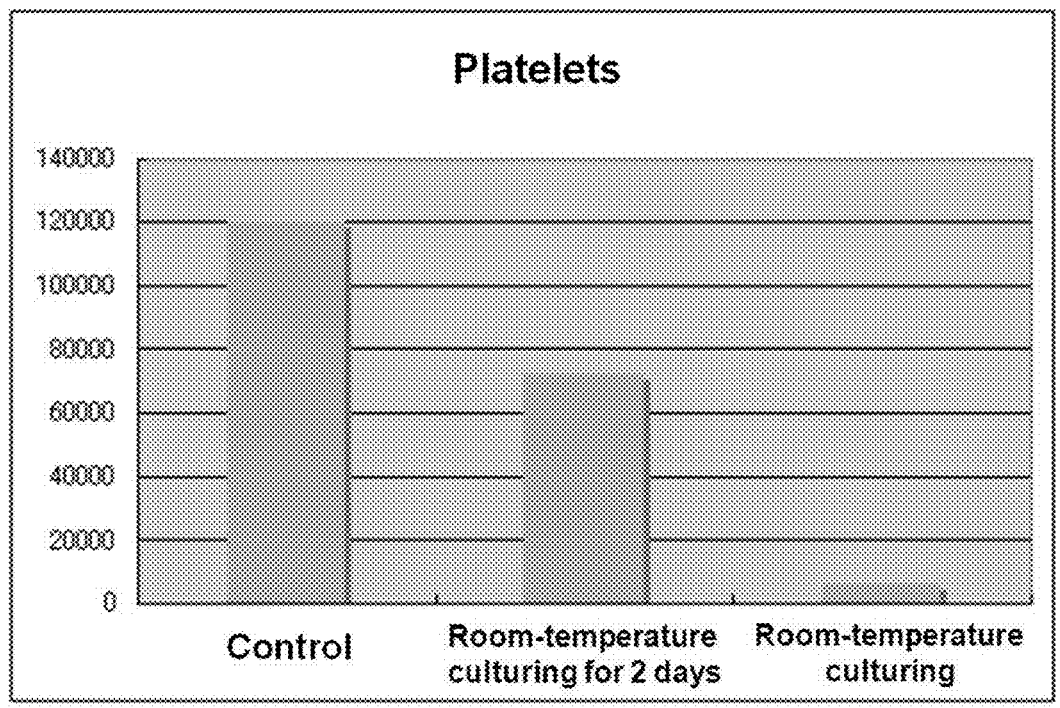
FIG. 3 is a graph showing a total number of platelets produced from the ES cell-derived hematopoietic progenitor cells by culturing under room temperature conditions. The unit of the vertical axis is cell count/well.

Induction to Megakaryocytes/Platelets from ES Cell-Derived Hematopoietic Progenitor Cells Under Room Temperature Condition In order to examine whether or not it is possible to induce megakaryocytes/platelets by culturing under room temperature condition (culturing at 25° C.), the induction of megakaryocytes/platelets from the ES cell-derived hematopoietic progenitor cells obtained as described above was attempted under conditions illustrated in FIG. 1. Specifically, in the above-described 8-day culture process for inducing hematopoietic progenitor cells to megakaryocytes/platelets, each culturing was conducted under the following conditions:

Control: culturing at 37° C. for 8 days
Room-temperature culturing for 2 days: culturing at 37° C. for 6 days, followed by culturing at 25° C. for 2 days, and Room-temperature culturing: culturing at 25° C. for 8 days. Then, the numbers of megakaryocytes and platelets collected as described above were counted by flow cytometry. FIGS. 2 and 3 show the obtained results.

As apparent from the results shown in FIGS. 2 and 3, megakaryocytes and platelets were hardly obtained by the culturing at 25° C. for 8 days. Additionally, by the culturing at 25° C. for 2 days before the flow cytometry analysis, megakaryocytes and platelets were obtained, but the amounts were only approximately half of those of the control.

Test Example 2

Induction to Megakaryocytes/Platelets from Umbilical Cord Blood-Derived CD34(+) Cells Under Room Temperature Condition Whether or not it is possible to induce platelets from umbilical cord blood-derived CD34(+) cells by culturing under room temperature condition (culturing at 24 to 25° C.) was examined.

First, $10^6$ $CD45^{low}$ $CD34^+$ cells were selected and isolated from umbilical cord blood (CB) using a bead column. Of the obtained umbilical cord blood-derived CD34(+) cells, $4 \times 10^4$ cells were seeded on the feeder cells described above and cultured for 4 days in a medium A (IMDM (manufactured by Invitrogen Corp/GIBCO) supplemented with 15% FBS (product name: CELLect™ GOLD, manufactured by ICN Biomedicals Inc.), 2 mM L-glutamine (manufactured by Invitrogen Corp.), ITS supplement (10 µg/ml insulin, 5.5 mg/ml transferrin, 5 ng/ml sodium selenite) (manufactured by Sigma-Aldrich Co.), 50 µg/ml ascorbic acid (manufactured by Sigma-Aldrich Co.), 0.45 mM MTG (manufactured by Sigma-Aldrich Co.), and a cytokine cocktail (2 ng/ml TPO (manufactured by PeproTech, Inc.), 7.5 ng/ml SCF (manufactured by PeproTech, Inc.), 11 ng/ml FLT-3)). On Day 4 after the culturing, to the umbilical cord blood-derived CD34 (+) cells, a medium B was added in the same amount as that of the medium A. Note that the medium B is different from the medium A in that the medium B was supplemented with 30 ng/ml TPO, 1 ng/ml SCF, 7.5 ng/ml IL-6, and 13.5 ng/ml IL-9 as a cytokine cocktail. Meanwhile, the medium A and the medium B have the same composition, except that the supplemented cytokine cocktails are different.

Figure 4:
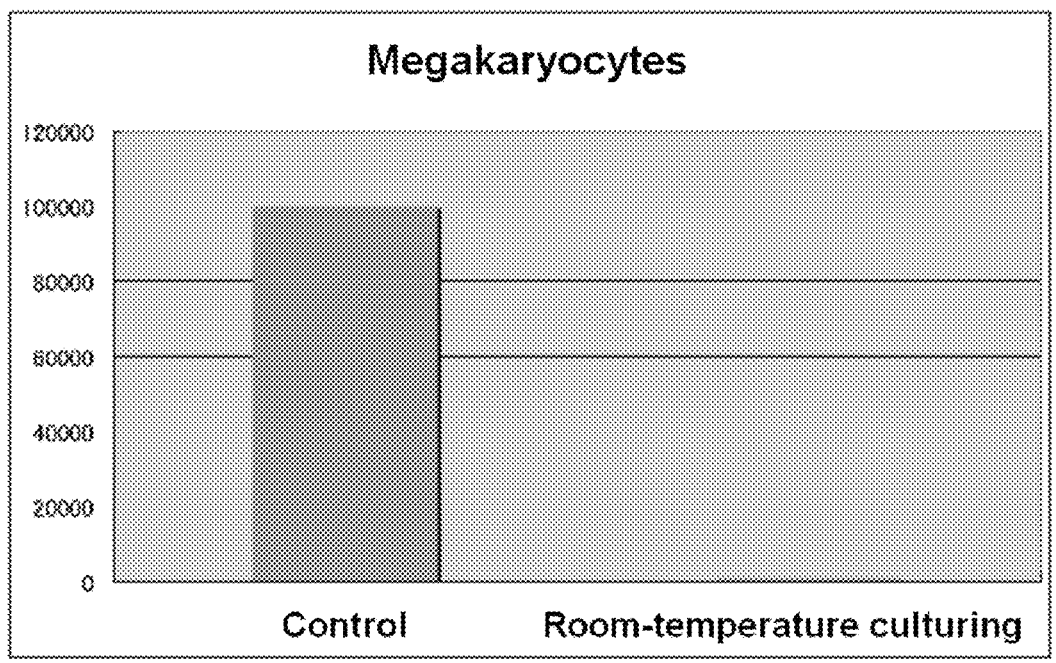
FIG. 4 is a graph showing the number of megakaryocytes produced from umbilical cord blood-derived CD34(+) cells by culturing under room temperature condition. The unit of the vertical axis is cell count/well.
Figure 5:
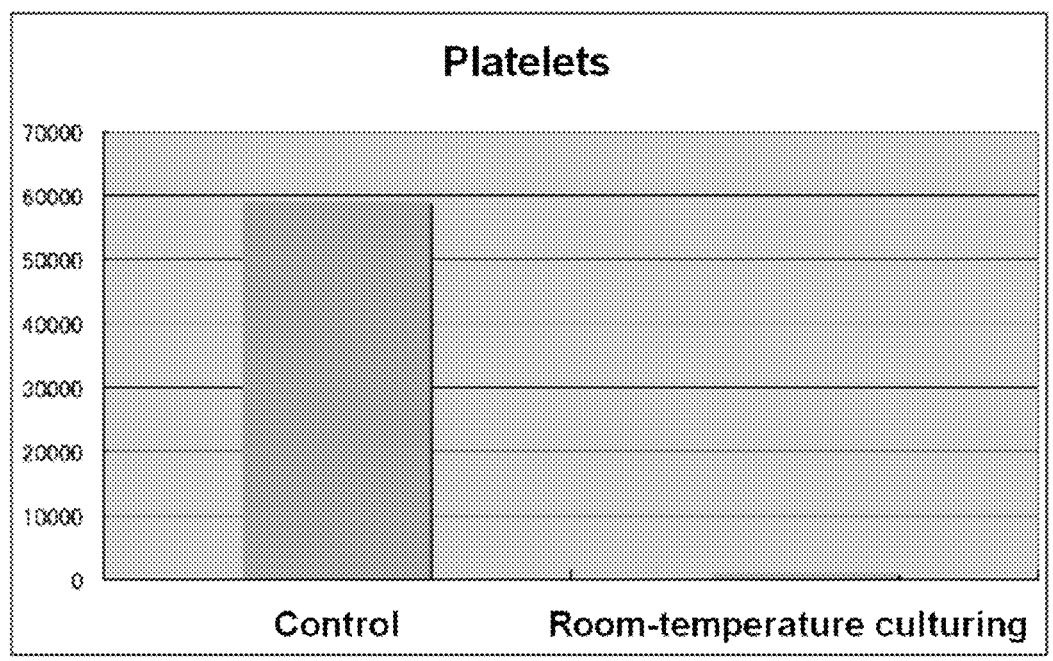
FIG. 5 is a graph showing a total number of platelets produced from the umbilical cord blood-derived CD34(+) cells by culturing under room temperature condition. The unit of the vertical axis is cell count/well.

Then, the umbilical cord blood-derived CD34(+) cells on Day 7 thus cultured were adjusted to a cell count of $4 \times 10^5$/mL in the medium B. The cells were further cultured for 7 days at 37° C. (control), or further cultured for 7 days at 24 to 25° C. (room-temperature culturing). On Day 14 after the culturing, the numbers of megakaryocytes and platelets were counted by flow cytometry. FIGS. 4 and 5 show the obtained results.

As apparent from the results shown in FIGS. 4 and 5, megakaryocytes and platelets were hardly obtained by the culturing at approximately 25° C. for 7 days as in the case of the ES cell-derived hematopoietic progenitor cells described above. Thus, the results shown in Test Examples 1 and 2 reveal that, in a culture system for differentiating megakaryocytes from cells capable of differentiating into megakaryocytes, such as ES cells and umbilical cord blood-derived CD34(+) cells, to produce platelets from the megakaryocytes, the culture temperature is preferably around 37° C., while megakaryocytes and platelets cannot be produced by culturing under room temperature condition of around 25° C.

However, if the culture temperature is around 37° C. in the culture system for producing platelets, ADAM17 sheds GPIbα, which is an important factor for blood coagulation located on the surface of platelets. This brings about a problem that it is hard to obtain platelets net demonstrating a hemostatic function. Meanwhile, inhibitors (for example, GM6001) targeting metalloproteinases including ADAM17 may be added to a culture system in order to suppress GPIbα shedding. In such a case, however, metalloproteinases essential for hematopoietic function (MMP-9, MMP-14) other than ADAM17 are also inhibited. Hence, such inhibitors need to be added only at a certain period when platelet production is observed most abundantly, and are not preferable in establishing a plant or the like for a culture system producing platelets. Furthermore, there is a concern about safety when non-specific metalloproteinase inhibitors such as GM6001 are administered in vivo. Thus, it is not preferable to use platelets mixed with such inhibitors as a blood product, either.

For these reasons, compounds specifically inhibiting ADAM17 described in Examples below were designed and synthesized. Note that $^1$H-NMR spectra described below were measured with an ECA400 spectrometer (400 MHz, manufactured by JEOL Ltd.) using deuterated chloroform ($CDCl_3$) or deuterated dimethyl sulfoxide ($DMSO-d_6$) as a solvent, and tetramethylsilane (TMS) as the internal standard. In the measurement result of chemical shifts, δ values were expressed in ppm, and coupling constant J values were expressed in Hz. The abbreviation s means singlet; d, doublet; t, triplet; q, quartet; dd, doublet doublet; m, multiplet; and br, broad. For low-resolution mass spectrum (fast atom bombardment: FAB-MS) measurement, JEOL Ltd. JMS-HX-110A model was used, and for mass spectrum (electrospray ionization: ESI-MS) measurement, Exactive manufactured by Thermo Fisher Scientific K. K. was used.

Example 1

N-[2-(4-But-2-ynyloxybenzenesulfonyl)-1-(4-diethylaminomethylphenyl)ethyl]-N-hydroxyformamide
(I-1)

[Chem. 17]

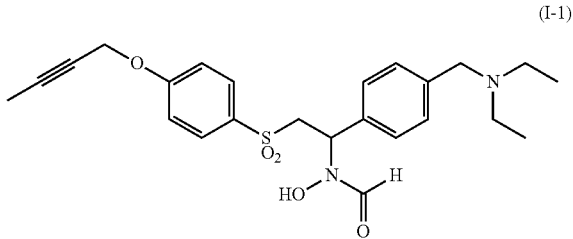

(I-1)

(1-1): 1-But-2-ynyloxy-4-methanesulfonylbenzene
(V-1)

2.88 g (15.9 mmol) of 4-methylsulfonylphenol was added to and dissolved in a dimethylsulfoxide solution (30 mL) of 2.12 g (15.9 mmol) of 1-bromo-2-butyne, and then 2.64 g (19.1 mmol) of potassium carbonate was added thereto. After stirred for 6 hours, brine was added thereto and extracted with ethylacetate. The organic layer was washed with brine, and dried over anhydrous magnesium sulfate. 3.39 g (15.11 mmol) of 1-but-2-ynyloxy-4-methanesulfonylbenzene (V-1)

was obtained as a roughly-purified product (yield 95%). Its physical properties are shown below.

MS (FAB) m/z: 225 (M+H)$^+$.

$^1$H-NMR(CDCl$_3$): δ 7.88 (2H, m), 7.10 (2H, m), 4.73 (2H, m), 3.04 (3H, s), 1.87 (3H, t, J=2.3 Hz).

(1-2): tert-Butyl{4-[2-(4-but-2-ynyloxybenzene-sulfonyl)acetyl]benzyl}carbamate (VII-1)

In an argon atmosphere at −78° C., 3.65 mL (7.29 mmol) of a hexane-heptane-ethylbenzene solution of 2.0 M lithium diisopropylamide was added to a tetrahydrofuran (70 mL) solution of 1.36 g (6.08 mmol) of the compound (V-1) obtained in the above (1-1), stirred for 30 minutes, and then 12.16 mL (12.16 mmol) of a tetrahydrofuran solution of 1.0 M lithium hexamethyldisilazide and 5 mL of a tetrahydrofuran solution of 1.61 g (6.08 mmol) of methyl 4-(tert-butoxycarbonylaminomethyl)benzoate were added thereto. After stirred at −78° C. for 5 minutes, this was gradually heated up to room temperature, and stirred for 1 hour. After brine was added thereto, this was extracted with ethyl acetate, and the organic layer was washed with brine. After dried over anhydrous magnesium sulfate, the solvent was evaporated away under reduced pressure. Purified by silica gel column chromatography (hexane/ethyl acetate=2/1→1/1), this gave 2.02 g (4.41 mmol) of tert-butyl{4-[2-(4-but-2-ynyloxybenzenesulfonyl)acetyl]benzyl}carbamate (VII-1) as a colorless molten caramel-like substance (yield 72%). Its physical properties are shown below.

MS (FAB) m/z: 480 (M+Na)$^+$.

$^1$H-NMR (CDCl$_3$): δ 7.93 (2H, br d, J=8.2 Hz), 7.81 (2H, m), 7.40 (2H, br d, J=8.2 Hz), 7.07 (2H, m), 4.72 (2H, m), 4.70 (2H, s), 4.39 (2H, m), 1.87 (3H, t, J=2.3 Hz), 1.57 (9H, s).

(1-3): tert-Butyl{4-[2-(4-but-2-ynyloxybenzene-sulfonyl)-1-hydroxyethyl]benzyl}carbamate (IX-1)

At 0° C., 167 mg (4.41 mmol) of sodium borohydride was added to a methanol (50 mL) solution of 2.02 g (4.41 mmol) of the compound (VII-1) obtained in the above (1-2). After stirred for 2 hours and 30 minutes, brine and aqueous saturated ammonium chloride solution were added thereto. Methanol was evaporated away under reduced pressure, then the residue was extracted with ethyl acetate, and the organic layer was washed with brine, and dried over anhydrous magnesium sulfate. The solvent was evaporated away under reduced pressure to give 2.04 g (4.41 mmol) of tert-butyl{4-[2-(4-but-2-ynyloxybenzenesulfonyl)-1-hydroxyethyl]benzyl}carbamate (IX-1), as a roughly-purified amorphous solid substance (yield 99%). Its physical properties are shown below.

MS (FAB) m/z: 482 (M+Na)$^+$.

(1-4): tert-Butyl{4-[2-(4-but-2-ynyloxybenzene-sulfonyl)vinyl]benzyl}carbamate (II-1a)

At 0° C., 0.7 mL (8.8 mmol) of methanesulfonyl chloride was added to a dichloromethane (45 mL) solution of 2.04 g (4.41 mmol) of the compound (IX-1) obtained in the above (1-3) and 3.1 mL (22.1 mmol) of triethylamine. After stirred for 3 hours and 30 minutes, brine was added thereto, and extracted with chloroform. The organic layer was washed with brine, and dried over anhydrous magnesium sulfate. The solvent was evaporated away under reduced pressure, and the residue was purified by silica gel column chromatography (chloroform/ethyl acetate=3/1) to give 1.77 g (4.00 mmol) of tert-butyl{4-[2-(4-but-2-ynyloxybenzenesulfonyl)vinyl]benzyl}carbamate (II-1a) as a colorless amorphous solid (yield 91%). Its physical properties are shown below.

$^1$H-NMR (CDCl$_3$): δ 7.87 (2H, d, J=8.7 Hz), 7.61 (1H, d, J=15 Hz), 7.43 (2H, d, J=8.2 Hz), 7.30 (2H, d, J=8.2 Hz), 7.10 (2H, d, J=8.7 Hz), 6.82 (1H, d, J=15 Hz), 4.88 (1H, m), 4.71 (2H, m), 4.33 (2H, m), 1.86 (3H, m), 1.45 (9H, s).

(1-5): 4-[(E)-2-(4-But-2-ynyloxybenzenesulfonyl) vinyl]benzylamine hydrochloride (II-1b)

At 0° C., 2 mL of 4 M-hydrochloric acid/dioxane was added to a methanol (5 mL) solution of 295 mg (0.67 mmol) of the compound (II-1a) obtained in the above (1-4), stirred for 10 minutes, heated up to room temperature, and stirred for 2 hours. The solvent was evaporated away under reduced pressure, then 20 mL of methanol was added thereto, and the solvent was again evaporated away under reduced pressure to give 4-[(E)-2-(4-but-2-ynyloxybenzenesulfonyl)vinyl]benzylamine hydrochloride (II-1b) as a colorless solid. Its physical properties are shown below.

$^1$H-NMR (DMSO-d$_6$): δ 7.85 (2H, d, J=8.7 Hz), 7.78 (2H, d, J=8.2 Hz), 7.52 (2H, d, J=8.2 Hz), 7.20 (2H, d, J=8.7 Hz), 4.87 (2H, m), 4.05 (2H, m), 1.83 (3H, m).

(1-6): {4-[(E)-2-(4-But-2-ynyloxybenzenesulfonyl) vinyl]benzyl}diethylamine (II-1c)

At 0° C., 1 mL of acetaldehyde, 212 mg (1.00 mmol) of sodium triacetoxyhydroborate and 3 drops of acetic acid were added to a methanol (6 mL) solution of the compound (II-1b) obtained in the above (1-5), and then stirred at room temperature for 1 hour and 30 minutes. After brine and saturated aqueous sodium bicarbonate solution were added thereto, and the solvent was evaporated away under reduced pressure. This was extracted with chloroform, the organic layer was washed with brine and dried over anhydrous magnesium sulfate. The solvent was evaporated away under reduced pressure, and the residue was purified by silica gel column chromatography (chloroform/methanol=20/1→10/1) to give 111.7 mg (0.28 mmol) of {4-[(E)-2-(4-but-2-ynyloxybenzenesulfonyl)vinyl]benzyl}diethylamine (II-1c) as a pale yellow amorphous solid (two steps yield 42%). Its physical properties are shown below.

MS (FAB) m/z: 398 (M+H)$^+$.

(1-7): N-[2-(4-But-2-ynyloxybenzenesulfonyl)-1-(4-diethylaminomethylphenyl)ethyl]hydroxylamine (III-1)

50% hydroxylamine solution (3 mL) was added to a tetrahydrofuran (8 mL) solution of 108 mg (0.27 mmol) of the compound (II-1c) obtained in the above (1-6), and stirred at room temperature for 25 hours. The reaction solution was evaporated under reduced pressure, and then water was added thereto and extracted with chloroform. The organic layer was washed with brine, dried over anhydrous magnesium sulfate, and concentrated under reduced pressure. 92.9 mg (0.22 mmol) of N-[2-(4-but-2-ynyloxybenzenesulfonyl)-1-(4-diethylaminomethylphenyl)ethyl]hydroxylamine (III-1) was obtained as a pale yellow amorphous solid (yield 81%). Its physical properties are shown below.

$^1$H-NMR (CDCl$_3$): δ 7.84 (2H, m), 7.27 (2H, m), 7.20 (2H, m), 7.07 (2H, m), 4.72 (2H, m), 3.75 (1H, m), 3.51 (2H, s), 3.33 (1H, m), 2.49 (4H, m), 1.87 (3H, s), 1.03 (6H, m).

(1-8): N-[2-(4-But-2-ynyloxybenzenesulfonyl)-1-(4-diethylaminomethylphenyl)ethyl]-N-hydroxyformamide (I-1)

1 mL of formic acid was cooled at 0° C., then 0.3 mL of acetic anhydride was dropwise added thereto and stirred for 30 minutes to prepare a formic acid/acetic acid mixed acid anhydride solution. At 0° C., 0.6 ml of the formic acid/acetic acid mixed acid anhydride solution prepared previously was added to a tetrahydrofuran (3 mL) solution of 92 mg (0.21 mmol) of the compound (III-1) obtained in the above (1-7), and stirred at room temperature for 4 hours. The reaction mixture was concentrated under reduced pressure, and then azeotroped with toluene. The obtained oily substance was dissolved in 2 mL of chloroform and 10 mL of methanol, and stirred for 12 hours. The solution was concentrated under reduced pressure, and the resulting oily substance was dissolved in chloroform and neutralized with saturated aqueous sodium bicarbonate solution added thereto. After extracted with chloroform, the extract was washed with brine and dried over anhydrous magnesium sulfate. Purifying by middle-pressure silica gel column chromatography (chloroform/methanol=95/5→75/25) gave 53.9 mg (0.11 mmol) of N-[2-(4-but-2-ynyloxybenzenesulfonyl)-1-(4-diethylaminomethylphenyl)ethyl]-N-hydroxyformamide (I-1) as a pale yellow amorphous solid (yield 52%). Its physical properties are shown below.

MS (FAB) m/z: 459(M+H)$^+$.

$^1$H-NMR (CDCl$_3$): δ 8.32 (0.6H, s), 8.10 (0.4H, s), 7.80-7.86 (2H, m), 7.21-7.30 (4H, m), 7.06-7.14 (2H, m), 5.65 (0.6H, m), 5.36 (0.4H, m), 4.74 (2H, br s), 4.20 (0.4H, m), 4.05 (0.6H, br t, J=13 Hz), 3.48-3.57 (3H, m), 2.46 (4H, m), 1.87 (3H, br s), 0.99 (6H, m).

Example 2

N-[2-(4-But-2-ynyloxybenzenesulfonyl)-1-(4-dimethylaminomethylphenyl)ethyl]-N-hydroxyformamide (I-2)

[Chem. 18]

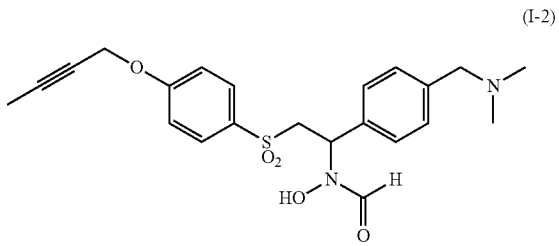

(I-2)

According to the same operation as in Example 1, the above-mentioned compound (I-2) was obtained.

MS (FAB) m/z: 431 (M+H)$^+$.

$^1$H-NMR (CDCl$_3$): δ 8.28 (0.6H, s), 8.14 (0.4H, s), 7.79-7.91 (2H, m), 7.04-7.32 (6H, m), 5.69 (0.6H, m), 5.35 (0.4H, m), 4.74 (2H, br s), 4.18 (0.4H, m), 4.07 (0.6H, m), 3.47 (1H, m), 3.33 (2H, m), 2.11 (6H, s), 1.87 (3H, s).

Example 3

N-{4-[2-(4-But-2-ynyloxybenzenesulfonyl)-1-(formylhydroxyamino)ethyl]benzyl}-2-methoxyacetamide (I-3)

[Chem. 19]

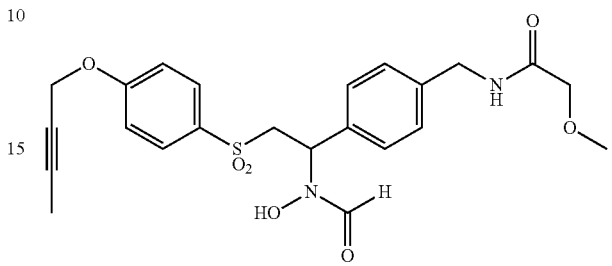

(I-3)

(3-1): N-{4-[2-(4-But-2-ynyloxybenzenesulfonyl)vinyl]benzyl}-2-methoxyacetamide (II-3)

At room temperature, 0.2 mL (1.85 mmol) of methoxyacetyl chloride was dropwise added to a pyridine solution (5 mL) of 283 mg (0.75 mmol) of the compound (II-1b) obtained in the above-mentioned Example 1 (1-5). After 2 days, brine was added thereto, extracted with ethyl acetate, and washed with brine. This was dried over anhydrous magnesium sulfate, the solvent was evaporated away under reduced pressure, and the residue was purified by silica gel column chromatography (chloroform/methanol=20/1→10/1) to give 296 mg (0.71 mmol) of the compound (II-3) as a pale yellow solid (yield 94%). Its physical properties are shown below.

MS (FAB) m/z: 414 (M+H)$^+$.

(3-2): N-{4-[2-(4-But-2-ynyloxybenzenesulfonyl)-1-(formylhydroxyamino)ethyl]benzyl}-2-methoxyacetamide (I-3)

According to the same process as in the above-mentioned Example 1 (1-7 and 1-8) but using the compound (II-3) obtained in the above (3-1), N-{4-[2-(4-but-2-ynyloxybenzenesulfonyl)-1-(formylhydroxyamino)ethyl]benzyl}-2-methoxyacetamide (I-3) was obtained. Its physical properties are shown below.

$^1$H-NMR (CDCl$_3$): δ 8.32 (0.6H, s), 8.09 (0.4H, s), 7.77-7.88 (2H, m), 7.20-7.31 (4H, m), 7.06-7.16 (2H, m), 5.65 (0.6H, m), 5.37 (0.4H, m), 4.75 (2H, br s), 4.39-4.47 (2H, m), 4.16 (0.4H, m), 4.03 (0.6H, br t), 3.93 (0.8H, br s), 3.90 (1.2H, br s), 3.46 (1H, m), 3.40 (3H, br s), 1.87 (3H, br s).

Example 4

N-{4-[2-(4-But-2-ynyloxybenzenesulfonyl)-1-(formylhydroxyamino)ethyl]benzyl}methanesulfonamide (I-4)

[Chem. 20]

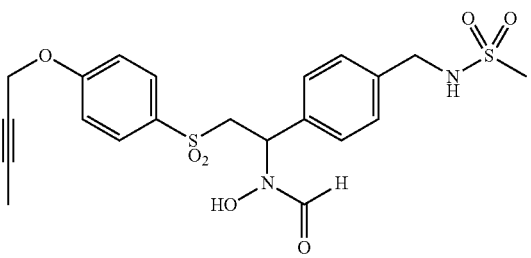

(I-4)

According to the same operation as in Example 3, the above-mentioned compound (I-4) was obtained.

MS (FAB) m/z: 481 (M+H)$^+$.

$^1$H-NMR (CDCl$_3$): δ 8.42 (0.6H, s), 7.87 (0.4H, s), 7.78-7.88 (2H, m), 7.30-7.35 (4H, m), 7.06-7.17 (2H, m), 5.65 (0.6H, m), 5.39 (0.4H, m), 4.75 (2H, m), 4.28 (2H, m), 4.15 (0.4H, m), 4.00 (0.6H, br t, J=12 Hz), 3.45 (1H, m), 2.91 (1.2H, s), 2.89 (1.8H, s), 1.87 (3H, m).

Example 5

N-{4-[2-(4-But-2-ynyloxybenzenesulfonyl)-1-(formylhydroxyamino)ethyl]benzyl}benzamide (I-5)

[Chem. 21]

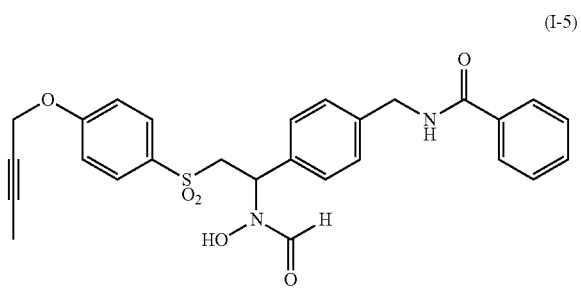

(I-5)

According to the same operation as in Example 3, the above-mentioned compound (I-5) was obtained.

MS (FAB) m/z: 507 (M+H)$^+$.

$^1$H-NMR (CDCl$_3$): δ 8.31 (0.6H, s), 8.08 (0.4H, s), 7.73-7.87 (4H, m), 7.51 (1H, m), 7.42 (2H m), 7.27-7.33 (3H, m), 7.07-7.14 (2H, m), 5.65 (0.6H, m), 5.37 (0.4H, m), 4.73 (2H, m), 4.54-4.62 (2H, m), 4.15 (0.4H, m), 4.00 (0.6H, m), 3.45 (1H, m), 1.86 (3H, br s).

Example 6

N-[2-(4-But-2-ynyloxybenzenesulfonyl)-1-(4-morpholin-4-ylmethylphenyl)ethyl]-N-hydroxyformamide (I-6)

[Chem. 22]

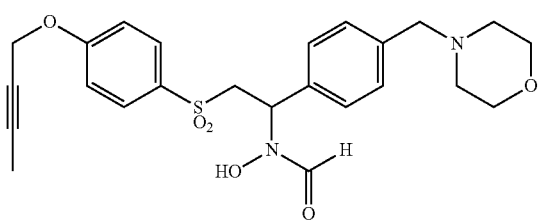

(I-6)

(6-1): tert-Butyl-(4-methanesulfonylphenoxy)dimethylsilane (XII-6)

9.9 g (145.18 mmol) of imidazole was added to and dissolved in an N,N-dimethylformamide solution (150 mL) of 10 g (58.07 mmol) of 4-methylsulfonylphenol, and then 10.5 g (69.7 mmol) of tert-butyldimethylchlorosilane was added thereto and stirred. After the reaction, brine was added thereto and extracted with ethyl acetate. The organic layer was washed three times with brine, and dried over anhydrous magnesium sulfate. Purifying by silica gel column chromatography (hexane/ethyl acetate=5/1→3/1) gave 15.97 g (55.75 mmol) of tert-butyl-(4-methanesulfonylphenoxy)dimethylsilane (XII-6) (yield 96%). Its physical properties are shown below.

$^1$H-NMR (CDCl$_3$): δ 7.83 (1H, m), 7.81 (1H, m), 6.97 (1H, m), 6.95 (1H, m), 3.04 (1H, s), 1.56 (9H, s), 0.25 (6H, s).

(6-2): 2-[4-(tert-Butyldimethylsilanyloxy)benzenesulfonyl]-1-(4-morpholin-4-ylmethylphenyl)ethanone (XIII-6)

In an argon atmosphere at −78° C., 4.19 mL (8.37 mmol) of a hexane-heptane-ethylbenzene solution of 2.0 M lithium diisopropylamide was added to a tetrahydrofuran solution of 2.6 g (6.98 mmol) of tert-butyl-(4-methanesulfonylphenoxy)dimethylsilane (XII-6) obtained in the above (6-1), and 6.98 mL (6.98 mmol) of a tetrahydrofuran solution of 1.0 M lithium hexamethyldisilazide and 5 mL of a tetrahydrofuran solution of 1.6 g (6.98 mmol) of methyl 4-morpholin-4-ylmethylbenzoate (IX-6) were added thereto. Subsequently, this was gradually heated up to room temperature with stirring. After the reaction, brine was added thereto, extracted with ethyl acetate, and the organic layer was washed with brine. After dried over anhydrous magnesium sulfate, the solvent was evaporated away under reduced pressure. 3.74 g of 2-[4-(tert-butyldimethylsilanyloxy)benzenesulfonyl]-1-(4-morpholin-4-ylmethylphenyl)ethanone (XIII-6) was obtained as a roughly-purified product.

(6-3): 2-[4-(tert-Butyldimethylsilanyloxy)benzenesulfonyl]-1-(4-morpholin-4-ylmethylphenyl)ethanol (XIV-6)

At 0° C., 264 mg (6.98 mmol) of sodium borohydride was added to a methanol (50 mL) solution of 3.74 g (6.98 mmol) of the compound (XIII-6) obtained in the above (6-2). After stirred for 1 hour, brine was added thereto. Methanol was evaporated away under reduced pressure, and the residue was extracted with ethyl acetate. The organic layer was washed with brine, and dried over anhydrous magnesium sulfate. The solvent was evaporated away under reduced pressure, and the residue was purified by silica gel column chromatography (ethyl acetate→ethyl acetate/methanol=10/1) to give 2.19 g (4.48 mmol) of 2-[4-(tert-butyldimethylsilanyloxy)benzenesulfonyl]-1-(4-morpholin-4-ylmethylphenyl)ethanol (XIV-6). Its physical properties are shown below.

$^1$H-NMR (CDCl$_3$): δ 7.83 (2H, m), 7.25-7.30 (4H, m), 6.98 (2H, m), 5.22 (1H, d, J=7.7 Hz), 3.68 (4H, m), 3.46 (3H, m), 3.30 (1H, dd, J=1.5, 14 Hz), 2.40 (4H, m), 0.99 (9H, s), 0.25 (6H, s).

(6-4): 4-[(E)-2-(4-Morpholin-4-ylmethylphenyl)ethenesulfonyl]phenol (XVI-6)

3.10 mL of triethylamine was added to a dichloromethane solution (45 mL) of 2.19 g (4.48 mmol) of 2-[4-(tert-butyldimethylsilanyloxy)benzenesulfonyl]-1-(4-morpholin-4-ylmethylphenyl)ethanol (XIV-6) obtained in the above (6-3), and stirred at 0° C. 0.61 mL (8.91 mmol) of methanesulfonyl chloride was added thereto, and stirred at room temperature for 8 hours. Further, 3.10 mL of triethylamine and 0.61 mL of methanesulfonyl chloride were added thereto, and stirred for 4 hours. Brine was added and extracted with chloroform. The organic layer was washed with brine, and dried over anhydrous magnesium sulfate. The solvent was evaporated away under reduced pressure, and the residue was purified by silica gel column chromatography (hexane/ethyl acetate=1/2→ethyl acetate→ethyl acetate/methanol=10/1) to give 0.757 g (2.11 mmol) of 4-[(E)-2-(4-morpholin-4-ylmethylphenyl)ethenesulfonyl]phenol (XVI-6) (yield 47%). Its physical properties are shown below.

¹H-NMR (CDCl₃): δ 8.01 (1H, d, J=8.7 Hz), 7.81 (1H, d, J=8.7 Hz), 7.61 (1H, d, J=15 Hz), 7.35-7.47 (5H, m), 6.92 (1H, d, J=6.9 Hz), 6.81 (1H, d, J=15 Hz), 3.71 (4H, m), 3.51 (2H, m), 2.44 (4H, m).

(6-5): 4-[4-[(E)-2-(4-But-2-ynyloxybenzenesulfonyl)vinyl]benzyl]morpholine (II-6)

108 mg (0.780 mmol) of potassium carbonate and 0.094 mL (1.04 mmol) of 1-bromo-2-butyne were added to an N,N-dimethylformamide solution of 187 mg (0.520 mmol) of 4-[(E)-2-(4-morpholin-4-ylmethylphenyl)ethenesulfonyl]phenol (XVI-6) obtained in the above (6-4), and stirred for 4 hours. Brine was added thereto, and extracted with ethyl acetate. The organic layer was washed with brine, and dried over anhydrous magnesium sulfate. The solvent was evaporated away under reduced pressure, and the residue was purified by silica gel column chromatography (ethyl acetate/chloroform=1/1→1/2→ethyl acetate) to give 0.0238 g (0.0578 mmol) of 4-[4-[(E)-2-(4-but-2-ynyloxybenzenesulfonyl)vinyl]benzyl]morpholine (II-6) (yield 11%). Its physical properties are shown below.

¹H-NMR (CDCl₃): δ 7.87 (2H, d, J=8.7 Hz), 7.63 (1H, d, J=15.5 Hz), 7.35-7.44 (4H, m), 7.07 (2H, d, J=8.7 Hz), 6.83 (1H, d, J=15.5 Hz), 4.71 (2H, m), 3.69 (4H, m), 3.50 (2H, s), 2.43 (4H, m), 1.86 (3H, s).

(6-6): N-[2-(4-But-2-ynyloxybenzenesulfonyl)-1-(4-morpholin-4-ylmethylphenyl)ethyl]-N-hydroxyformamide (I-6)

According to the same process as in the above (1-7 and 1-8) but using the compound (II-6) obtained in the above (6-5), N-[2-(4-but-2-ynyloxybenzenesulfonyl)-1-(4-morpholin-4-ylmethylphenyl)ethyl]-N-hydroxyformamide (I-6) was obtained. Its physical properties are shown below.

MS (FAB) m/z: 473 (M+H)⁺.

¹H-NMR (CDCl₃): δ 8.45 (0.6H, s), 8.11 (0.4H, s), 7.80-7.88 (2H, m), 7.23-7.32 (4H, m), 7.07-7.16 (2H, m), 5.63 (0.6H, m), 5.38 (0.4H, m), 4.75 (2H, m), 4.19 (0.4H, m), 4.03 (0.6H, m), 3.64-3.71 (4H, m), 3.40-3.51 (2H, m), 2.39 (4H, m), 1.87 (3H, m).

Example 7

N-Hydroxy-N-[1-(4-morpholin-4-ylmethylphenyl)-2-(4-pent-2-ynyloxybenzenesulfonyl)ethyl]formamide (I-7)

[Chem. 23]

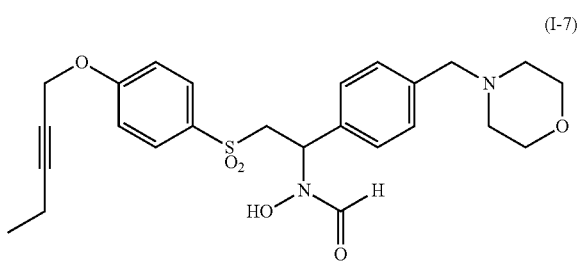

(I-7)

According to the same operation as in Example 6, the above-mentioned compound (I-7) was obtained.

MS (FAB) m/z: 487 (M+H)⁺.

¹H-NMR (CDCl₃): δ 8.44 (0.6H, s), 8.11 (0.4H, s), 7.78-7.88 (2H, m), 7.26-7.32 (4H, m), 7.06-7.16 (2H, m), 5.63 (0.6H, dd, J=3.6, 12.3 Hz), 5.38 (0.4H, dd, J=3.0, 10.1 Hz), 4.75 (2H, m), 4.18 (0.4H, dd, J=10.1, 15.7 Hz), 4.03 (0.6H, dd, J=12.3, 14.6 Hz), 3.72 (2H, q, J=6.9 Hz), 3.64-3.70 (4H, m), 3.41-3.48 (3H, m), 2.36-2.43 (4H, m), 1.24 (3H, t, J=6.9 Hz).

According to the schemes 1 to 4 and according to the same process as in Examples 1 to 7, the following compounds (I-8 to I-28) were obtained.

Example 8

N-[2-(4-But-2-ynyloxybenzenesulfonyl)-1-(4-dimethylaminophenyl)ethyl]-N-hydroxyformamide (I-8)

[Chem. 24]

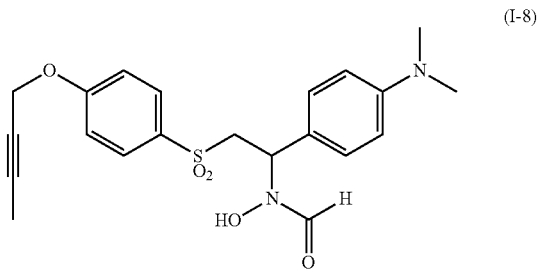

(I-8)

MS (ESI) m/z: 417(M+H)⁺.

¹H-NMR (CDCl₃): δ 8.40 (0.5H, s), 8.04 (0.5H, s), 7.73-7.89 (2H, m), 7.02-7.22 (4H, m), 6.62 (2H, d, J=8.7 Hz), 5.49-5.58 (0.5H, m), 5.22-5.31 (0.5H, m), 4.73 (2H, d, J=9.2 Hz), 3.98-4.23 (1H, m), 3.37-3.55 (1H, m), 2.93 (3H, s), 2.91 (3H, s), 1.87 (3H, t, J=2.3 Hz).

Example 9

N-[2-(4-But-2-ynyloxybenzenesulfonyl)-1-(3-dimethylaminophenyl)ethyl]-N-hydroxyformamide (I-9)

[Chem. 25]

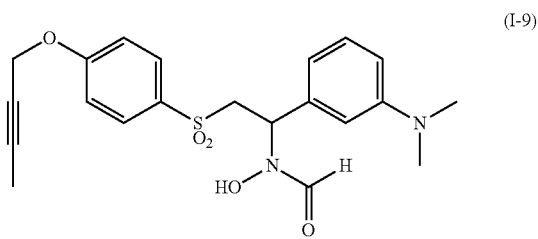

(I-9)

MS (ESI) m/z: 417(M+H)⁺.

¹H-NMR (CDCl₃): δ 8.45 (0.5H, s), 8.07 (0.5H, s), 7.77-7.89 (2H, m), 7.04-7.21 (4H, m), 6.57-6.68 (2H, m), 5.54-

5.62 (0.5H, m), 5.27-5.34 (0.5H, m), 4.69-4.77 (2H, m), 4.00-4.25 (1H, m), 3.41-3.54 (1H, m), 2.90-2.95 (6H, m), 1.87 (3H, t, J=2.3 Hz).

Example 10

N-[2-(4-But-2-ynyloxybenzenesulfonyl)-1-(2-dimethylaminophenyl)ethyl]-N-hydroxyformamide (I-10)

[Chem. 26]

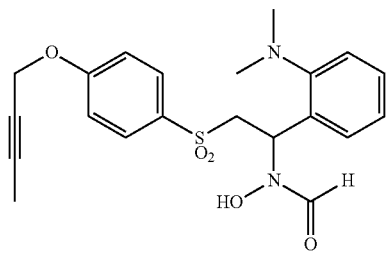

(I-10)

MS (ESI) m/z: 417(M+H)$^+$.

$^1$H-NMR (CDCl$_3$): δ 8.31 (0.6H, s), 8.08 (0.4H, s), 7.88 (0.6H, d, J=9.2 Hz), 7.83 (0.4H, d, J=8.7 Hz), 7.07-7.42 (6H, m), 6.57-6.68 (2H, m), 6.04 (0.4H, dd, J=2.7, 10 Hz), 5.88 (0.6H, dd, J=2.7, 11 Hz), 4.71-4.78 (2H, m), 3.99-4.08 (1H, m), 3.39-3.51 (1H, m), 2.61 (2.4H, s), 2.54 (3.6H, s), 1.86 (3H, t, J=2.3 Hz).

Example 11

N-[2-(4-But-2-ynyloxybenzenesulfonyl)-1-(4-piperidin-1-ylmethylphenyl)ethyl]-N-hydroxyformamide (I-11)

[Chem. 27]

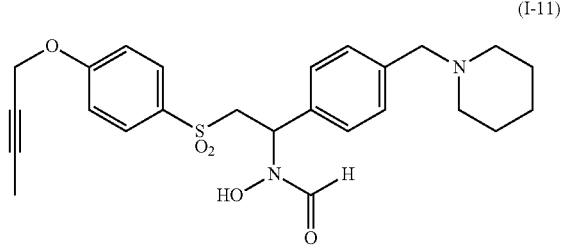

(I-11)

MS (ESI) m/z: 471(M+H)$^+$.

$^1$H-NMR (CDCl$_3$): δ 8.28 (0.6H, s), 8.10 (0.4H, s), 7.77-7.89 (2H, m), 7.04-7.30 (6H, m), 5.61-5.69 (0.6H, m), 5.31-5.39 (0.4H, m), 4.69-4.78 (2H, m), 3.99-4.26 (1H, m), 3.35-3.53 (3H, m), 2.37 (4H, br s), 1.87 (3H, br s), 1.35-1.59 (6H, m).

Example 12

N-[2-(4-But-2-ynyloxybenzenesulfonyl)-1-(3-piperidin-1-ylmethylphenyl)ethyl]hydroxyformamide (I-12)

[Chem. 28]

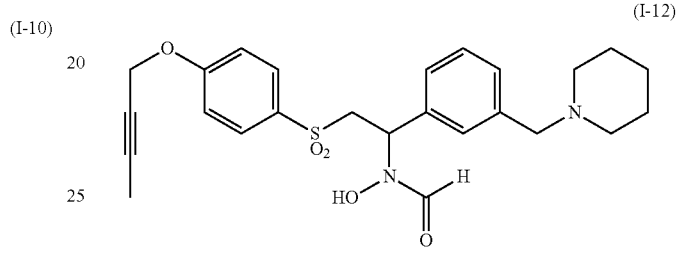

(I-12)

MS (ESI) m/z: 471(M+H)$^+$.

$^1$H-NMR (CDCl$_3$): δ 8.38 (0.5H, s), 8.10 (0.5H, s), 7.77-7.89 (2H, m), 7.04-7.30 (6H, m), 5.70 (0.5H, dd, J=3.7, 11 Hz), 5.30-5.38 (0.5H, m), 4.69-4.77 (2H, m), 4.01-4.27 (1H, m), 3.23-3.60 (3H, m), 2.30 (4H, br s), 1.87 (3H, t, J=2.3 Hz), 1.31-1.55 (6H, m).

Example 13

N-[2-(4-But-2-ynyloxybenzenesulfonyl)-1-(3-morpholin-4-ylmethylphenyl)ethyl]-N-hydroxyformamide (I-13)

[Chem. 29]

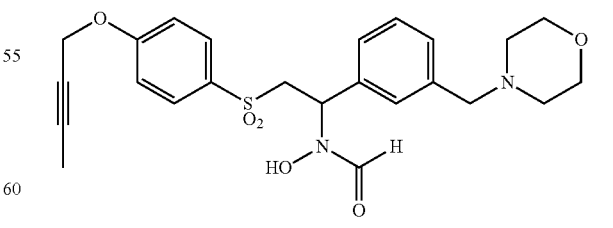

(I-13)

MS (ESI) m/z: 473(M+H)$^+$.

$^1$H-NMR (CDCl$_3$): δ 8.46 (0.5H, s), 8.10 (0.5H, s), 7.78-7.90 (2H, m), 7.06-7.31 (6H, m), 5.65 (0.5H, dd, J=3.7, 12 Hz), 5.35-5.42 (0.5H, m), 4.70-4.78 (2H, m), 3.98-4.26 (1H, m), 3.68 (4H, dd, J=4.6, 4.6 Hz), 3.39-3.54 (3H, m), 2.36-2.44 (4H, m), 1.87 (3H, t, J=2.3 Hz).

Example 14

N-[2-(4-But-2-ynyloxybenzenesulfonyl)-1-{4-[(ethylmethylamino)methyl]phenyl]ethyl}-N-hydroxyformamide (I-14)

[Chem. 30]

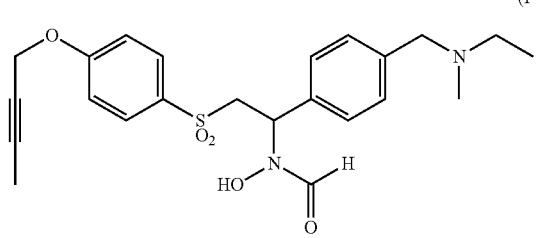

(I-14)

MS (ESI) m/z: 445(M+H)$^+$.

$^1$H-NMR (CDCl$_3$): δ 8.35 (0.5H, s), 8.11 (0.5H, s), 7.78-7.89 (2H, m), 7.06-7.28 (6H, m), 5.65 (0.5H, dd, J=3.7, 12 Hz), 5.32-5.40 (0.5H, m), 4.71-4.77 (2H, m), 3.99-4.24 (1H, m), 3.38-3.53 (3H, m), 2.38 (3H, q, J=7.3 Hz), 1.87 (3H, t, J=2.3 Hz), 1.05 (3H, t, J=7.3 Hz).

Example 15

N-(2-(4-But-2-ynyloxybenzenesulfonyl)-1-{3-[(ethylmethylamino)methyl]phenyl}ethyl)-N-hydroxyformamide (I-15)

[Chem. 31]

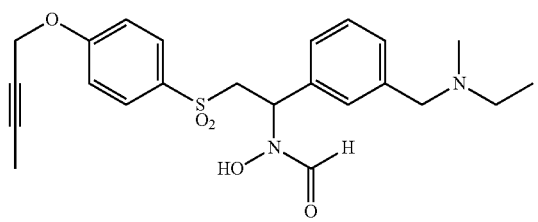

(I-15)

MS (ESI) m/z: 445(M+H)$^+$.

$^1$H-NMR (CDCl$_3$): δ 8.37 (0.5H, s), 8.11 (0.5H, s), 7.78-7.90 (2H, m), 7.06-7.34 (6H, m), 5.70 (0.5H, dd, J=3.7, 12 Hz), 5.32-5.40 (0.5H, m), 4.70-4.78 (2H, m), 4.00-4.22 (1H, m), 3.29-3.59 (3H, m), 2.38 (3H, q, J=6.9 Hz), 1.87 (3H, t, J=2.3 Hz), 1.03 (3H, t, J=6.9 Hz).

Example 16

N-{4-[2-(4-But-2-ynyloxybenzenesulfonyl)-1-(formylhydroxyamino)ethyl]benzyl}-N-methylmethanesulfonamide (I-16)

[Chem. 32]

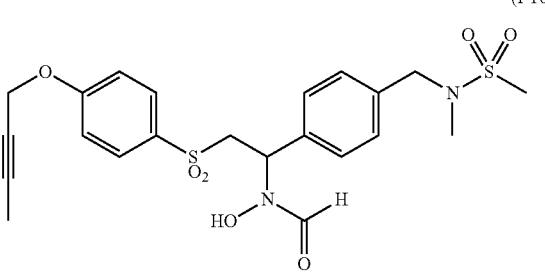

(I-16)

MS (ESI) m/z: 495(M+H)$^+$.

$^1$H-NMR (DMSO-d$_6$): δ 8.22 (0.5H, br s), 8.11 (0.5H, br s), 7.75-7.86 (2H, m), 7.09-7.42 (4H, m), 7.13 (2H, d, J=9.2 Hz), 5.70 (0.5H, br s), 5.40 (0.5H, br s), 4.83-4.89 (2H, m), 4.18 (2H, s), 3.86-4.16 (2H, m), 2.94 (3H, s), 2.63 (3H, s), 1.84 (3H, t, J=2.3 Hz).

Example 17

N-{4-[2-(4-But-2-ynyloxybenzenesulfonyl)-1-(formylhydroxyamino)ethyl]benzyl}-N-methylbenzenesulfonamide (I-17)

[Chem. 33]

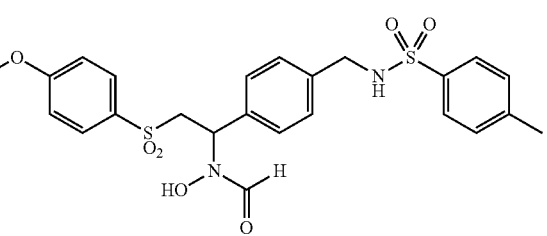

(I-17)

MS (ESI) m/z: 557(M+H)$^+$.

$^1$H-NMR (CDCl$_3$): δ 8.37 (0.6H, br s), 8.03 (0.4H, br s), 7.69-7.88 (4H, m), 7.04-7.33 (8H, m), 5.61 (0.6H, dd, J=3.6,

12 Hz), 5.31-5.39 (0.4H, m), 4.70-4.83 (2H, m), 3.92-4.17 (3H, m), 3.36-3.51 (1H, m), 2.43 (3H, s), 1.87 (3H, t, J=2.3 Hz).

Example 18

N-{4-[2-(4-But-2-ynyloxybenzenesulfonyl)-1-(formylhydroxyamino)ethyl]benzyl}-4,N-dimethyl-benzenesulfonamide (I-18)

[Chem. 34]

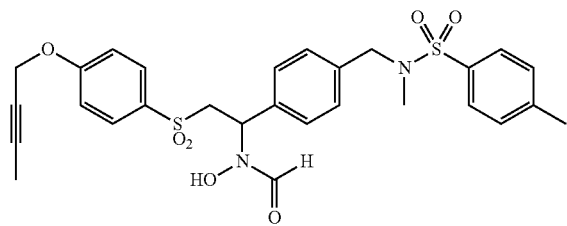

(I-18)

MS (ESI) m/z: 571(M+H)$^+$.

$^1$H-NMR (CDCl$_3$): δ 8.47 (0.6H, br s), 8.11 (0.4H, br s), 7.78-7.89 (2H, m), 7.70 (2H, d, J=8.2 Hz), 7.35 (2H, d, J=8.2 Hz), 7.23-7.32 (4H, m), 7.06-7.17 (2H, m), 5.64 (0.6H, dd, J=3.6, 12 Hz), 5.36-5.43 (0.4H, m), 4.71-4.78 (2H, m), 3.96-4.22 (3H, m), 3.38-3.52 (1H, m), 2.58 (1.2H, s), 2.54 (1.8H, s), 2.45 (3H, s), 1.87 (3H, t, J=2.3 Hz).

Example 19

N-{4-[2-(4-But-2-ynyloxybenzenesulfonyl)-1-(formylhydroxyamino)ethyl]benzyl}-N-methylsulfonylmethanesulfonamide (I-19)

[Chem. 35]

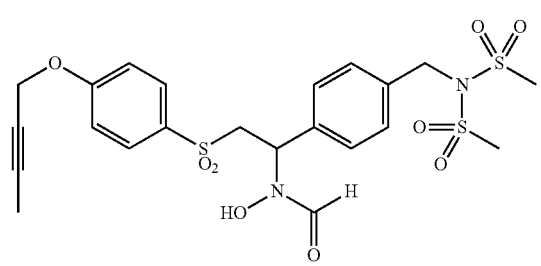

(I-19)

MS (ESI) m/z: 559(M+H)$^+$.

$^1$H-NMR (DMSO-d$_6$): δ 8.12 (0.5H, br s), 8.21 (0.5H, br s), 7.80 (2H, br s), 7.35-7.44 (1H, m), 7.32 (2H, d, J=9.2 Hz), 7.31 (1H, s), 7.14 (2H, d, J=9.2 Hz), 5.41 (0.5H, br s), 5.71 (0.5H, br s), 4.87 (2H, q, J=2.3 Hz), 4.83 (2H, s), 4.00-4.16 (1H, m), 3.84-3.98 (1H, m), 3.25 (6H, s), 1.84 (3H, t, J=2.3 Hz).

Example 20

N-{2-(4-But-2-ynyloxybenzenesulfonyl)-1-[4-(2-dimethylaminoethyl)phenyl]ethyl}-N-hydroxyformamide (I-20)

[Chem. 36]

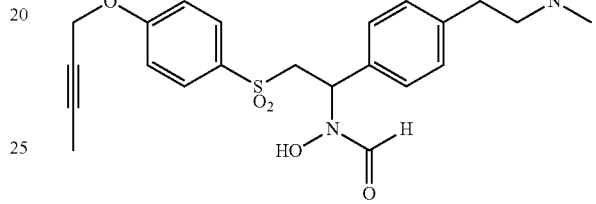

(I-20)

MS (ESI) m/z: 445(M+H)$^+$.

$^1$H-NMR (CDCl$_3$): δ 8.30 (0.5H, s), 8.14 (0.5H, s), 7.76-7.89 (2H, m), 7.00-7.24 (6H, m), 5.71 (0.5H, dd, J=3.7, 11 Hz), 5.29-5.36 (0.5H, m), 4.69-4.76 (2H, m), 4.02-4.21 (1H, m), 3.42-3.59 (1H, m), 2.43-2.54 (2H, m), 2.10-2.28 (2H, m), 2.19 (6H, s), 1.87 (3H, t, J=2.3 Hz).

Example 21

N-{2-(4-But-2-ynyloxybenzenesulfonyl)-1-[4-(2-morpholin-4-ylethyl)phenyl]ethyl}-N-hydroxyformamide (I-21)

[Chem. 37]

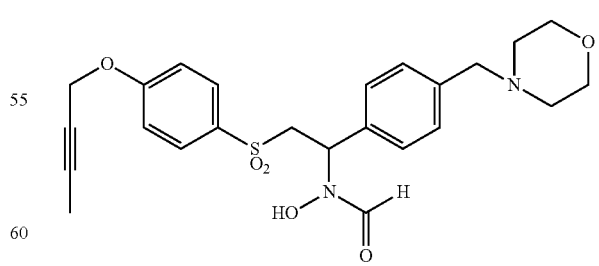

(I-21)

MS (ESI) m/z: 487(M+H)$^+$.

$^1$H-NMR (CDCl$_3$): δ 8.44 (0.5H, s), 8.10 (0.5H, s), 7.77-7.89 (2H, m), 7.05-7.27 (6H, m), 5.62 (0.5H, dd, J=3.7, 12 Hz), 5.32-5.39 (0.5H, m), 4.69-4.78 (2H, m), 3.96-4.23 (1H, m), 3.71 (4H, dd, J=4.1, 4.6 Hz), 3.39-3.53 (1H, m), 2.69-2.77 (2H, m), 2.43-2.56 (6H, m), 1.87 (3H, t, J=2.3 Hz).

Example 22

N-(2-{4-[2-(4-But-2-ynyloxybenzenesulfonyl)-1-(formylhydroxyamino)ethyl]phenyl}ethyl)methanesulfonamide (I-22)

[Chem. 38]

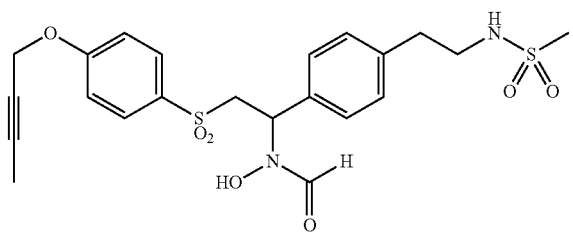

(I-22)

MS (ESI) m/z: 495(M+H)$^+$.

$^1$H-NMR (CDCl$_3$): δ 8.39 (0.5H, s), 8.07 (0.5H, s), 7.78-7.89 (2H, m), 7.05-7.30 (6H, m), 5.65 (0.5H, dd, J=3.7, 12 Hz), 5.33-5.41 (0.5H, m), 4.70-4.78 (2H, m), 3.95-4.21 (1H, m), 3.31-3.52 (3H, m), 2.80-2.91 (5H, m), 1.87 (3H, t, J=2.3 Hz).

Example 23

N-{2-(4-But-2-ynyloxybenzenesulfonyl)-1-[4-(3-dimethylaminopropyl)phenyl]ethyl}-N-hydroxyformamide (I-23)

[Chem. 39]

(I-23)

MS (ESI) m/z: 459(M+H)$^+$.

$^1$H-NMR (CDCl$_3$): δ 8.06-8.13 (1H, m), 7.74-7.88 (2H, m), 7.02-7.24 (6H, m), 5.64-5.75 (0.5H, m), 5.22-5.32 (0.5H, m), 4.68-4.76 (2H, m), 4.02-4.22 (1H, m), 3.40-3.58 (1H, m), 2.51 (2H, dd, J=7.3, 7.8 Hz), 2.17 (2H, dd, J=7.3, 7.8 Hz), 2.08 (3H, s), 2.06 (3H, s), 1.87 (3H, t, J=2.3 Hz), 1.52-1.66 (2H, m).

Example 24

N-{2-(4-But-2-ynyloxybenzenesulfonyl)-1-[4-(3-diethylaminopropyl)phenyl]ethyl}-N-hydroxyformamide (I-24)

[Chem. 40]

(I-24)

MS (ESI) m/z: 487(M+H)$^+$.

$^1$H-NMR (CDCl$_3$): δ 8.29 (0.5H, s), 8.07 (0.5H, m), 7.75-7.89 (2H, m), 7.04-7.24 (6H, m), 5.64 (0.5H, dd, J=3.7, 11 Hz), 5.28-5.37 (0.5H, m), 4.69-4.77 (2H, m), 4.00-4.23 (1H, m), 3.41-3.55 (1H, m), 2.33-2.60 (6H, m), 1.87 (3H, t, J=2.3 Hz), 1.61-1.72 (2H, m), 0.91-1.01 (6H, m).

Example 25

N-{2-(4-But-2-ynyloxybenzenesulfonyl)-1-[4-(3-morpholin-4-ylpropyl)phenyl]ethyl}-N-hydroxyformamide (I-25)

[Chem. 41]

(I-25)

MS (ESI) m/z: 501 (M+H)$^+$.

$^1$H-NMR (CDCl$_3$): δ 8.37 (0.5H, s), 8.08 (0.5H, s), 7.76-7.89 (2H, m), 7.04-7.24 (6H, m), 5.64 (0.5H, dd, J=3.7, 12 Hz), 5.29-5.38 (0.5H, m), 4.68-4.77 (2H, m), 3.98-4.23 (1H, m), 3.67 (4H, br s), 3.40-3.53 (1H, m), 2.52-2.63 (2H, m), 2.24-2.46 (6H, m), 1.87 (3H, t, J=2.3 Hz), 1.65-1.76 (2H, m).

Example 26

N-{2-(4-But-2-ynyloxybenzenesulfonyl)-1-[4-(4-morpholin-4-ylbutyl)phenyl]ethyl}-N-hydroxyformamide (I-26)

[Chem. 42]

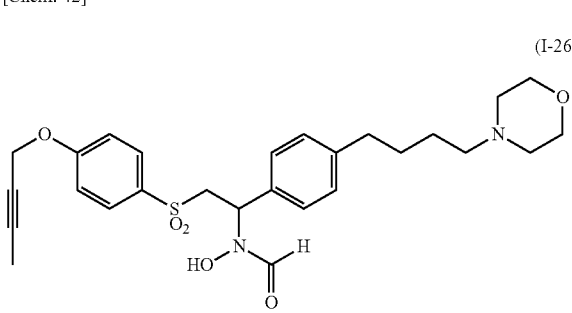

(I-26)

MS (ESI) m/z: 515(M+H)$^+$.

$^1$H-NMR (CDCl$_3$): δ 8.41 (0.5H, s), 8.10 (0.5H, s), 7.77-7.89 (2H, m), 7.05-7.24 (6H, m), 5.57-5.66 (0.5H, m), 5.31-5.38 (0.5H, m), 4.69-4.77 (2H, m), 3.97-4.23 (1H, m), 3.67 (4H, dd, J=4.1, 4.6 Hz), 3.40-3.53 (1H, m), 2.52-2.63 (2H, m), 2.24-2.46 (6H, m), 1.87 (3H, t, J=2.3 Hz), 1.39-1.63 (4H, m).

Example 27

N-{4-[1-(Formylhydroxyamino)-2-(4-pent-2-ynyloxybenzenesulfonyl)ethyl]benzyl}methanesulfonamide (I-27)

[Chem. 43]

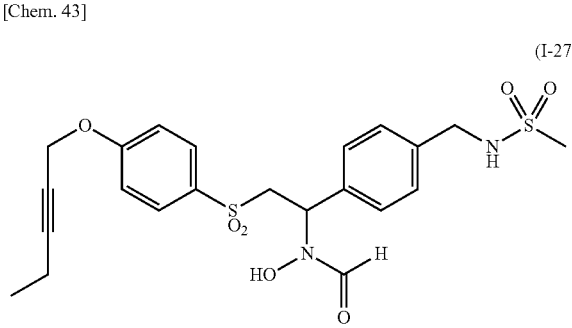

(I-27)

MS (ESI) m/z: 495(M+H)$^+$.

$^1$H-NMR (CDCl$_3$): δ 8.29 (0.6H, s), 8.00 (0.4H, s), 7.75-7.88 (2H, m), 7.23-7.35 (4H, m), 7.05-7.16 (2H, m), 5.66 (0.6H, dd, J=3.7, 12 Hz), 5.31-5.41 (0.4H, m), 4.71-4.80 (2H, m), 4.26 (2H, br s), 3.95-4.18 (1H, m), 3.39-3.50 (1H, m), 2.89 (3H, br s), 2.24 (2H, tq, J=1.8, 7.3 Hz), 1.14 (3H, t, J=7.3 Hz).

Example 28

N-{4-[1-(Formylhydroxyamino)-2-(4-oct-2-ynyloxybenzenesulfonyl)ethyl]benzyl}methanesulfonamide (I-28)

[Chem. 44]

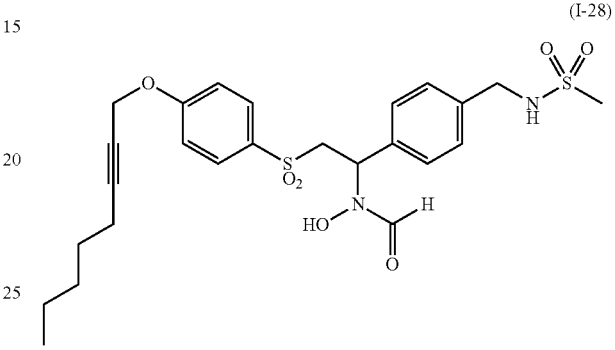

(I-28)

MS (ESI) m/z: 537(M+H)$^+$.

$^1$H-NMR (CDCl$_3$): δ 8.35 (0.6H, s), 8.03 (0.4H, s), 7.76-7.88 (2H, m), 7.27-7.36 (4H, m), 7.06-7.17 (2H, m), 5.66 (0.6H, dd, J=3.7, 12 Hz), 5.34-5.42 (0.4H, m), 4.72-4.82 (2H, m), 4.23-4.33 (2H, m), 3.94-4.18 (1H, m), 3.38-3.51 (1H, m), 2.90 (1.2H, s), 2.89 (1.8H, s), 2.22 (2H, tt, J=2.3, 7.3 Hz), 1.45-1.55 (2H, m), 1.23-1.38 (4H, m), 0.87 (3H, t, J=7.3 Hz).

Test Example 3

ADAM17 Inhibition Experiment

The N-hydroxyformamide derivatives obtained in Examples 1 to 7 were examined to determine whether they had an ADAM17 inhibitory action or not.

Specifically, first, since the nucleotide sequence coding for ADAM17 had been reported by Moss et al. (see Moss et al., Nature, 1997, vol. 385, pp. 733-736), the cDNA of ADAM-17 was obtained from a human monocytic cell line, THP-1 cells, by a standard method. The cDNA was incorporated into an expression vector. Then, this vector was transfected into mammalian cells or insect cells, and ADAM17 was expressed and obtained.

Next, the activity of ADAM17 was measured, as follows in the presence or absence of the test substances, in which obtained ADAM17 was used as an enzyme, and a fluorescent synthetic substrate Nma (N-methyl anthranilate)-Leu-Ala-Gln-Ala-Val-Arg-Ser-Ser-Lys-Dnp (dinitrophenyl)-D-Arg-NH$_2$ containing an ADAM17-cleavage sequence of membrane-bound TNF was used as a substrate.

Specifically, 90 μL of 14 units of an enzyme solution (1 unit is defined as an amount of enzyme degrading 1 μmol of the substrate in 1 minute at 25° C.) prepared with Assay Buffer A (50 mmol/L Tris-HCl buffer (pH 7.5) containing 200 mmol/L sodium chloride, 5 mmol/L calcium chloride, 10 μmol/L zinc sulfate, and 2 mg/mL bovine serum albumin) was mixed with 90 μL of the fluorescent synthetic substrate adjusted to be 20 μmol/L with Assay Buffer B (50 mmol/L Tris-HCl buffer (pH 7.5) containing 200 mmol/L sodium chloride, 5 mmol/L calcium chloride, 10 μmol/L zinc sulfate, and 0.05% PLURONIC F-68), and allowed for reaction at 37° C. for 1.5 hours. Thereafter, the enzyme activity was determined by measurement using a fluorometer (Fluoroskan Ascent) under conditions of an excitation wavelength of 355 nm and a measurement wavelength of 460 nm. Then, an inhibition rate was obtained based on the enzyme activities in the presence and absence of the test compounds, and the 50% inhibitory concentration ($IC_{50}$) was calculated. Table 1 show the obtained result.

TABLE 1

| Compound | IC50 (nmol/L) |
|---|---|
| I-1 | 5.2 |
| I-2 | 7.2 |
| I-3 | 8.2 |
| I-4 | 5.8 |
| I-5 | 7.2 |
| I-6 | 18 |
| I-7 | 55 |

As apparent from the result shown in Table 1, any of the compounds I-1 to I-7 (N-hydroxyformamide derivatives) according to the present invention was confirmed to inhibit the ADAM17-enzyme activity at low concentrations.

Test Example 4

Various Evaluation Experiments

Next, compounds I-1 (hereinafter also referred to as "S-45282") and I-4 (hereinafter also referred to as "S-45457") having a strong inhibitory effect on ADAM17 among the N-hydroxyformamide derivatives obtained in Examples 1 to 7 were examined for the specificity as an inhibitor and the TACE-inhibitory activity in cells by the following methods. For comparison, a non-selective metalloproteinase inhibitor GM6001 (EMD/Calbiochem, product number 364205) was also evaluated.

<Enzyme Inhibition Experiment>

Enzymes used in this test are as follow:
Matrix metalloproteinase 1 (MMP-1) (manufactured by Calbiochem, product number: 444208)
Matrix metalloproteinase 2 (MMP-2) (manufactured by Calbiochem, product number: 444213)
Matrix metalloproteinase 3 (MMP-3) (manufactured by Calbiochem, product number: 444217)
Matrix metalloproteinase 8 (MMP-8) (manufactured by Calbiochem, product number: 444229)
Matrix metalloproteinase 9 (MMP-9) (manufactured by Calbiochem, product number: 444231)
Matrix metalloproteinase 13 (MMP-13) (manufactured by Chemicon, product number: CC068)
Matrix metalloproteinase 14 (MMP-14) (manufactured by Calbiochem, product number: 475935)
Matrix metalloproteinase 17 (MMP-17) (manufactured by Calbiochem, product number: 475940)
A disintegrin and metalloproteinase 10 (ADAM10) (manufactured by Funakoshi Co., Ltd., product code: 936-AD-020) and
A disintegrin and metalloproteinase 17 (ADAM17, TACE) (used was one prepared at Kaken Pharmaceutical Co., Ltd. by employing the genetic recombination in the same way as in Test Example 3. Note that, the same as in Test Example 3, 1 unit is defined as an amount of enzyme degrading 1 pmol of substrate in 1 minute at 25° C.)

In addition, substrates used in this test are as follows:
444221 substrate (DNP-Pro-Cha-Gly-Cys(Me)-His-Ala-Lys(Nma)-$NH_2$, custom synthesis): excitation wavelength at 355 nm, emission wavelength at 460 nm
TACE substrate (the same as one used in Test Example 3): excitation wavelength at 355 nm, emission wavelength at 460 nm
3168 substrate (MOCAc-Arg-Pro-Lys-Pro-Val-Glu-Nva-Trp-Arg-Lys(Dnp)-$NH_2$, manufactured by Peptide Institute, Inc.): excitation wavelength at 320 nm, emission wavelength at 405 nm, and 3163 substrate (MOCAc-Pro-Leu-Gly-Leu-$A_2$pr(Dnp)-Ala-Arg-$NH_2$, manufactured by Peptide Institute, Inc.): excitation wavelength at 320 nm, emission wavelength at 405 nm.

The enzyme reaction was carried out using the enzymes and substrates. Specifically, if necessary, the enzyme was activated in advance with APMA (final concentration 1 mmol/L, p-aminophenylmercuric acetate, manufactured by Sigma-Aldrich Co., A9563) according to information from the manufacturer. Then, in a 96-well plate for fluorescence measurement, 90 μL of an enzyme solution prepared with Assay Buffer A (50 mmol/L Tris-HCl buffer (pH 7.5) containing 200 mmol/L sodium chloride, 5 mmol/L calcium chloride, 10 μmol/L zinc sulfate, and 2 mg/mL bovine serum albumin) was mixed with 90 μL of the substrate adjusted to be 20 μmol/L with Assay Buffer B (50 mmol/L Tris-HCl buffer (pH 7.5) containing 200 mmol/L sodium chloride, 5 mmol/L calcium chloride, 10 μmol/L zinc sulfate, and 0.05% PLURONIC F-68), and incubated for reaction at 25° C. or 37° C. for several hours. Moreover, the fluorescence intensities before and after the reaction were measured using a fluorometer to determine the enzyme activity. An inhibition rate was obtained based on the enzyme activities in the presence and absence of the test substances, and the 50% inhibitory concentration ($IC_{50}$) was calculated. Table 2 shows the reaction conditions for each enzyme.

TABLE 2

| | Amount of enzyme per reaction | Substrate (final concentration: 10 μmol/L) | Reaction |
|---|---|---|---|
| MMP-1 | 10 ng | 444221 substrate | 37° C., 5 hours |
| MMP-2 | 0.5 ng | 3163 substrate | 37° C., 5 hours |
| MMP-3 | 1.5 ng | 3168 substrate | 37° C., 4 hours |
| MMP-8 | 2.9 ng | 3163 substrate | 37° C., 5 hours |
| MMP-9 | 1.1 ng | 444221 substrate | 37° C., 4 hours |
| MMP-13 | 1.8 ng | 444221 substrate | 37° C., 4 hours |
| MMP-14 | 1.9 ng | 444221 substrate | 37° C., 5 hours |
| MMP-17 | 5.8 ng | 3163 substrate | 25° C., 5 hours |
| ADAM10 | 31.7 ng | TACE substrate | 25° C., 5 hours |
| ADAM17 | 14 units | TACE substrate | 37° C., 1.5 hours |

<Cellular TACE Inhibition Experiment>

THP-1 cells (human acute monocytic leukemia-derived cells, ATCC catalog number: TIB202) were suspended in 10 v/v % FBS-containing RPMI 1640, dispensed in a volume of 200 μL/well (1×$10^5$ cells) into a 96-well culture plate, treated with PMA (final concentration 50 nmol/L) and cultured at 37° C. in 5% $CO_2$ for 40 to 48 hours, so that the THP-1 cells differentiated into macrophage-like cells. After the differentiation, the medium was discarded, and the cells were washed with THP-1 washing buffer (RPMI 1640, 20 mM HEPES-NaOH (pH 7.4)). After the washing of the cells, a THP-1 assay buffer (RPMI 1640, 20 mmol/L HEPES-NaOH (pH 7.4), 0.01 w/v % PF-68, 10 v/v % FBS) was added thereto at 100 μL/well. Then, a THP-1 assay buffer containing the test substance (I-1 or I-4) was further added at 50 μL/well and mixed by tapping. After incubation in a $CO_2$ incubator for 30 to 45 minutes, a THP-1 assay buffer containing LPS was added at 50 μL/well (the final concentration of LPS was 1 μg/mL). Further, the plate was tapped for mixing, followed by incubation in the $CO_2$ incubator for 6 hours. After the incubation was finished, human TNF-α concentration in the culture supernatant was measured with a commercially available kit (Human TNF-α CytoSet (manufactured by BIOSOURCE) or Human TNF-α Ready-Set-Go! (manufactured by eBioscience, Inc.)).

Table 3 show the result obtained by these experimental methods.

After collection as described above, the number of CD41(+)CD42b(+), the number of CD41(+)CD42b(−), and a total number of platelets were counted by flow cytometry. FIGS. 7 to 10 show the obtained results. Note that since CD41 (integrin αIIb) is a surface marker for platelets, CD41(+) indicates platelets. Moreover, CD42b (GPIbα)(+) indicates that platelets have GPIbα on the surface, while CD42b (GPIbα)(−) indicates that platelets of which GPIbα was shed by ADAM17. In addition, in the graphs, "GM" shows the result of adding 50 μM GM6001 (solvent: DMSO), and "45282" shows the result of adding S-45282 (solvent: DMSO) at each concentration.

TABLE 3

| Compound | ADAM17 | MMP-1 | MMP-2 | MMP-3 | MMP-8 | MMP-9 | MMP-13 | MMP-14 | MMP-17 | ADAM10 | TNFα production |
|---|---|---|---|---|---|---|---|---|---|---|---|
| | | | | | IC50 (nmol/L) | | | | | | |
| GM 6001 | 310 | 4.0 | 0.23 | 32 | 0.06 | 0.28 | 0.26 | 1.6 | 3.0 | 410 | — |
| I-1 (S-45282) | 5.2 | >100000 | 150 | 8300 | 900 | 11000 | 550 | 1000 | 2800 | 13 | 1200 |
| I-4 (S-45457) | 5.8 | >100000 | 290 | 6500 | 950 | 11000 | 700 | 1400 | 3400 | 40 | 625 |

As apparent from the result shown in Table 3, both of the compounds I-1 and I-4 according to the present invention were confirmed to have a high specificity to ADAM17 in comparison with metalloproteinases other than ADAM17. Their inhibitory activity was confirmed on TACE expressed on the macrophage-like cells, also. Moreover, the two compounds suppressed ADAM10, as well, although the degree of suppression was somewhat low in comparison with ADAM17. ADAM10 is an enzyme that can cleave the same substrate as ADAM17 (see Caescu et al., Biochemical J., 2009, vol. 424, pp. 79 to 88). It is suggested that the inhibition is useful for storing the platelet function (see Bender et al., "Differentially regulated GPVI ectodomain shedding by multiple platelet-expressed proteinases.," Blood, Jul. 19, 2010, online publication). From the above, the compounds I-1 and I-4 according to the present invention are ADAM17-specific inhibitors, suggesting that the other compounds having the same basic structure (for example, I-2, I-3, I-5, I-6) according to the present invention be also ADAM17-specific inhibitors. Meanwhile, GM6001 having a hydroxamic acid structure non-specifically and strongly inhibited metalloproteinases as has been known conventionally, but the inhibitory activity on ADAM17 was weak.

Test Example 5

Figure 6:
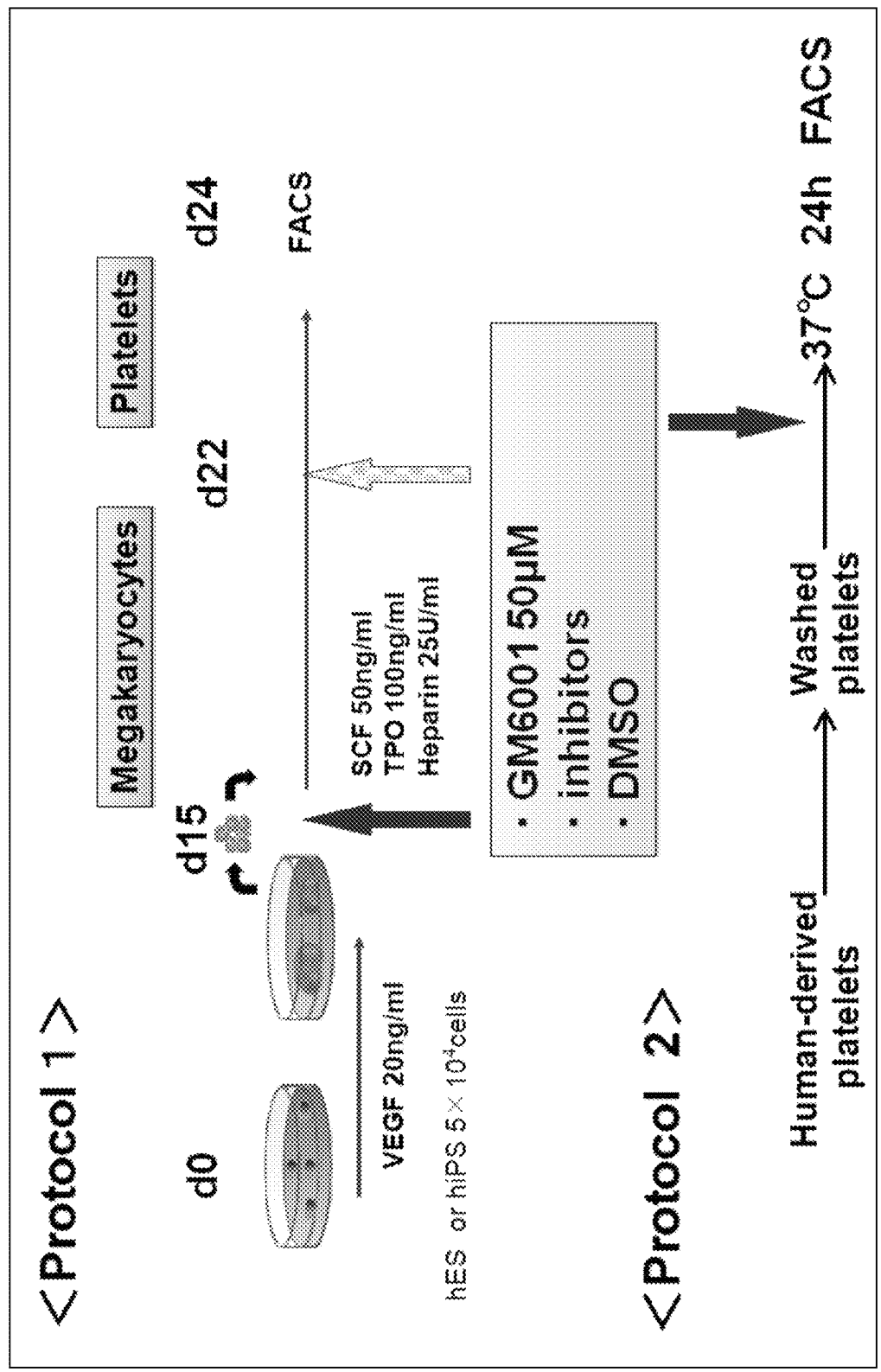
FIG. 6 <Protocol 1> illustrates application timing of a compound (S-45282 or S-45457) according to the present invention in an induction process from ES cell- or iPS cell-derived hematopoietic progenitor cells into megakaryocytes/platelets. <Protocol 2> illustrates that washed platelets were prepared from human peripheral blood, and the compound (S-45282 or S-45457) according to the present invention was added thereto.

Verification of Function-Maintaining Effects of GM6001 and S-45282 on ES Cell-Derived Platelets Under conditions (Protocol 1) illustrated in FIG. 6, platelets were induced from ES cell-derived hematopoietic progenitor cells obtained as described above. Specifically, in the above-described 8-day culture process for inducing hematopoietic progenitor cells to megakaryocytes/platelets, culturing was conducted under the following conditions:
2 days: culturing while GM6001, S-45282, or DMSO was added 2 days before the flow cytometry analysis (on "d22" shown in FIG. 6), or
8 days: culturing for 8 days while GM6001 (50 μM), S-45282 (5 μM or 50 μM), or DMSO was added after ES cell-derived hematopoietic progenitor cells were reseeded (after "d15" shown in FIG. 6).

Figure 7:
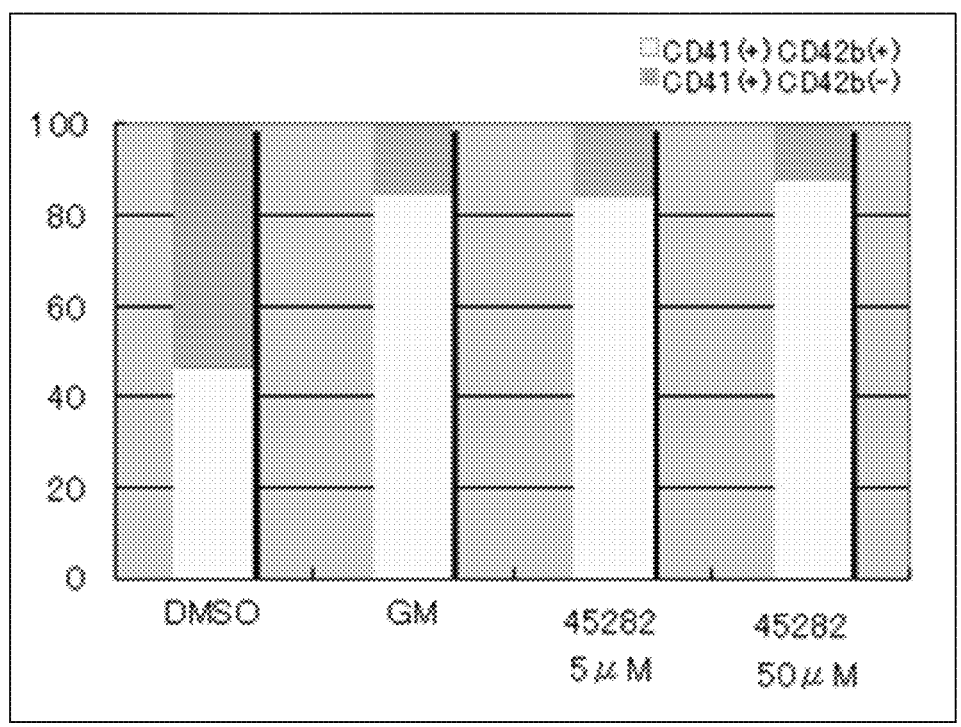
FIG. 7 is a graph for illustrating the results of verification of the function-maintaining effects of GM6001 and S-45282 on ES cell-derived platelets when each compound was added to a culture system for 2 days (2 days). The vertical axis represents percentages (%) of CD42b (GPIbα)(+) and CD42b (GPIbα)(−) where a total number of platelets (CD41(+)) is taken as 100.
Figure 9:
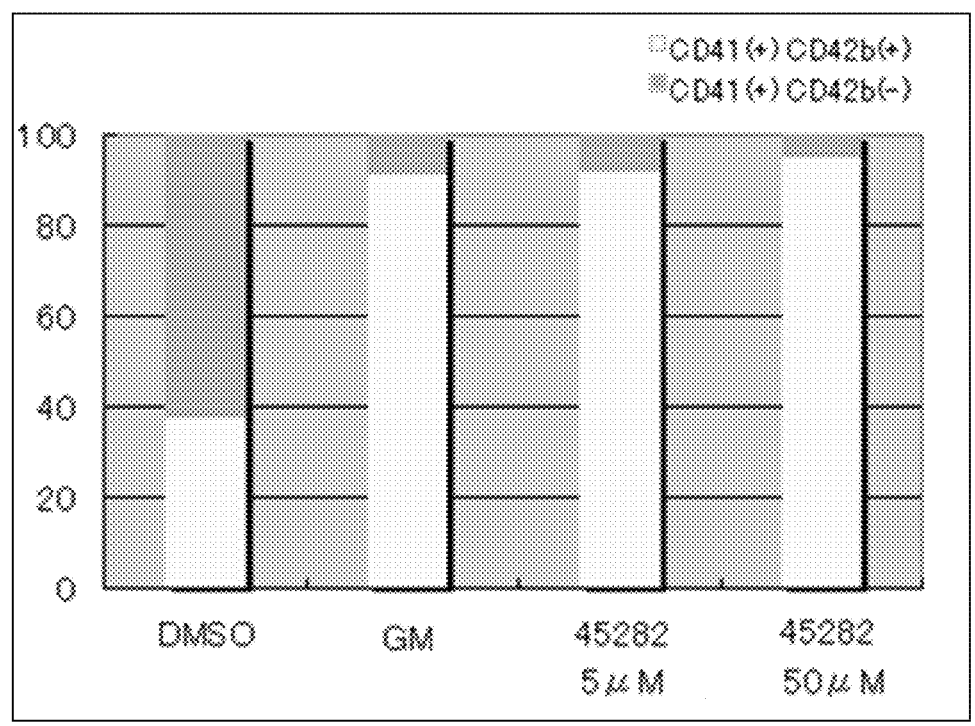
FIG. 9 is a graph for illustrating the result of verifying effects of GM6001 and S-45282 maintaining a function of ES cell-derived platelets when each compound was added to a culture system for 8 days (8 days). The vertical axis represents percentages (%) of CD42b (GPIbα)(+) and CD42b (GPIbα) (−) where a total number of platelets (CD41(+)) is taken as 100.

After collection as described above, the number of CD41(+)CD42b(+), the number of CD41(+)CD42b(−), and a total number of platelets were counted by flow cytometry. FIGS. 7 and 9, it was confirmed that each of GM6001 and S-45282 inhibit ADAM17-mediated GPIbα shedding. Further, it was also revealed that S-45282 even at a concentration of 5 μM has an inhibitory effect equivalent to 50 μM GM6001.

Figure 8:
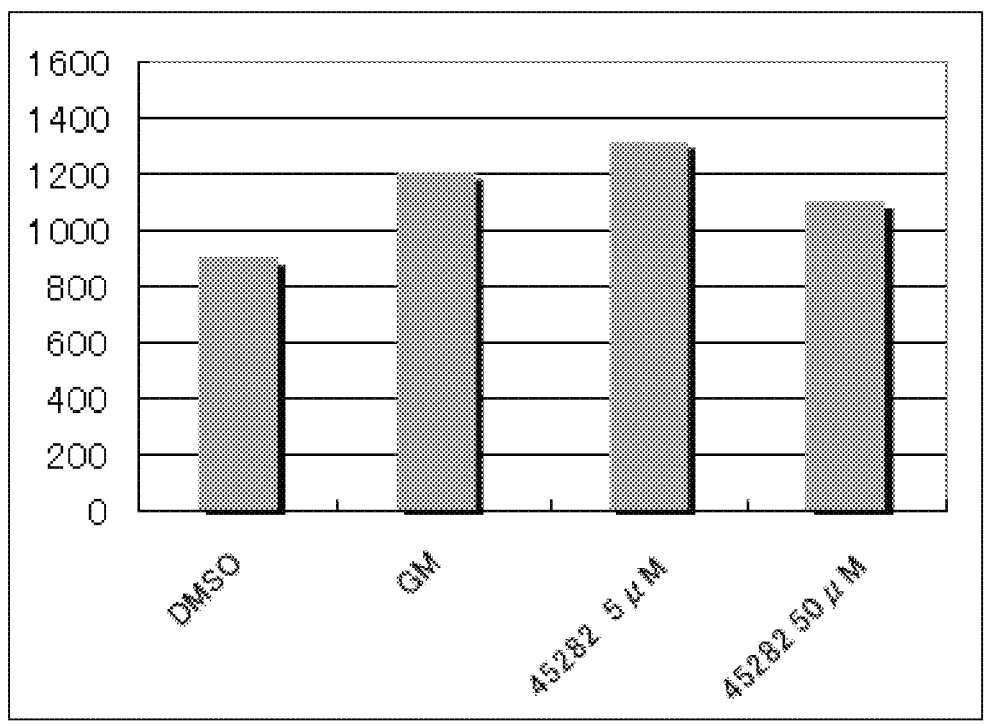
FIG. 8 is a graph showing a total number of the ES cell-derived platelets obtained when GM6001 or S-45282 was added to the culture system for 2 days (2 days). The unit of the vertical axis is cell count/well.
Figure 10:
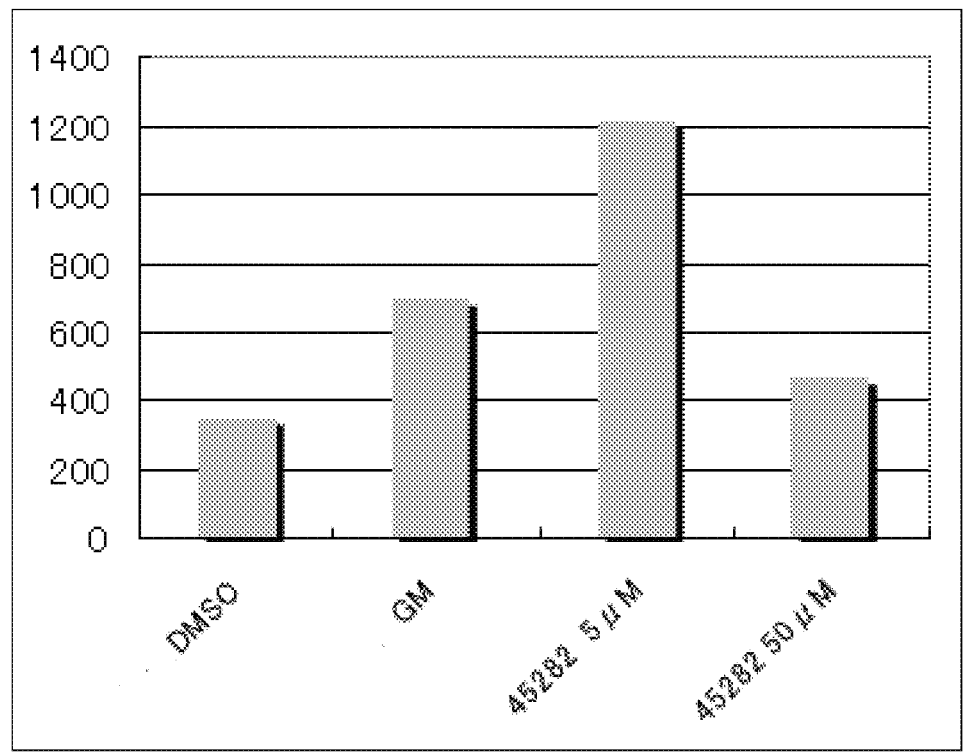
FIG. 10 is a graph showing a total number of the ES cell-derived platelets obtained when GM6001 or S-45282 were added to the culture system for 8 days (8 days). The unit of the vertical axis is cell count/well.

In addition, as apparent from the results shown in FIGS. 8 and 10, the number of platelets obtained was approximately the same when 50 μM GM6001 and 5 μM S-45282 were added for 2 days; meanwhile, in the 8-day addition, GM6001 produced fewer platelets than 5 μM S-45282, revealing that 50 μM GM6001 had cytotoxicity.

Test Example 6

Figure 11:
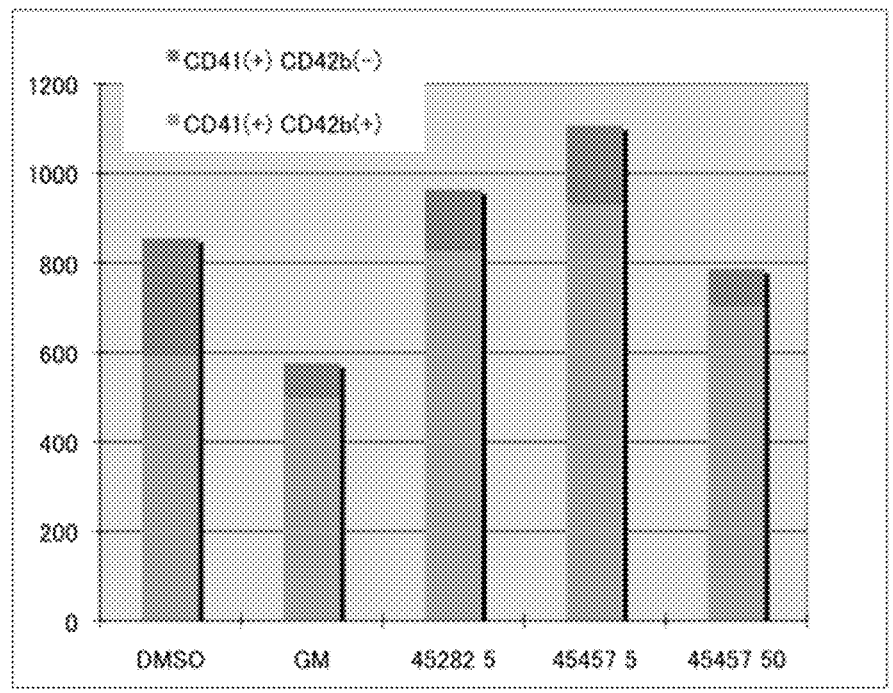
FIG. 11 is a graph showing the number of ES cell-derived platelets (the number of CD41(+)CD42b(+) and CD41(+)CD42b(−)) obtained when GM6001, S-45282, or S-45457 was added to a culture system for 8 days. The unit of the vertical axis is cell count/well.
Figure 12:
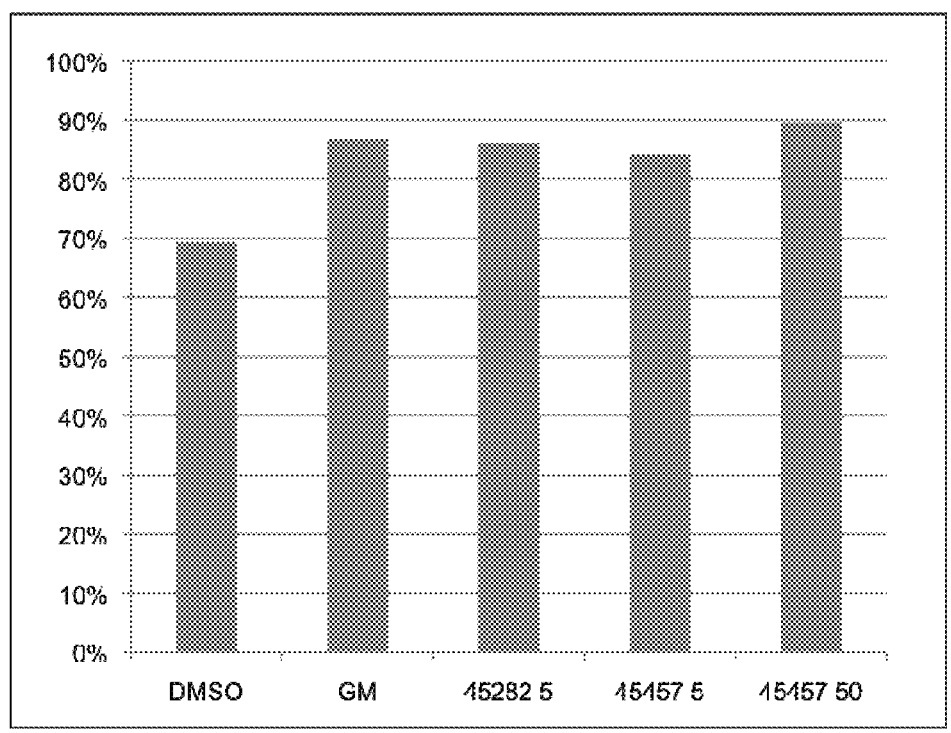
FIG. 12 is a graph for illustrating the result of verification of function-maintaining effects of GM6001, S-45282, and S-45457 on the ES cell-derived platelets when each compound was added to the culture system for 8 days. The vertical axis represents a percentage (%) of CD42b (GPIbα)(+) where a total number of platelets (CD41(+)) is taken as 100.
Figure 13:
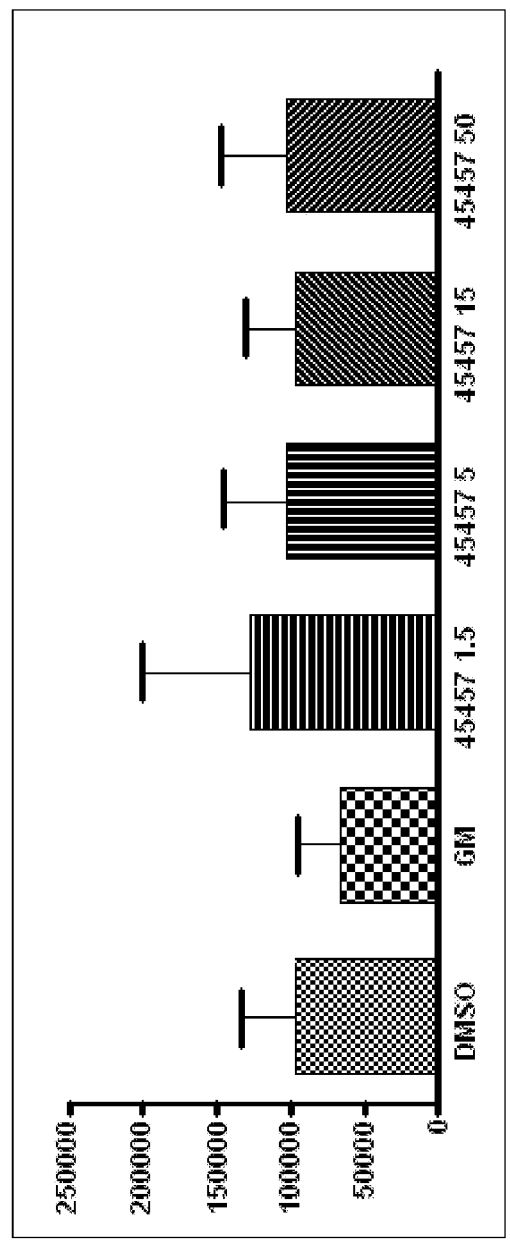
FIG. 13 is a graph showing a total number of ES cell-derived platelets obtained when GM6001 or S-45457 was added to a culture system for 8 days. The unit of the vertical axis is cell count/well. The value is average+standard error (n=4).

Verification of Function-Maintaining Effects of S-45457 and S-45282 on ES Cell-Derived Platelets Under the conditions (Protocol 1) illustrated in FIG. 6, platelets were induced from ES cell-derived hematopoietic progenitor cells obtained as described above. Specifically, after ES cell-derived hematopoietic progenitor cells were reseeded (after "d15" shown in FIG. 6), one of either GM6001 (50 μM), S-45457 (5 μM or 50 μM), S-45282 (5 μM), or DMSO was added, followed by culturing for 8 days. After collection as described above, the number of CD41(+)CD42b(+), the number of CD41(+)CD42b(−), and a total number of platelets were counted by flow cytometry. FIGS. 11 and 12 show the obtained results. Note that, in the graphs, "45457" shows the result of adding S-45457 (solvent: DMSO) at each concentration.

As apparent from the results shown in FIGS. 11 and 12, it was confirmed that S-45457 also inhibits ADAM17-mediated GPIbα shedding, similarly to GM6001 and S-45282.

Test Example 7

Verification of Concentration Dependency of Function-Maintaining Effect of S-45457 on Platelets Under the conditions illustrated in FIG. 6, platelets were induced from ES cells- or iPS cell-derived hematopoietic progenitor cells obtained as described above. Specifically, after ES cell- or iPS cell-derived hematopoietic progenitor cells were reseeded (after "d15" shown in FIG. 6), GM6001 (50 µM), S-45457 (1.5 to 50 µM), or DMSO was added, followed by culturing for 8 days. After collection as described above, the number of CD41(+)CD42b (+), the number of CD41(+)CD42b(−), and a total number of platelets were counted by flow cytometry. FIGS. 13 to 16 show the result obtained by conducting the above procedure 4 times. Note that the statistical analysis of rates of CD42b(+) to the total number of platelets was performed by ANOVA on angular-transformed values, followed by multiple comparisons of Dunnett's test on a group difference between the DMSO group and the test substance groups.

Figure 14:
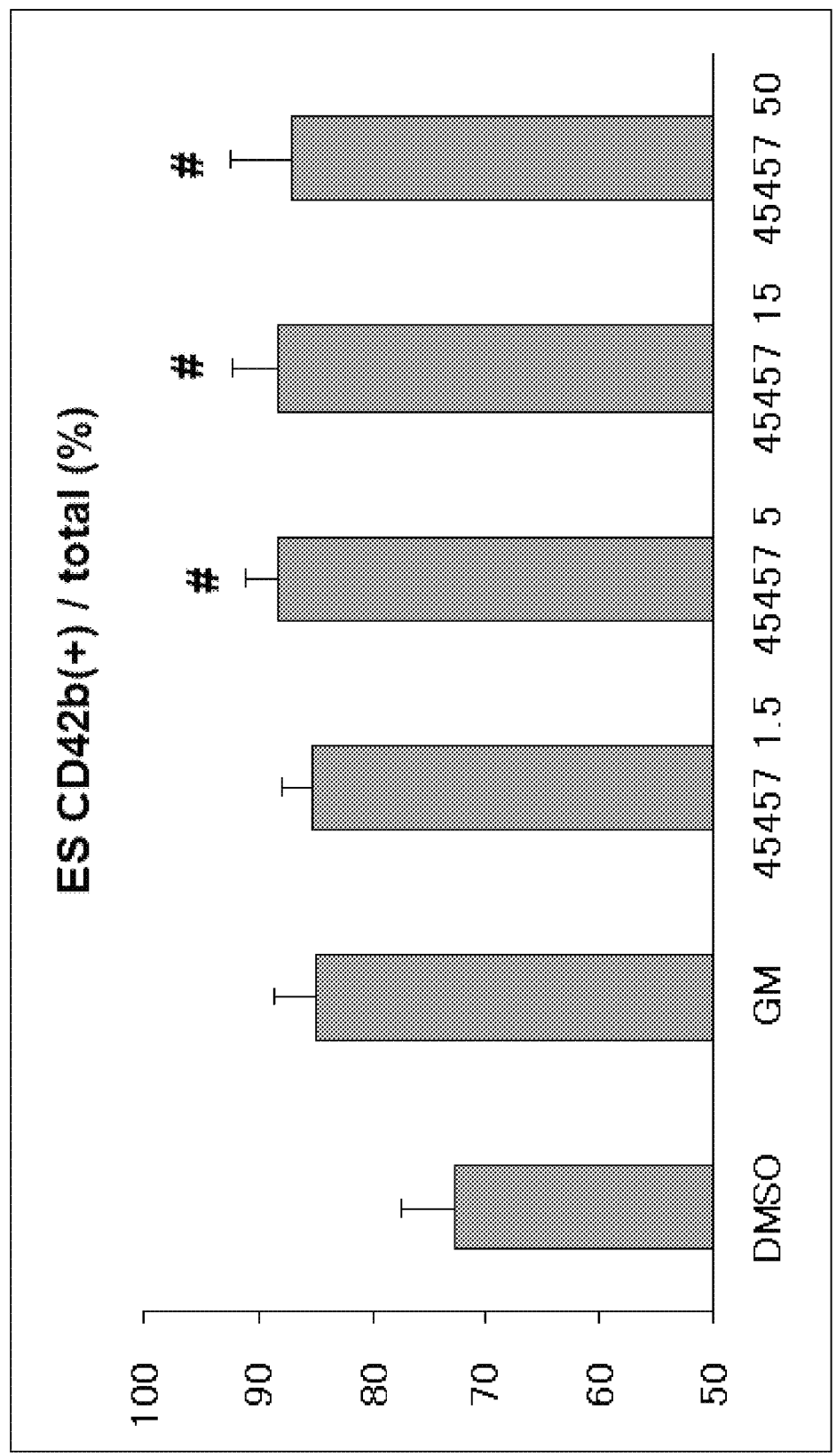
FIG. 14 is a graph for illustrating a concentration-dependence of function-maintaining effect of S-45457 on the ES cell-derived platelets. The vertical axis represents a percentage (%) of CD42b (GPIbα)(+) where a total number of platelets is taken as 100. The value is average+standard error (n=4). # (sharp sign) indicates p<0.1.
Figure 15:
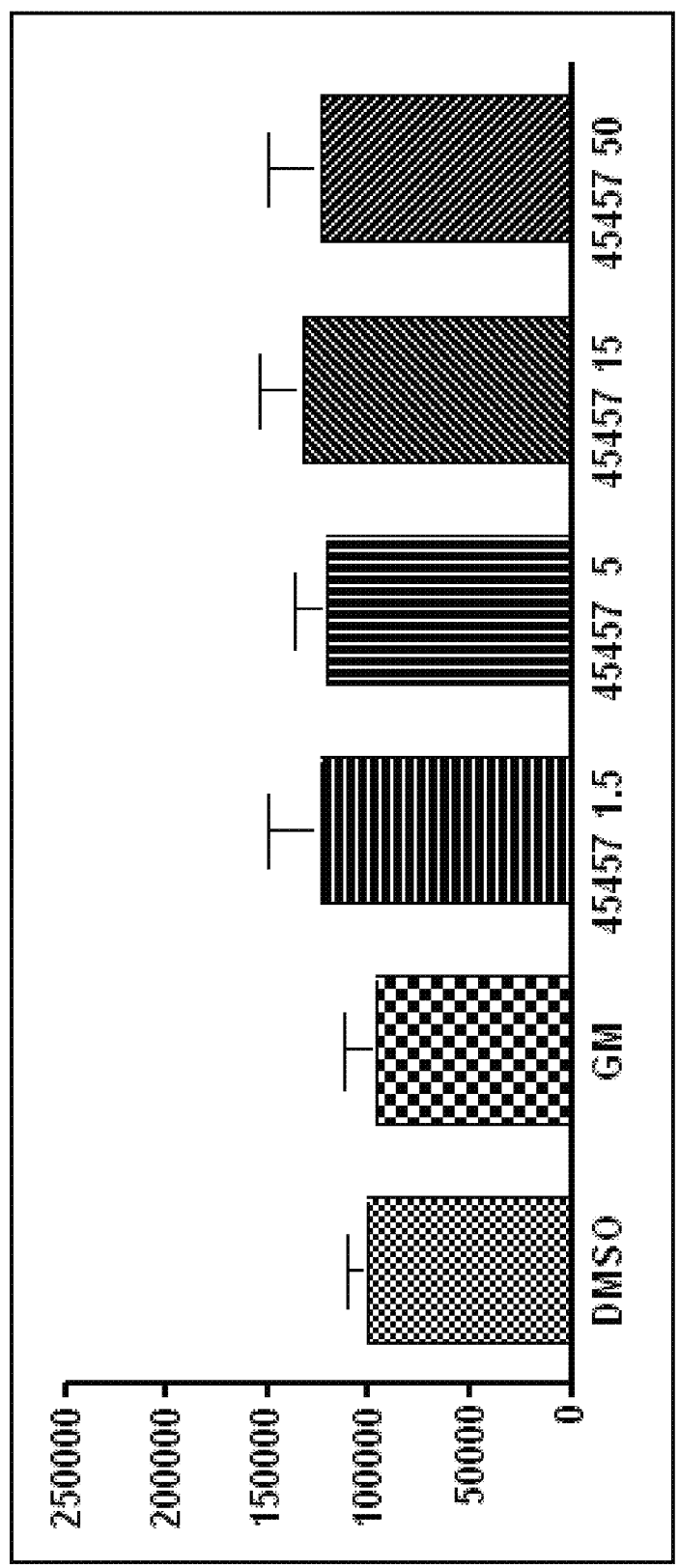
FIG. 15 is a graph showing a total number of iPS cell-derived platelets obtained when GM6001 or S-45457 was added to a culture system for 8 days. The unit of the vertical axis is cell count/well. The value is average+standard error (n=4).
Figure 16:
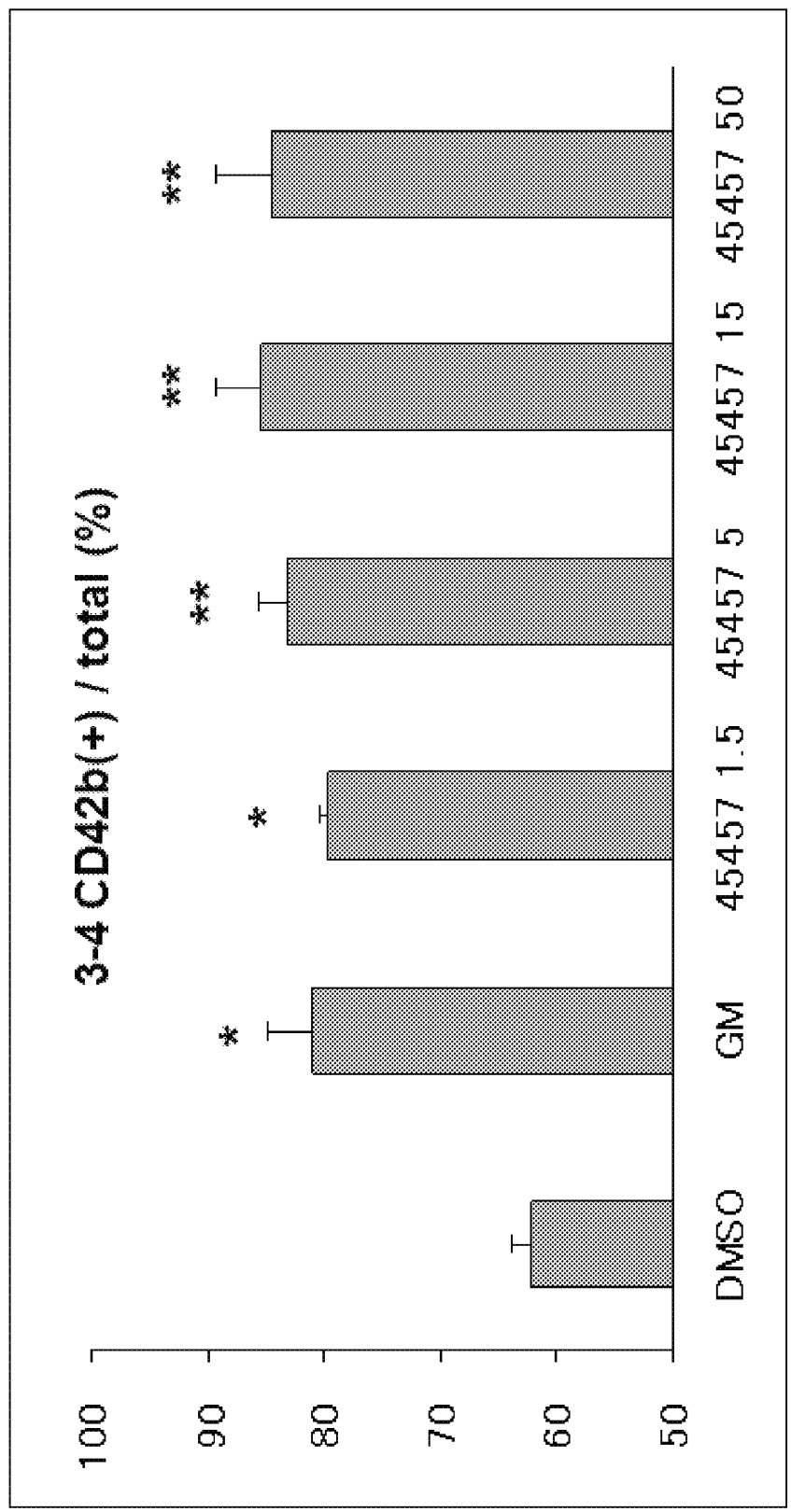
FIG. 16 is a graph for illustrating a concentration-dependence of function-maintaining effect of S-45457 on the iPS cell-derived platelets. The vertical axis represents a percentage (%) of CD42b (GPIbα)(+) where a total number of platelets is taken as 100. * (asterisk) and ** (two asterisks) indicate p<0.05 and p<0.01, respectively.

As apparent from the results shown in FIGS. 14 and 16, it was confirmed that in the culture system using the ES cells (FIG. 14) and also in the culture system using the iPS cells (FIG. 16), the addition of the compound S-45457 according to the present invention inhibit ADAM17-mediated GPIbα shedding in a manner dependent on the added concentration. Further, as apparent from the results shown in FIGS. 13 and 15, it was also confirmed that the compound S-45457 according to the present invention has a low toxicity to ES cells, iPS cells, and differentiated cells from these.

Test Example 8

Figure 17:
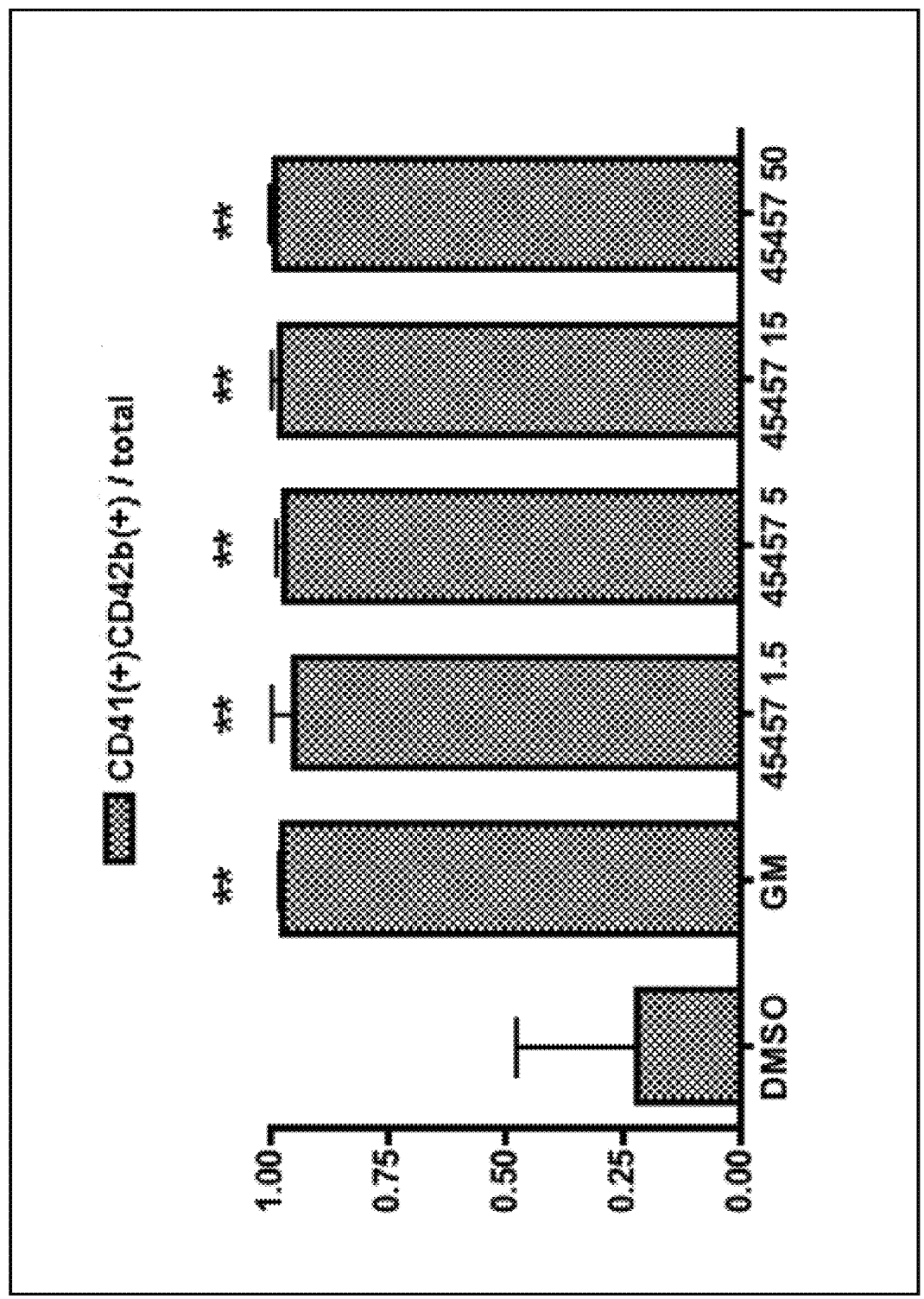
FIG. 17 is a graph for illustrating a concentration-dependence of function-maintaining effect of S-45457 on peripheral blood-derived platelets. The vertical axis represents a percentage of CD41(+)CD42b (GPIbα)(+) where a total number of platelets is taken as 1.00. The value is average value+standard error (n=4). ** (two asterisks) indicates p<0.01.

Verification of Concentration Dependency of Function-Maintaining Effect of S-45457 on Human Peripheral Blood-Derived Platelets It was verified whether the compounds according to the present invention demonstrated function-maintaining effect of on peripheral blood-derived platelets obtained by collecting blood in the same way as platelets obtained using the culture system as described above. Specifically, according to <Protocol 2> illustrated in FIG. 6, first, ACD was added to human peripheral blood obtained by collecting blood at a ratio of 1:10, and centrifuged at 900 rpm for 10 minutes without a break. The supernatant obtained by the centrifugation was further centrifuged at 1500 rpm for 10 minutes without a break, and then the supernatant was removed. The precipitate thus obtained was suspended in a Tyrode-HEPES buffer (not containing calcium). The number of platelets in the suspension was counted, and the suspension (Washed Platelet) was adjusted to contain $5 \times 10^7$ to $1 \times 10^8$ of platelets/200 µL of the Tyrode-HEPES buffer (not containing calcium). Next, one of either 50 µM GM6001, 1.5 to 50 µM S-45457, or DMSO was added together with 100 µM CCCP (carbonyl cyanide m-chlorophenyl hydrazone) to the washed platelets. After incubation at 37° C. for 24 hours, the numbers of CD41(+)CD42b(+) and CD41(+)CD42b(−) were counted by flow cytometry. Incidentally, it is known that addition of CCCP enhances GPIbα shedding on the surface of platelets (see Bergmeier et al, Blood, 2003, vol. 102, pp. 4229 to 4235). FIG. 17 shows the obtained result. The statistical processing was the same as that in Test Example 7.

As apparent from the result shown in FIG. 17, it was confirmed that similarly to GM6001, the compound according to the present invention have a function-maintaining effect, in particular the function-maintaining effect at 37° C., on human peripheral blood-derived platelets.

Test Example 9

Figure 18:
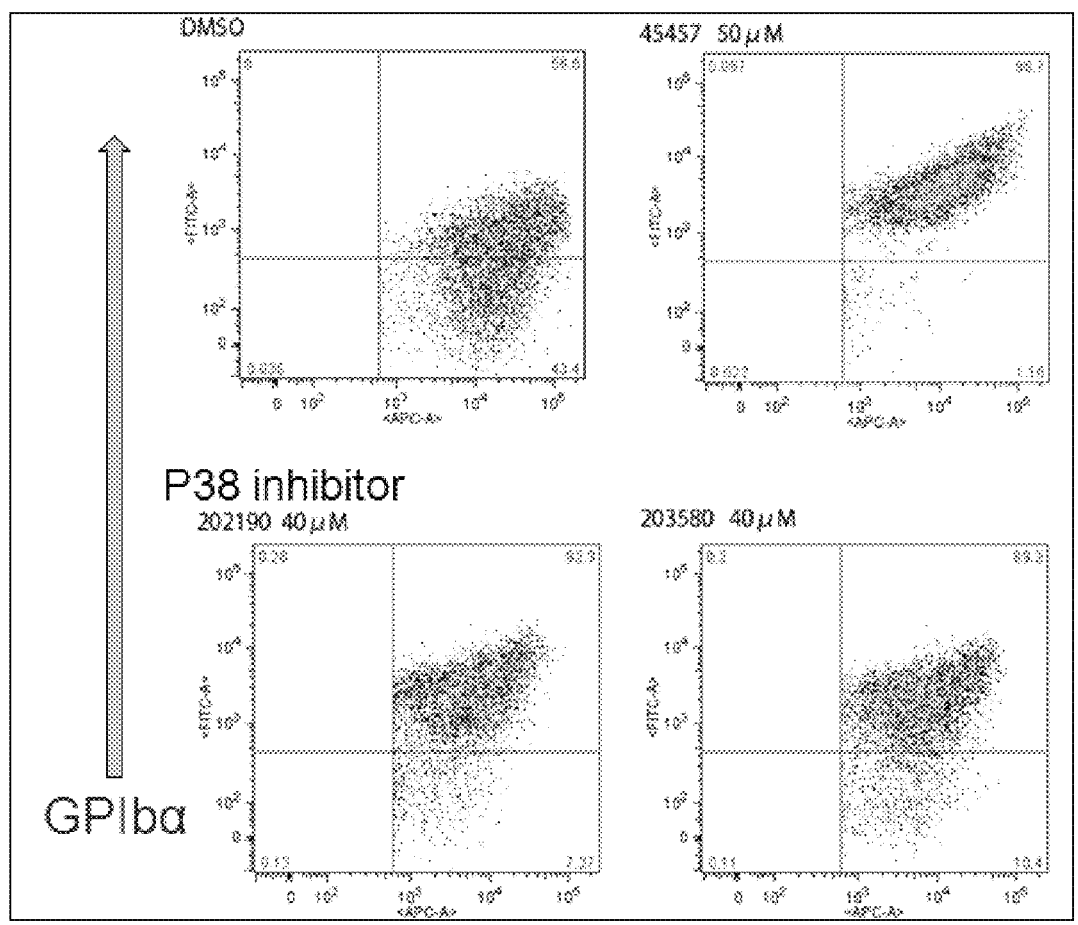
FIG. 18 shows dot plot charts for illustrating function-maintaining effects of S-45457 and p38 inhibitors on peripheral blood-derived platelets.

Verification of Function-Maintaining Effects of S-45457 and p38 Inhibitors on Human Peripheral Blood-Derived Platelets It is known that inhibition of p38 suppresses GPIbα shedding (see Matthias C. et al., TRANSFUSION MEDICINE, BLOOD, Mar. 4, 2010, vol. 115, No. 9, pp. 1835 to 1842). For this reason, the function-maintaining effect on human peripheral blood-derived platelets was compared between p38 inhibitors and the compound according to the present invention. Specifically, one of either each of two 40 µM p38 inhibitors (p38 MAP kinase inhibitors, manufactured by Calbiochem, product numbers: SB202190 and SB203580), 50 µM S-45457, or DMSO was added together with 100 µM CCCP to washed platelets prepared in the same way as in Test Example 8. After incubation at 37° C. for 24 hours, a dot plot analysis on CD41(+) and CD42b(+) was conducted by flow cytometry. FIG. 18 shows the obtained result. Note that, in FIG. 18, the X axis represents CD41, and the Y axis represents CD42b. Moreover, in the graphs, "202190" and "203580" show the result of adding each of the p38 inhibitors at 40 µM (solvent: DMSO).

Figure 19:
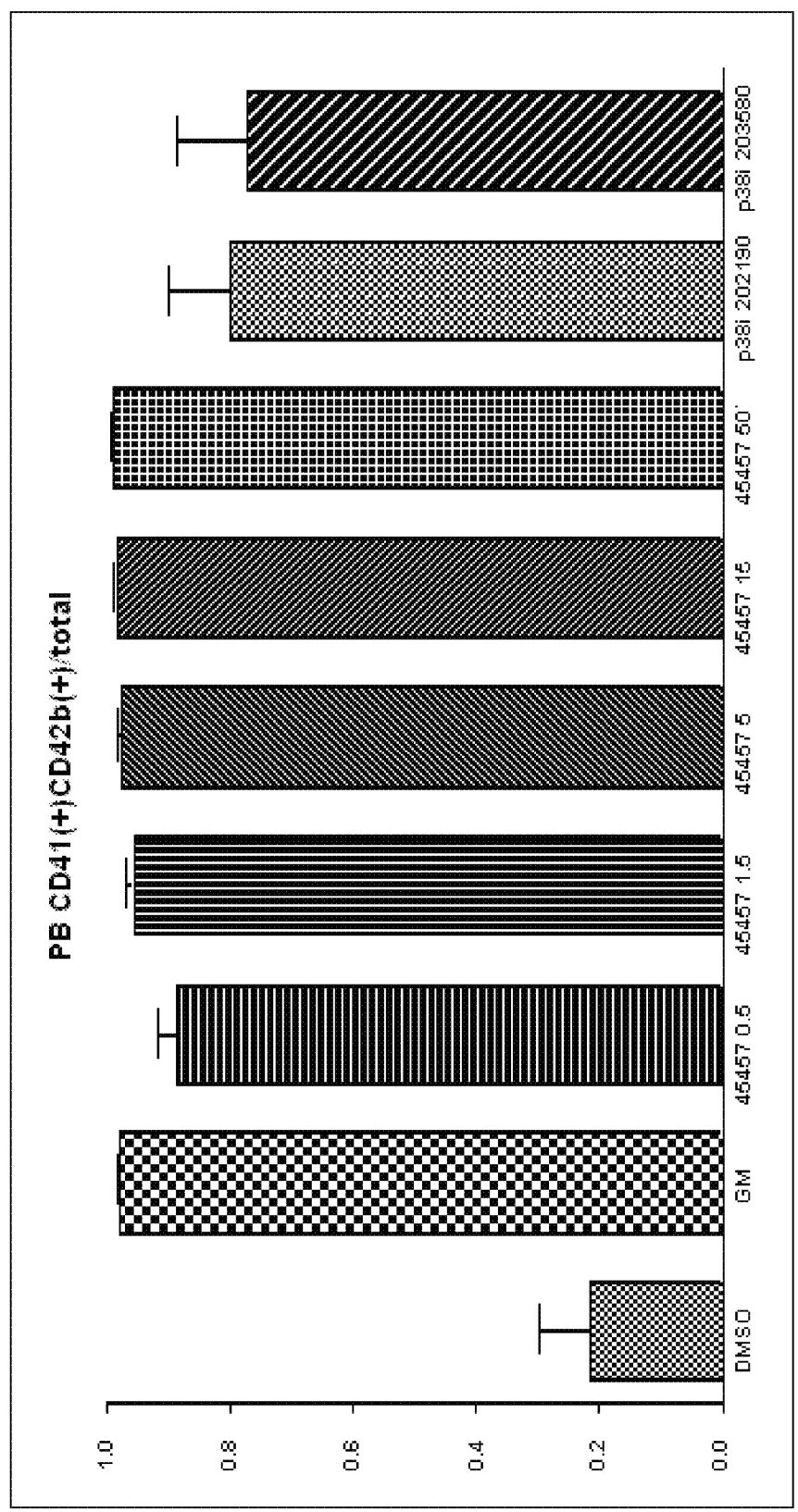
FIG. 19 is a graph for illustrating function-maintaining effects of GM6001, S-45457, and the p38 inhibitors on peripheral blood-derived platelets. The vertical axis represents a percentage of CD41(+) CD42b (GPIbα)(+) to a total number of platelets which is taken as 1.00. The value is average value+standard error (n=4).

In addition, one of either each of the two 40 µM p38 inhibitors, 50 µM GM6001, 0.5 to 50 µM S-45457, or DMSO was added together with 100 µM CCCP to washed platelets prepared in the same way as in Test Example 8. After incubation at 37° C. for 24 hours and flow cytometry analysis, a percentage of CD41(+)CD42b(+) in the platelets was calculated. FIG. 19 shows the obtained result.

As apparent from the results shown in FIGS. 18 and 19, since the numbers of GPIbα (CD42b)(+) cells with addition of the p38 inhibitors were larger than that with DMSO, it was confirmed that the p38 inhibitors also have a function-maintaining effect on human peripheral blood-derived platelets. Nevertheless, the effect produced by adding the compound according to the present invention was superior to the effect produced by adding the p38 inhibitors.

Test Example 10

Figure 20:
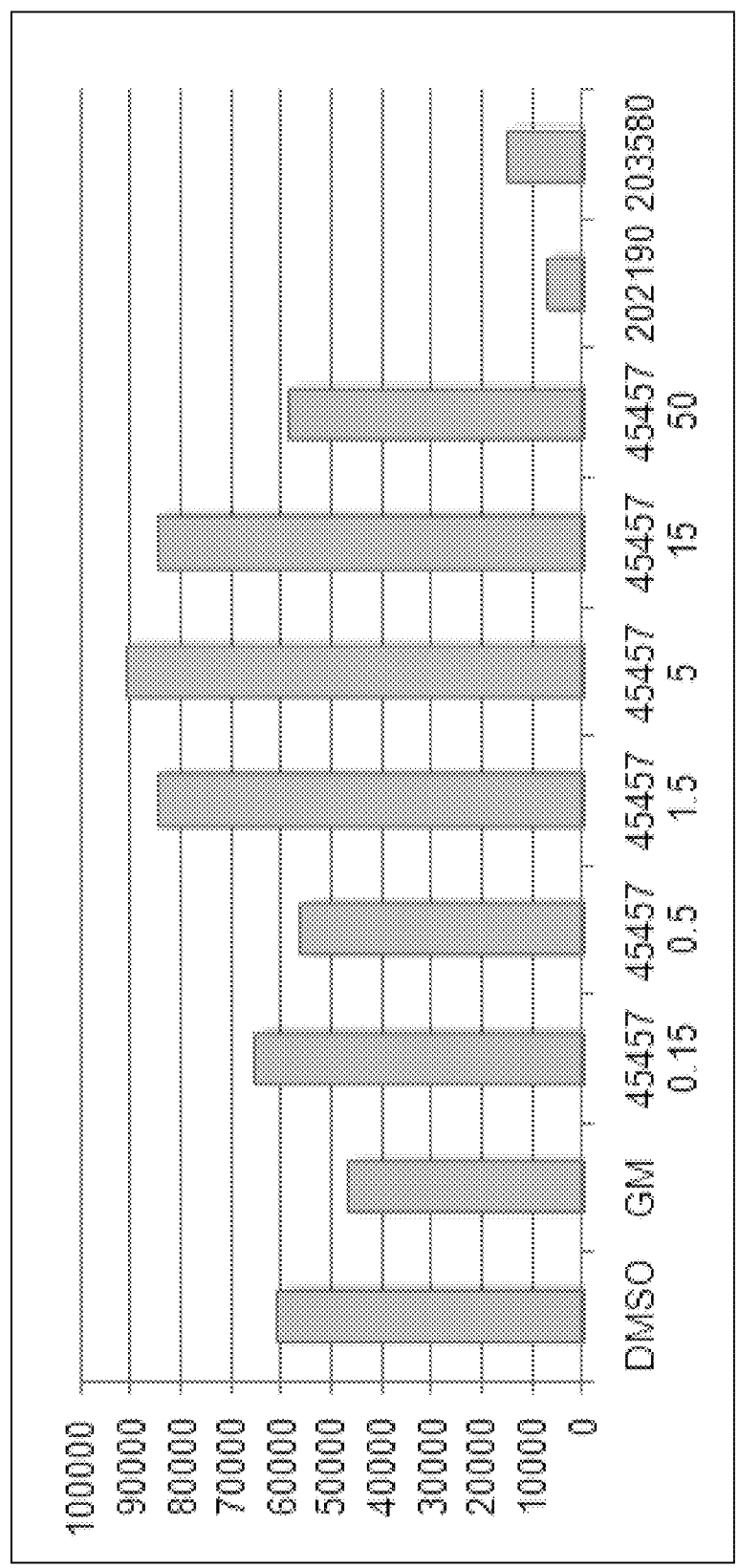
FIG. 20 is a graph showing a total number of ES cell-derived platelets obtained when GM6001, S-45457, or the p38 inhibitors was added to a culture system for 8 days. The unit of the vertical axis is cell count/well.
Figure 21:
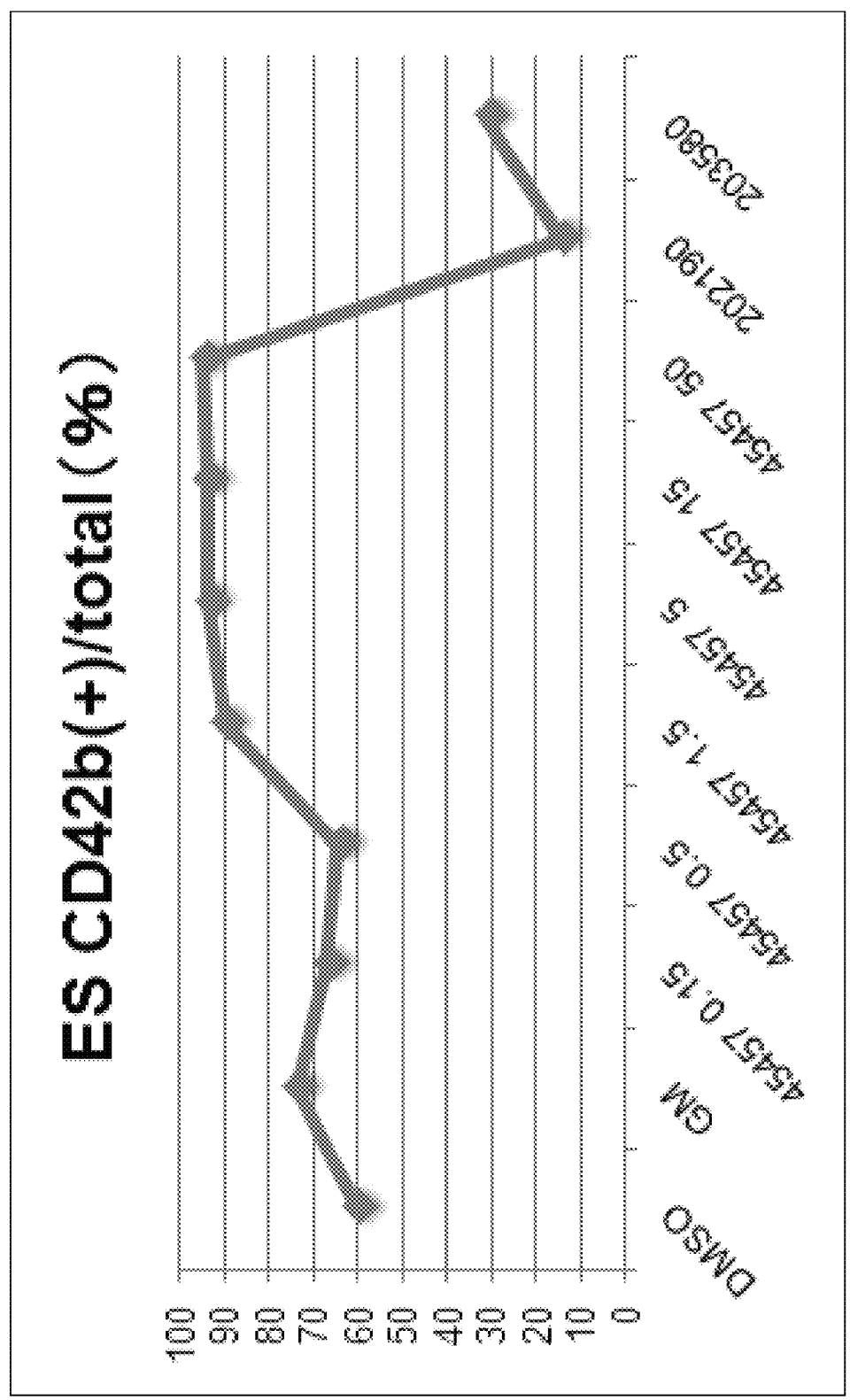
FIG. 21 is a graph for illustrating the result of verification of function-maintaining effects of GM6001, S-45457, and the p38 inhibitors on the ES cell-derived platelets when each compound was added to the culture system for 8 days. The vertical axis represents a percentage (%) of CD42b (GPIbα)(+) where a total number of platelets is taken as 100.

Verification of Function-Maintaining Effects of S-45457 and p38 Inhibitors on ES Cell-Derived Platelets Under the conditions (Protocol 1) illustrated in FIG. 6, platelets were induced from ES cell-derived hematopoietic progenitor cells obtained as described above. Specifically, after ES cell-derived hematopoietic progenitor cells were reseeded (after "d15" shown in FIG. 6), one of either 50 µM GM6001, 0.15 to 50 µM S-45457, each of the two 40 µM p38 inhibitors, 50 µM GM6001, or DMSO was added, followed by culturing for 8 days. After collection as described above, a total number of platelets and a percentage of CD41(+)CD42b (+) in the platelets were determined by flow cytometry and calculated. FIGS. 20 and 21 show the obtained results.

As apparent from the result shown in FIG. 20, the number of platelets obtained by adding the p38 inhibitors was significantly small, and a significant cytotoxicity was confirmed. Moreover, as apparent from the result shown in FIG. 21, the function-maintaining effect on the ES cell-derived platelets produced was observed by adding the compound according to the present invention, whereas none of the effect was observed by adding the p38 inhibitors.

Test Example 11

Figure 22:
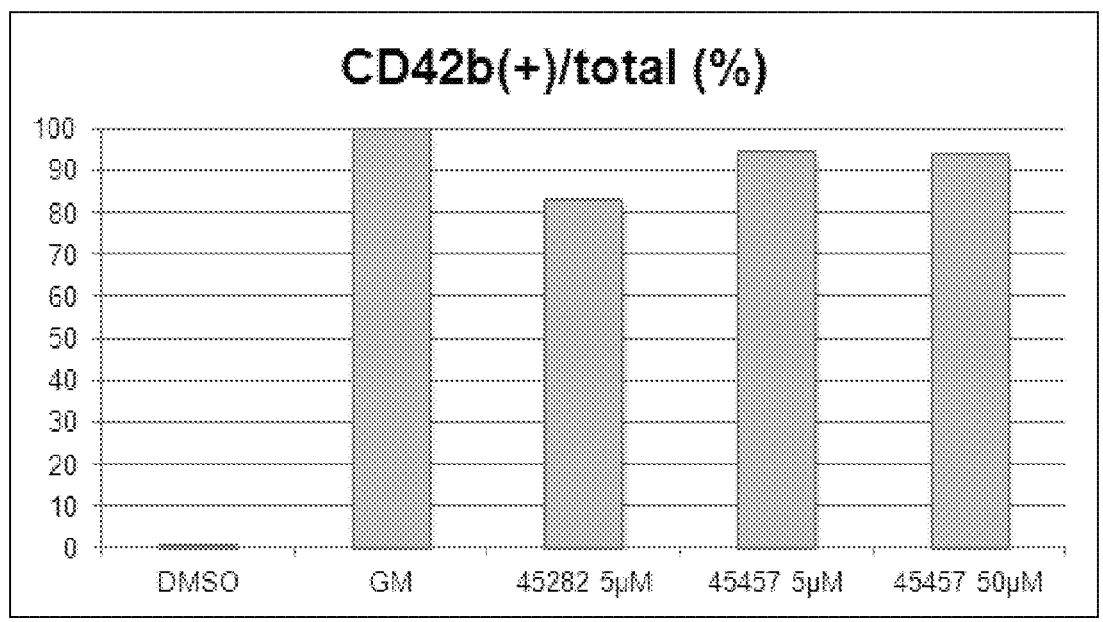
FIG. 22 is a graph for illustrating the result of verification of function-maintaining effects of GM6001, S-45457, and S-45282 on peripheral blood-derived platelets. The vertical axis represents a percentage (%) of CD42b (GPIbα)(+) where a total number of platelets is taken as 100.

Verification of Function-Maintaining Effects of S-45457 and S-45282 on Human Peripheral Blood-Derived Platelets In order to examine function-maintaining effects of S-45457 and S-45282 on human peripheral blood-derived platelets, one of either 50 µM GM6001, 5 µM or 50 µM S-45457, 50 µM S-45282, or DMSO was added together with 100 µM CCCP to washed platelets in the same way as in Test Example 8. After incubation at 37° C. for 24 hours, a total number of platelets and the number of CD42b(+) were counted by flow cytometry, and percentage of CD42b(+) in the platelets was calculated. FIG. 22 shows the obtained result.

As apparent from the result shown in FIG. 22, it was confirmed that similarly to GM6001, the compounds according to the present invention have a function-maintaining effect, particularly the function-maintaining effect at 37° C., on human peripheral blood-derived platelets.

Test Example 12

Verification of Function-Maintaining Effects of on Human Peripheral Blood PRP

Figure 23:
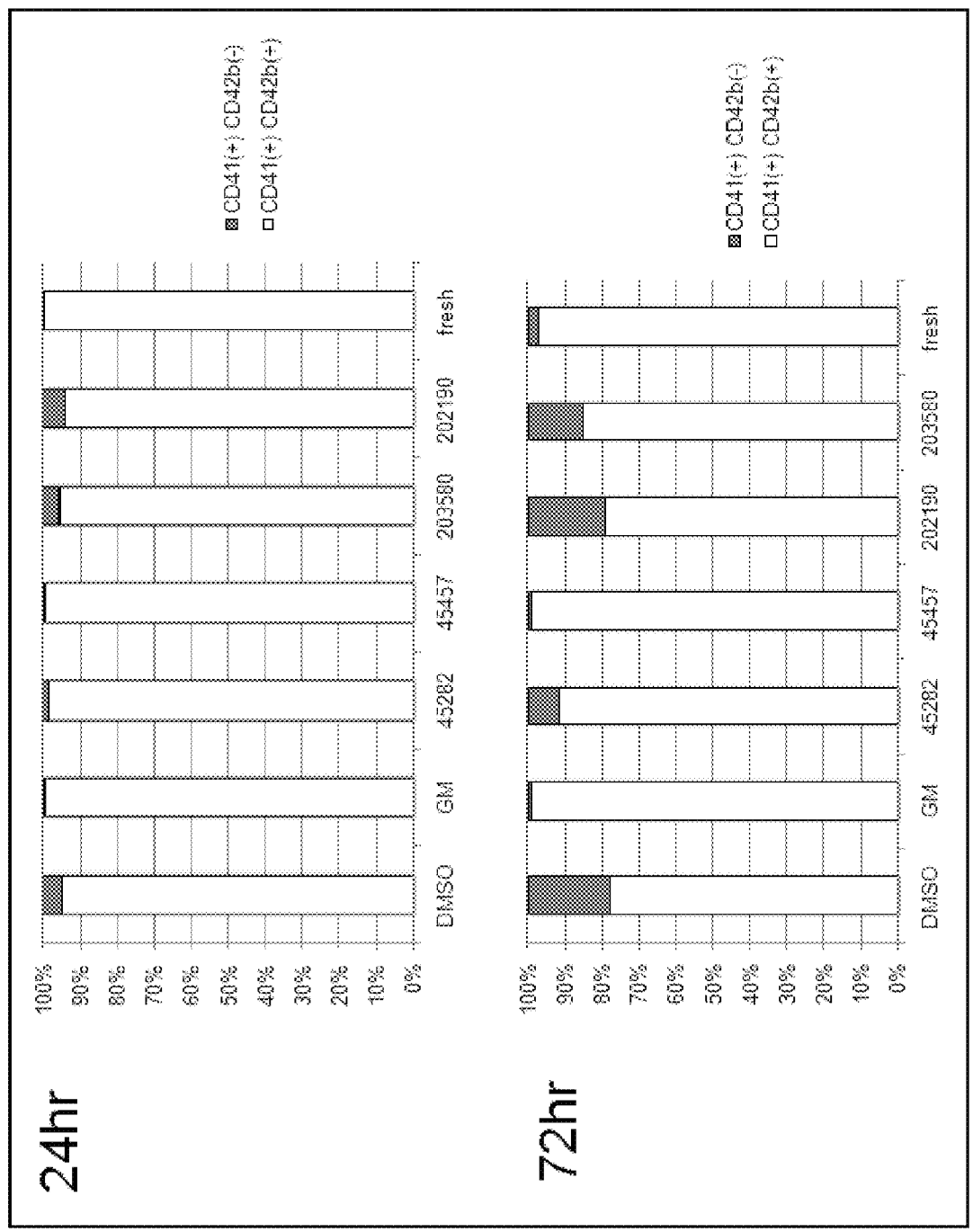
FIG. 23 shows graphs for illustrating the result of verification of function-maintaining effects of GM6001, S-45457, S-45282, and the p38 inhibitors on peripheral blood-derived PRP. The vertical axis represents percentages (%) of CD41 (+)CD42b(+) and CD41(+)CD42b(−) where a total number of platelets (CD41(+)) is taken as 100.

The sustainability of the function-maintaining effect of each compound on platelets was examined using human peripheral blood PRP (platelet-rich plasma). Specifically, first, ACD was added to human peripheral blood obtained by collecting blood at a ratio of 1:10, and the blood was centrifuged at room temperature at 900 rpm for 10 minutes without a break. Next, one of either 50 µM GM6001, 50 µM S-45457, 5 µM S-45282, the 40 µM of two p38 inhibitors, or DMSO was added to the supernatant (PRP) thus obtained. After incubation at 37° C. for 24 hours or 72 hours, the number of CD41(+)CD42b(+) and the number of CD41(+)CD42b(−) were counted by flow cytometry, percentage of CD41(+) CD42b (−) or CD41(+)CD42b (+) in the platelets was calculated. FIG. 23 shows the obtained result. In FIG. 23, "fresh" shows the result of flow cytometry analysis on human peripheral blood PRP not subjected to incubation.

The result shown in FIG. 23 revealed that the compound S-45457 according to the present invention is capable of continuously suppressing ADAM17-mediated GPIbα (CD42b) shedding even incubated for 72 hours. Moreover, it was revealed that the compound S-45282 according to the present invention also has a strong effect of maintaining a function of human peripheral blood PRP in consideration of such an added concentration of 5 µM. Meanwhile, the effects of the p38 inhibitors were observed to be low or hardly observable.

Test Example 13

Figure 24:
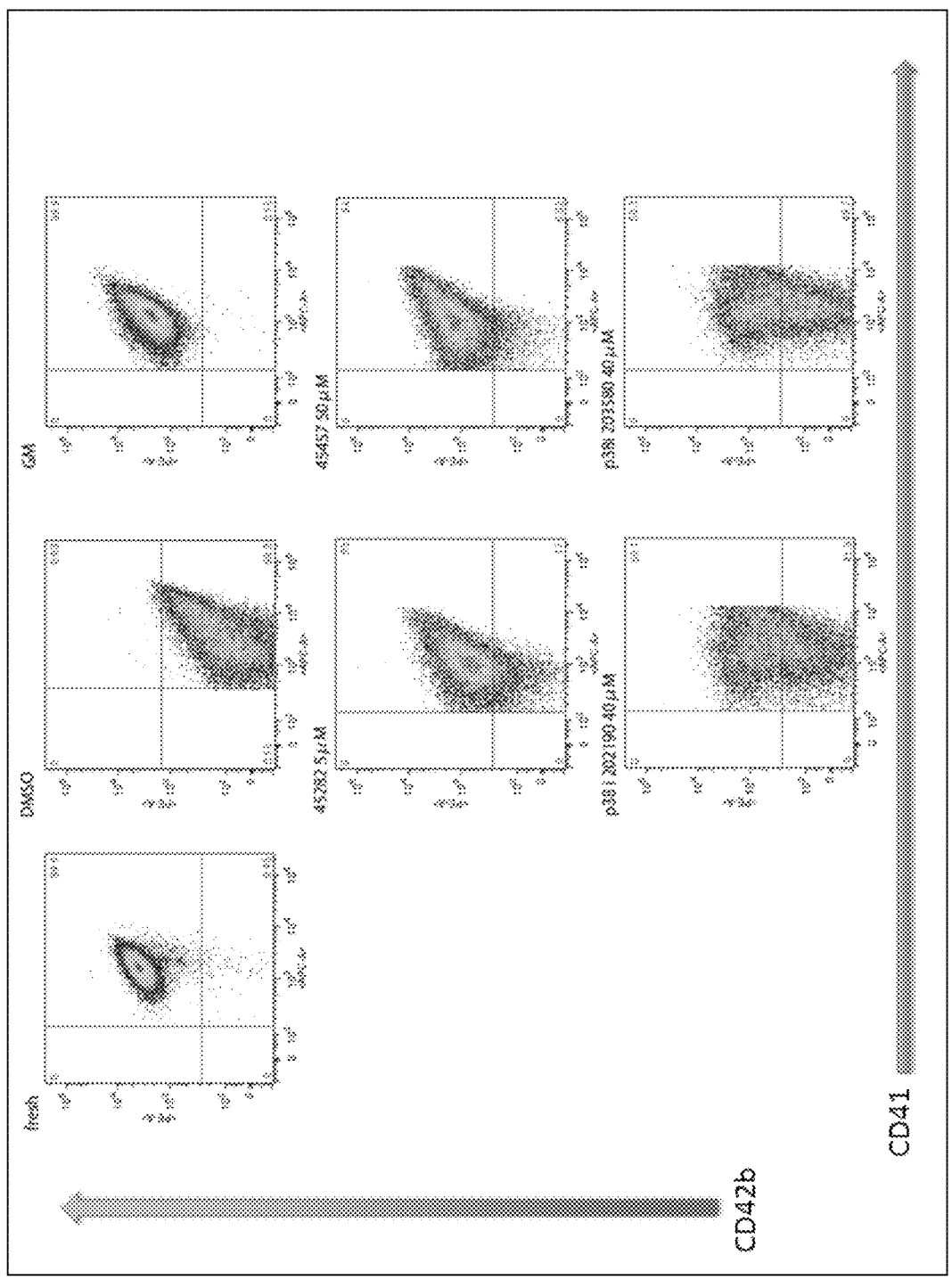
FIG. 24 shows dot plot charts for illustrating function-maintaining effects of GM6001, S-45457, S-45282, and a p38 inhibitor on peripheral blood-derived platelets.

Verification of Function-Maintaining Effects on Human Peripheral Blood-Derived Platelets One of either 50 µM GM6001, 50 µM S-45457, 5 µM S-45282, the two 40-µM p38 inhibitors, or DMSO was added together with 100 µM CCCP to washed platelets obtained in the same way as in Test Example 8. After incubation at 37° C. for 24 hours, by flow cytometry, a dot plot analysis on CD41 (+) and CD42b(+) was conducted. FIG. 24 shows the obtained result. Note that, in FIG. 24, the X axis represents CD41, and the Y axis represents CD42b. Moreover, in FIG. 24, "fresh" shows the result of flow cytometry analysis on washed platelets not subjected to incubation.

As apparent from the result shown in FIG. 24, it was confirmed that the compound S-45457 according to the present invention suppresses ADAM17-mediated GPIbα (CD42b) shedding. Moreover, it was confirmed that the compound S-45282 according to the present invention also has a strong function-maintaining effect on human peripheral blood-derived platelets but not as strong as S-45457. Furthermore, it was confirmed that the effects of the p38 inhibitors are low.

Test Example 14

Figure 25:
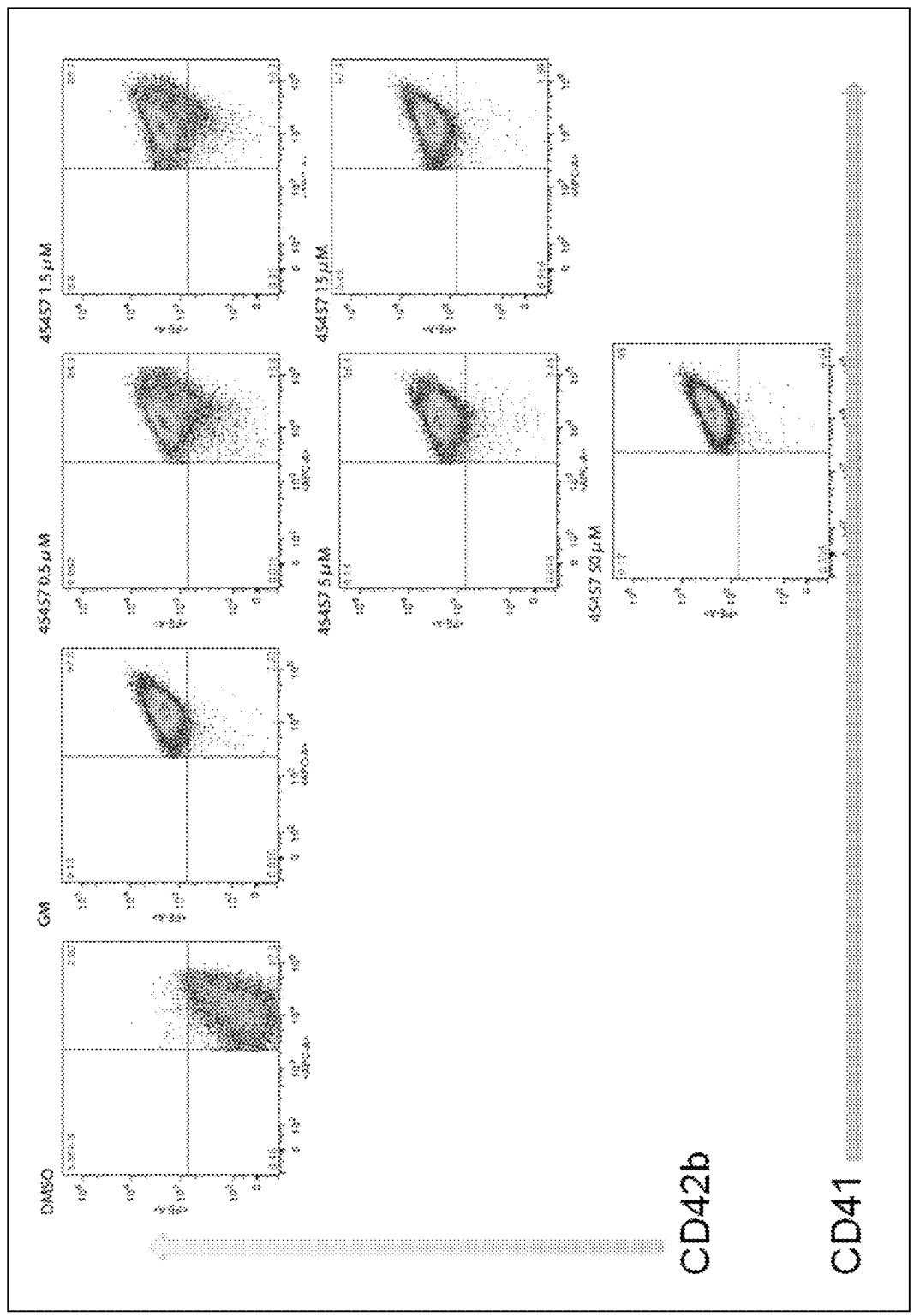
FIG. 25 shows dot plot charts for illustrating a concentration-dependence of function-maintaining effect of S-45457 on peripheral blood-derived platelets.

Verification of Concentration Dependency of Function-Maintaining Effect of S-45457 on Human Peripheral Blood-Derived Platelets One of either 50 µM GM6001, 0.5 to 50 µM S-45457, or DMSO was added together with 100 µM CCCP to washed platelets as in Test Example 8. After incubation at 37° C. for 24 hours, a dot plot analysis on CD41(+) and CD42b(+) was conducted by flow cytometry to examine the function-maintaining effect of S-45457 on human peripheral blood-derived platelets. FIG. 25 shows the obtained result. Note that, in FIG. 25, the X axis represents CD41, and the Y axis represents CD42b.

As apparent from the result shown in FIG. 25, it was confirmed that the compound according to the present invention suppress ADAM17-mediated GPIbα (CD42b) shedding in a concentration-dependent manner.

Test Example 15

Verification of Maintaining Effect of S-45457 on Adhesion Ability of Platelets, Using Flow Chamber It is elucidated that Normally, when the blood vessel wall is damaged, the collagen tissues beneath the vascular endothelial cells are exposed, von Willebrand factor (VWF) in the plasma binds to the collagen tissue; then platelets adhere to the blood vessel by an interaction between VWF and GPIbα (CD42b) and an interaction between VWF and α2bβ3 integrin. In addition, it is clarified that, the platelet adhering to the blood vessel begins platelet to platelet adherence by an interaction between VWF and GPIbα and an interaction between VWF and α2bβ3 integrin, and a thrombus is developed (see Ruggeri Z M., Nature Medicine, November 2002, vol. 8, No. 11, pp. 1227 to 1234).

Hence, whether the effect of the compounds (such as S-45457) according to the present invention suppressing GPIbα shedding demonstrated in Test Examples 1 to 14 maintains an interaction between VWF and GPIbα (CD42b) and contributes to the maintenance of the adhesion ability of platelets or not was evaluated using a flow chamber capable of quantitatively evaluating the course of thrombus formation.

Specifically, first, human peripheral blood was obtained by collecting blood, added with ACD and centrifuged at 900 rpm for 10 minutes without a break to collect a supernatant. The supernatant was added with 1 µM prostaglandin E1 (PGE1), and centrifuged at 1500 rpm for 10 minutes without a break. Then, the supernatant was removed. The precipitate thus obtained was suspended in a Tyrode HEPES Ca(−) buffer, added with 100 µM CCCP and simultaneously added with one of either DMSO or 15 µM S-45457 and followed by incubation at 37° C. for 24 hours. Note that, in this experiment, one obtained by adding CCCP and DMSO and the subsequent incubation was prepared as a negative control, while one obtained without the addition or the incubation treatments was prepared as a positive control.

Further, after the incubation (in the case of the positive control, without incubation), the suspension was added with TMRE (tetramethylrhodamine ethyl ester perchlorate) having been diluted to 1/2000 and incubated at room temperature for 15 minutes to label the platelets with fluorescence. Thereafter, the suspension was added with a Tyrode HEPES Ca(−) buffer and centrifuged at 1500 rpm for 8 minutes without a break in order to wash the platelets.

Figure 26:
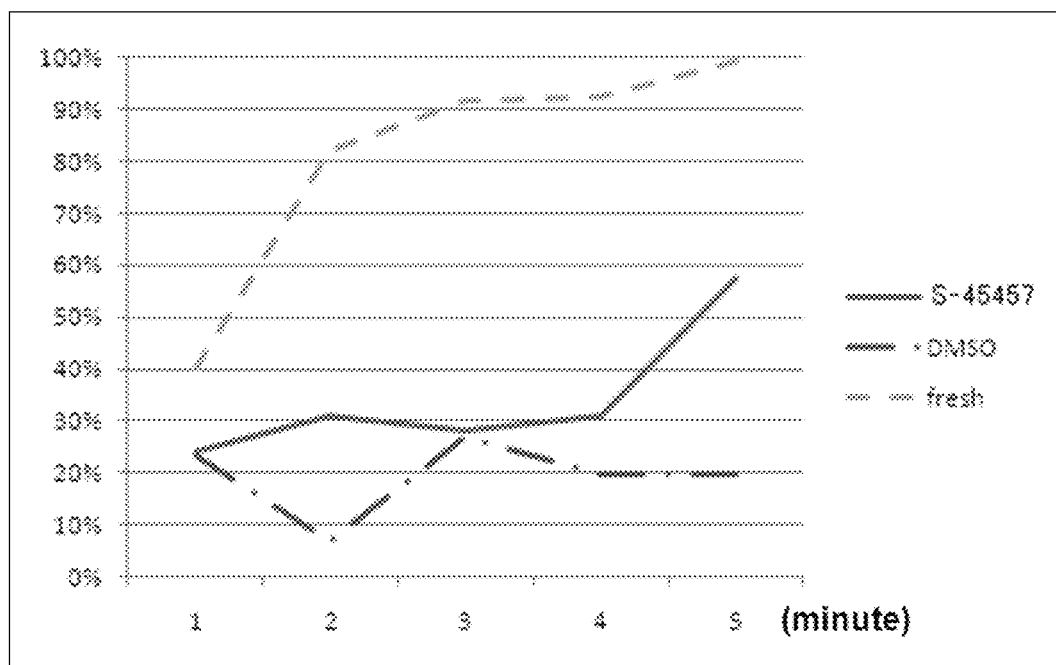
FIG. 26 is a graph for illustrating the result of chronological evaluation of the adhesion ability of platelets prepared in the presence of S-45457.
Figure 27:
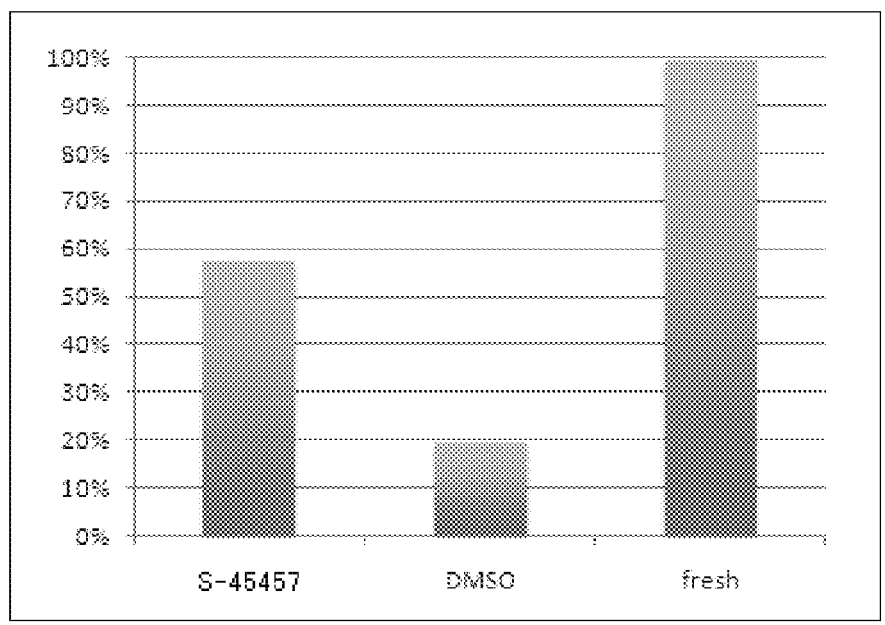
FIG. 27 is a graph for illustrating the result of evaluation of the adhesion ability of the platelets prepared in the presence of S-45457.

Next, each of fluorescence-labelled platelet samples was added to and mixed with a whole blood sample of collected human peripheral blood anticoagulated with argatroban (thrombin inhibitor) so that the number of platelets of the fluorescence-labelled platelet sample was 10% of the whole blood platelets. Then, the blood sample thus prepared was injected into a chamber at a constant wall shear rate (1500 $S^{-1}$) with a syringe pump (manufactured by Harvard Apparatus). The surface of the chamber had been coated with VWF, and platelets in the blood sample adhered to the surface via the VWF. The fluorescence-labelled platelets which formed a thrombus were visualized using an inverted stage epifluorescence video microscope system (DM IRB, manufactured by Leica). The microscopic image was digitized using a photosensitive color CCD camera (L-600, manufactured by Leica). Further, a percentage of surface area covered by platelets was calculated using Image-J software (NIH Image). Note that this experiment was conducted twice for each sample, raw data on each sample was converted to a percentage, with a maximum value of the percentage of surface area covered by the positive control (fresh platelets) taken as 100% for each time, and an average value of the two tests was calculated. FIGS. 26 and 27 show the obtained results. Note that, in FIGS. 26 and 27, the vertical axis represents the average value, "S-45457" shows the result of the platelets prepared by adding 15 µM S-45457, "DMSO" shows the result of the negative control, and "fresh" shows the result of the positive control (fresh platelets). Moreover, in FIG. 26, the horizontal axis represents measurement time (unit: minute) from the injection into the chamber.

As apparent from the results shown in FIGS. 26 and 27, the compound (S-45457) according to the present invention had a high percentage of surface area covered by the platelets in comparison with the result of the negative control added and incubated with DMSO together with CCCP. Accordingly, it was revealed that the compound according to the present invention suppress ADAM17-mediated GPIbα shedding and thus enable association between GPIbα and VWF, i.e., being capable of maintaining the adhesion ability of platelets.

Test Example 16

Verification of Maintaining Effect of S-45457 on Adhesion Ability of Platelets, Using Biomolecular Imaging Technique The maintaining effect of the compound (such as S-45457) according to the present invention on the adhesion ability of platelets, particularly adhesion ability of platelets to a blood vessel in vivo, was evaluated using a biomolecular imaging technique and a thrombus formation model developed by the present inventors.

Note that the thrombus formation model used in this Test Example induces thrombus formation as follows. Specifically, reactive oxygen species (ROS) are generated locally in a blood vessel by using laser irradiation along with hematoporphyrin, and so forth. This gives damage to vascular endothelial cells, and thereby platelets adhere to the blood vessel, so that a thrombus is formed. Moreover, the biomolecular imaging technique used in this Test Example employs a high-speed confocal laser microscope and a multi-beam confocal unit, and thereby a high-speed image can be obtained by focusing on an extremely small area parallel to a direction of blood flow. Accordingly, observation by focusing on platelets or the like flowing through a blood vessel while changing the shape allows for in vivo imaging at an individual platelet level (see Takizawa et al., The Journal of Clinical Investigation, January, 2010, vol. 120, iss. 1, pp. 179 to 190). Hereinbelow, the thrombus formation model and the biomolecular imaging technique used in this Test Example will be described.

First, platelets were prepared for injection into mice used as a model of thrombus formation. Specifically, human peripheral blood was obtained by collecting blood, added with ACD at 10 v/v %, and centrifuged at 900 rpm for 10 minutes without a break to collect the supernatant. The supernatant was added with 1 µM PGE1, and centrifuged at 1500 rpm for 10 minutes without a break. Then, the supernatant was removed. The precipitate thus obtained was suspended in a Tyrode HEPES Ca (−) buffer, to which 100 µM CCCP and DMSO or 15 µM S-45457 were added, followed by incubation at 37° C. for 24 hours. Note that, in this experiment, one obtained by adding CCCP and DMSO and the subsequent incubation was prepared as a negative control, while one obtained without the addition or the incubation treatments was prepared as a positive control. After the incubation (in the case of the positive control, without incubation), the number of platelets in the precipitate was counted. The precipitate was suspended in a 2-ml Tyrode HEPES Ca (−) buffer (containing 1 µM PGE1) and added with 5 µM TMRE. The suspension was then incubated at room temperature for 15 minutes to label the platelets with fluorescence. Thereafter, the suspension was added with a Tyrode HEPES Ca(−) buffer and centrifuged at 1500 rpm for 8 minutes without a break in order to wash the platelets.

Next, the thrombus formation model mouse was prepared. Specifically, an NOG mouse (severe combined immunodeficient mouse) having been subjected to 2-Gy radiation treatment in advance to have fewer platelets was anesthetized and a small incision was made in the abdominal wall to allow for visual analysis of microcirculation and thrombus formation in the mesentery. Further, in order to visualize the kinetics of NOG mouse-derived blood cells, FITC-dextran (20 mg/kg body weight) was injected into the NOG mouse from the caudal vein. Then, platelets labelled with fluorescence as described above were injected into the NOG mouse so that the number of the platelets was 15% of the number of circulating platelets. Further, in order to induce thrombus formation, hematoporphyrin (1.8 mg/kg body weight) was administered into the NOG mouse. Note that by treating the mouse in this manner, the blood cell kinetics and thrombus formation are visualized during laser irradiation and ROS production.

Figure 28:
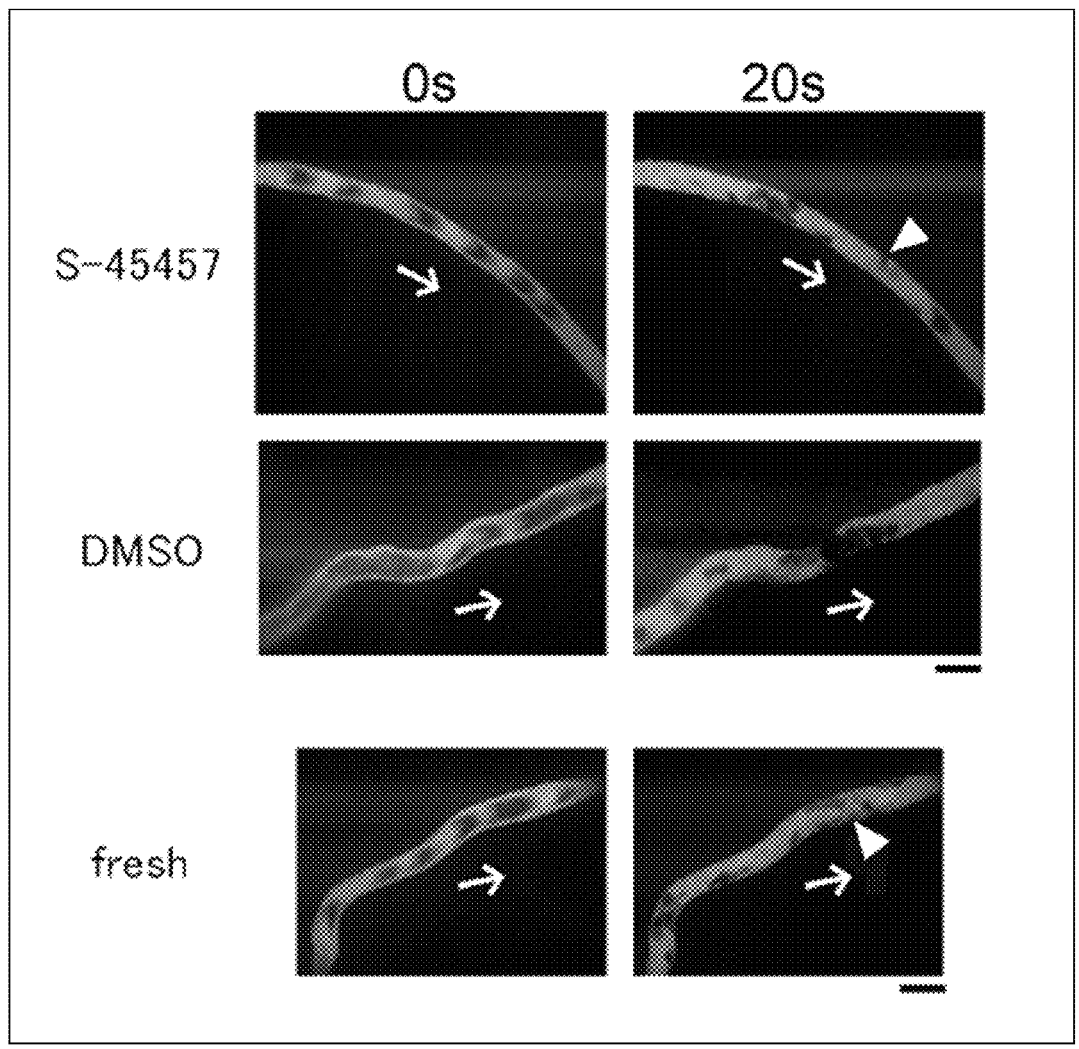
FIG. 28 shows microphotographs at the time of laser irradiation (0 seconds) and 20 seconds thereafter, showing thrombus formation in mice into which platelets prepared in the presence of S-45457 were injected.
Figure 29:
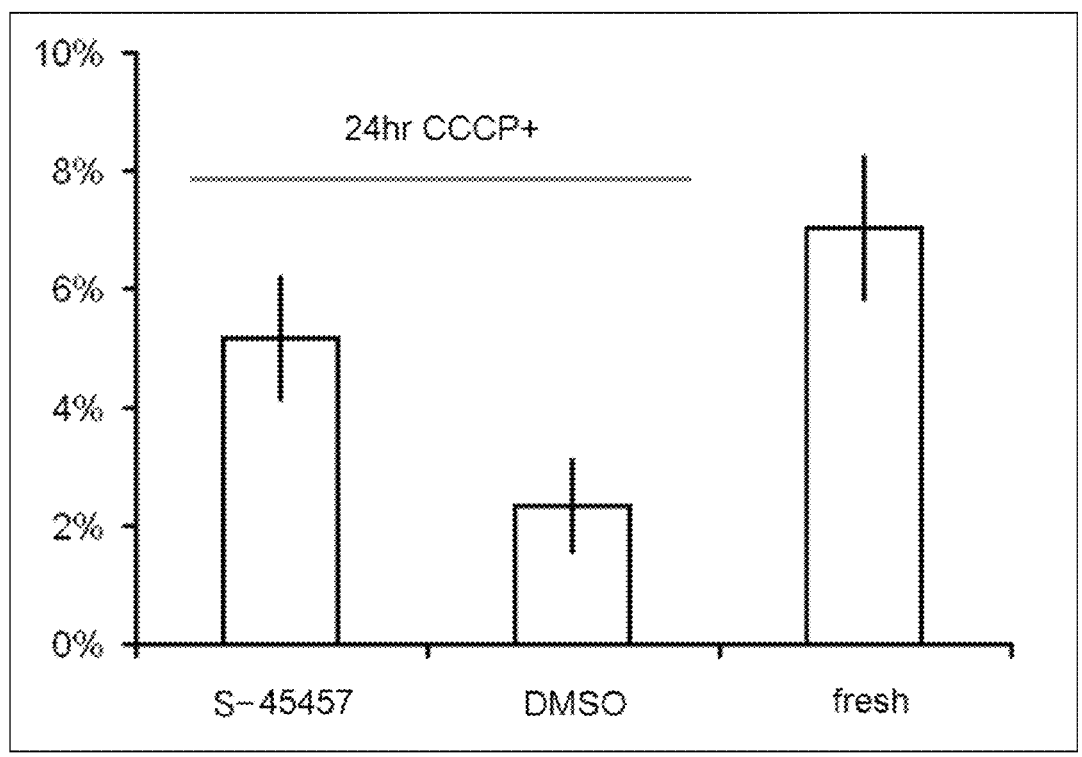
FIG. 29 is a graph for illustrating the contribution of the platelets prepared in the presence of S-45457 to the thrombus formation. The vertical axis is a percentage (%) of the number of human platelets toatotal number of platelets (mouse+human) involved in the thrombus formation, which was obtained by observing obstructive thrombi induced in mensenteric capillaries of mice transfused with each sample. The value is the average of the percentages+standard error obtained by observing 20 blood vessels.

Then, the visualized images (sequential images) during the laser irradiation were obtained by observation and photographing through the previously-made small incision site (approximately 3 mm) using a spinning disk confocal microscope (manufactured by Yokogawa Electric Corporation, CSU-X1) and an EM (Electron Multiplying)-CCD camera (iXon, manufactured by Andor Technology plc.) at frames/second for 20 seconds. Note that such observation was made on 20 independent blood vessels where an obstructive thrombus was formed, in each of the mice injected with the platelets prepared by adding S-45457, the negative control, or the positive control. FIGS. 28 and 29 show the obtained results. Note that in FIGS. 28 and 29, "S-45457" shows the thrombus formation in the mouse into which the platelets prepared by adding 15 µM S-45457 were injected, "DMSO" shows the result of the thrombus formation in the negative control, and "fresh" shows the result of the thrombus formation in the positive control. Moreover, in FIG. 28 that shows typical examples, the white arrow indicates a direction of blood flow, and the site indicated by the white triangle is a site where the human-derived platelets adhere to the blood vessel. The scale bar represents 10 μm. Further, in FIG. 29, the vertical axis is a percentage (%) of the number of human platelets to a total number of platelets involved in thrombus formation, and the value is the average of 20 blood vessels+standard error.

As apparent from the results shown in FIGS. 28 and 29, in the mice into which the platelets prepared by adding the compound (S-45457) according to the present invention were injected, the percentage of the human-derived platelets contributing to the thrombus formation was higher than that of the negative control. Accordingly, it was revealed that the compound according to the present invention suppress ADAM17-mediated GPIbα shedding and is thereby capable of maintaining the adhesion ability of platelets to a blood vessel.

INDUSTRIAL APPLICABILITY

As described above, the present invention makes it possible to maintain a function of platelets by specifically inhibiting a metalloproteinase activity of ADAM17 to suppress GPIbα shedding. Thus, the present invention is useful as a reagent for efficiently producing a large amount of functionally stable and highly safe platelets without requiring complex actions, a drug additive for maintaining a function of platelets in a blood product to stabilize a quality thereof, and other purposes.

The invention claimed is:

1. A composition for maintaining a function of platelets, the composition comprising, as an active ingredient, a compound represented by the following general formula (I) or a salt thereof, or a solvate thereof:

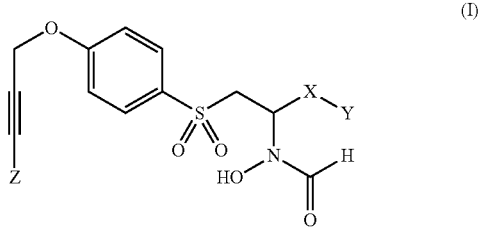

(I)

wherein
X represents a phenylene group;
Y represents —$(CH_2)_m R^1$;
wherein
m represents an integer of any one of 0 to 4; and
$R^1$ represents any one of the following structures

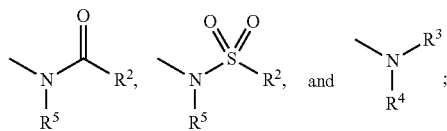

wherein $R^2$ represents any one of a C1 to C6 alkyl group, which may be substituted, an aryl group, which may be substituted, and a C1 to C6 alkoxy group;
$R^3$ and $R^4$ each independently represent any one of a hydrogen atom and a C1 to C6 alkyl group, or $R^3$ and $R^4$ together with an adjacent nitrogen atom may form a nitrogen-containing heterocycle; and
$R^5$ represents any one of a hydrogen atom, a C1 to C6 alkyl group, and a C1 to C6 alkylsulfonyl group; and
Z represents any one of a hydrogen atom and a C1 to C6 alkyl group, wherein the composition comprising a stabilizer or a solvent.

2. The composition according to claim 1, wherein the compound represented by the general formula (I) is any one of
N-[2-(4-but-2-ynyloxybenzenesulfonyl)-1-(4-diethylaminomethylphenyl)ethyl]-N-hydroxyformamide and
N-{4-[2-(4-but-2-ynyloxybenzenesulfonyl)-1-(formylhydroxyamino)ethyl]benzyl}methanesulfonamide.

3. The composition according to claim 1 in a form of any one of a reagent for maintaining a function of platelets and an additive to a blood product comprising platelets.

4. A method for preparing platelets, wherein the method comprises adding, to a culture system for differentiating megakaryocytes from cells capable of differentiating into megakaryocytes and producing platelets from the megakaryocytes, the compound represented by the general formula (I) or a salt thereof, or a solvate thereof according to claim 1.

5. The method according to claim 4, wherein the compound represented by the general formula (I) is any one of
N-[2-(4-but-2-ynyloxybenzenesulfonyl)-1-(4-diethylaminomethylphenyl)ethyl]-N-hydroxyformamide and
N-{4-[2-(4-but-2-ynyloxybenzenesulfonyl)-1-(formylhydroxyamino)ethyl]benzyl}methanesulfonamide.

6. The method according to claim 4, wherein a culture temperature in the culture system is 35 to 38° C.

7. A culture for differentiating megakaryocytes from cells capable of differentiating into megakaryocytes and for producing platelets from the megakaryocytes, comprising the compound represented by the general formula (I) or a salt thereof, or a solvate thereof according to claim 1.

8. The culture according to claim 7, wherein the compound represented by the general formula (I) is any one of
N-[2-(4-but-2-ynyloxybenzenesulfonyl)-1-(4-diethylaminomethylphenyl)ethyl]-N-hydroxyformamide and
N-{4-[2-(4-but-2-ynyloxybenzenesulfonyl)-1-(formylhydroxyamino)ethyl]benzyl}methanesulfonamide.

9. A blood product comprising platelets and a compound represented by the general formula (I) or a salt thereof, or a solvate thereof according to claim 1.

10. The blood product according to claim 9, wherein the compound represented by the general formula (I) is any one of N-[2-(4-but-2-ynyloxybenzenesulfonyl)-1-(4-diethylaminomethylphenyl)ethyl]-N-hydroxyformamide and
N-{4-[2-(4-but-2-ynyloxybenzenesulfonyl)-1-(formylhydroxyamino)ethyl]benzyl}methanesulfonamide.

11. A method for maintaining a function of platelets in a blood product, wherein the method comprises adding, to a blood product comprising platelets, a compound represented by the general formula (I) or a salt thereof, or a solvate thereof according to claim 1.

12. The method according to claim 11, wherein the compound represented by the general formula (I) is any one of
N-[2-(4-but-2-ynyloxybenzenesulfonyl)-1-(4-diethylaminomethylphenyl)ethyl]-N-hydroxyformamide and
N-{4-[2-(4-but-2-ynyloxybenzenesulfonyl)-1-(formylhydroxyamino)ethyl]benzyl}methanesulfonamide.

* * * * *